US005601707A

United States Patent [19]
Clay et al.

[11] Patent Number: 5,601,707
[45] Date of Patent: *Feb. 11, 1997

[54] APPARATUS AND METHOD FOR SUPERCRITICAL FLUID EXTRACTION OR SUPERCRITICAL FLUID CHROMATOGRAPHY

[75] Inventors: Dale L. Clay; Robert W. Allington; Daniel G. Jameson, all of Lincoln, Nebr.; Robin R. Winter, Newburg, Oreg.

[73] Assignee: Isco, Inc., Lincoln, Nebr.

[*] Notice: The term of this patent shall not extend beyond the expiration date of Pat. No. 5,160,624.

[21] Appl. No.: 501,536

[22] Filed: Jul. 12, 1995

Related U.S. Application Data

[60] Division of Ser. No. 382,650, Feb. 2, 1995, which is a continuation-in-part of Ser. No. 96,919, Jul. 23, 1993, abandoned, which is a continuation-in-part of Ser. No. 27,257, Mar. 5, 1993, Pat. No. 5,268,103, which is a continuation-in-part of Ser. No. 908,458, Jul. 6, 1992, Pat. No. 5,198,197, which is a division of Ser. No. 795,987, Nov. 22, 1991, Pat. No. 5,160,624, which is a continuation-in-part of Ser. No. 553,119, Jul. 13, 1990, Pat. No. 5,094,753.

[51] Int. Cl.⁶ .............................. B01D 11/00; B01D 15/08
[52] U.S. Cl. ........................ 210/198.2; 210/511; 210/634; 210/656; 422/256; 422/260
[58] Field of Search ................................... 210/634, 635, 210/656, 659, 198.2, 511; 422/256, 257, 258, 259, 260

[56] References Cited

U.S. PATENT DOCUMENTS

| 524,702 | 8/1894 | Browning | 251/155 |
|---|---|---|---|
| 2,507,851 | 5/1950 | Bryant et al. | 251/155 |
| 3,198,948 | 8/1965 | Olson | 250/106 |
| 3,257,561 | 6/1966 | Packard et al. | 250/106 |
| 3,872,723 | 3/1975 | Busch | 73/194 R |

(List continued on next page.)

FOREIGN PATENT DOCUMENTS

| 124686 | 10/1967 | Czechoslovakia | 210/634 |
|---|---|---|---|
| 438184A1 | 1/1988 | European Pat. Off. | 210/198.2 |
| 275933A2 | 7/1988 | European Pat. Off. | 210/198.2 |
| 416326A2 | 3/1991 | European Pat. Off. | 210/198.2 |
| 458125A3 | 5/1991 | European Pat. Off. | 210/198.2 |
| 450182A2 | 10/1991 | European Pat. Off. | 210/198.2 |
| 458125A2 | 11/1991 | European Pat. Off. | 210/634 |
| 466291A3 | 1/1992 | European Pat. Off. | 210/198.2 |
| 558172A2 | 9/1993 | European Pat. Off. | 210/198.2 |
| 595443A1 | 5/1994 | European Pat. Off. | 210/198.2 |
| 41424 | 3/1907 | Hungary | 210/634 |
| 58-9317 | 2/1983 | Japan | 210/634 |
| 58-38115 | 3/1983 | Japan | 210/634 |
| 63-56425 | 3/1988 | Japan | 210/634 |

(List continued on next page.)

OTHER PUBLICATIONS

Hirata, Y., et al., "Direct Sample Injection in Supercritical Fluid Chromatography with Packed Fused Silica Column", *Journal of High Resolution Chromatography & Chromatography Communications*, vol. 11, Jan. 1988; pp. 81–84.

(List continued on next page.)

*Primary Examiner*—Ernest G. Therkorn
*Attorney, Agent, or Firm*—Vincent L. Carney

[57] ABSTRACT

An apparatus for supercritical fluid extraction incorporates a removable extraction cartridge which in operation has insignificant pressure difference between its inside and outside walls. Because of the low pressure difference, the extraction cartridge need not have the strength to withstand significant pressure and can be made out of molded plastic for disposable use as well as stainless steel and/or machined plastic for reusability. The extraction cartridge can be removed and opened for sample access without the use of tools. The outside of the cartridge can be purged after it is installed in a heated high pressure vessel to remove contamination from its exterior. In one embodiment, the extractor includes a fraction collector for extractants, an automatic sample changer and an automatic cartridge transfer mechanism which provide completely automated extractions.

31 Claims, 20 Drawing Sheets

U.S. PATENT DOCUMENTS

| | | | |
|---|---|---|---|
| 4,032,445 | 6/1977 | Munk | 210/130 |
| 4,064,908 | 12/1977 | Loe | 137/614.17 |
| 4,217,931 | 8/1980 | Jaekel | 137/606 |
| 4,225,290 | 9/1980 | Allington et al. | 417/18 |
| 4,265,860 | 5/1981 | Jennings et al. | 422/280 |
| 4,375,163 | 3/1983 | Yang | 73/61.1 C |
| 4,476,732 | 10/1984 | Yang | 73/863.73 |
| 4,477,266 | 10/1984 | Yang | 55/67 |
| 4,483,773 | 11/1984 | Yang | 210/656 |
| 4,564,145 | 1/1986 | Takada et al. | 239/585 |
| 4,597,943 | 7/1986 | Sugiyama et al. | 422/70 |
| 4,676,897 | 6/1987 | Kuze et al. | 210/659 |
| 4,705,459 | 11/1987 | Buisine et al. | 417/53 |
| 4,711,764 | 12/1987 | Good | 422/65 |
| 4,770,780 | 9/1988 | Moses | 210/634 |
| 4,820,129 | 4/1989 | Magnussen | 417/18 |
| 4,851,683 | 7/1989 | Yang | 250/339 |
| 4,913,624 | 4/1990 | Seki | 417/2 |
| 4,915,591 | 4/1990 | Funke | 417/18 |
| 4,984,602 | 1/1991 | Saito et al. | 137/487.5 |
| 5,013,443 | 5/1991 | Higashidate et al. | 210/634 |
| 5,075,017 | 12/1991 | Hossain et al. | 210/761 |
| 5,087,360 | 2/1992 | Wright et al. | 210/634 |
| 5,094,741 | 3/1992 | Frank et al. | 210/634 |
| 5,094,753 | 3/1992 | Allington | 210/634 |
| 5,133,859 | 7/1992 | Frank et al. | 210/634 |
| 5,147,538 | 9/1992 | Wright et al. | 210/634 |
| 5,151,178 | 9/1992 | Nickerson et al. | 210/659 |
| 5,160,624 | 11/1992 | Clay | 210/634 |
| 5,164,693 | 11/1992 | Yokoyama et al. | 335/14 |
| 5,178,767 | 1/1993 | Nickerson et al. | 210/656 |
| 5,180,487 | 1/1993 | Saito et al. | 210/656 |
| 5,198,197 | 3/1993 | Clay | 422/256 |
| 5,205,987 | 4/1993 | Ashraf-Khorassani et al. | 210/634 |
| 5,253,981 | 10/1993 | Yang | 417/3 |
| 5,268,103 | 12/1993 | Jameson | 210/634 |
| 5,271,903 | 12/1993 | Durst et al. | 422/101 |
| 5,322,626 | 6/1994 | Frank et al. | 210/634 |

FOREIGN PATENT DOCUMENTS

| | | | |
|---|---|---|---|
| 64-44847 | 2/1989 | Japan | 210/634 |
| 2-8039 | 1/1990 | Japan | 210/634 |
| 3-26531 | 2/1991 | Japan | 210/634 |
| 3-251435 | 11/1991 | Japan | 210/634 |
| 463644 | 3/1975 | U.S.S.R. | 210/634 |
| 1552201 | 9/1979 | United Kingdom | 210/634 |
| WO82/01578 | 5/1982 | WIPO | 210/634 |
| WO85/04816 | 11/1985 | WIPO | 210/198.2 |
| WO92/06058 | 4/1992 | WIPO | 210/634 |
| WO94/20190 | 9/1994 | WIPO | 210/198.2 |
| WO95/03106 | 2/1995 | WIPO | |

OTHER PUBLICATIONS

Berger, T. A., et al., "A New Supercritical Fluid Chromatograph", Paper 255, HPLC–92, 16th International Symposium on Column Liquid Chromatography, Lafayette, IN. 1992 pp. A–22 and A 53.

Thiebaut, D., et al., "Supercritical–Fluid Extraction of Aqueous Samples and On–Line Coupling to Supercritical–Fluid Chromatography", *On–Line Coupling of SFE and SFC*, 1989 Elsevier Science Publishers B.V.; pp. 151–159.

Wheeler, J. R., et al., "Supercritical Fluid Extraction and Chromatography of Representative Agricultural Products with Capillary and Microbore Columns", *Journal of Chromatographic Science*, vol. 27, Sep. 1969; pp. 534–539.

Lopez–Avila, Viorica, et al., "SFE/IR Method for the Determination of Petroleum Hydrocarbons in Soils and Sediments", Environmental Monitoring Systems Laboratory, Contract No. 68–C1–0029, Section 4, p. 8.

Levy, Joseph M., et al., "Multidimensional Supercritical Fluid Chromatography and Supercritical Fluid Extraction", *Journal of Chromatographic Science*, vol. 27, Jul. 1989, pp. 341–346.

Schwartz, H. E., et al., "Gradient Elution Chromatography with Microbore Columns", *Analytical Chemistry*, vol. 55, No. 11, Sep. 1983, pp. 1752–1760.

Schwartz, H. E., et al., "Comparison of Dynamic and Static Mixing Devices for Gradient Micro–HPLC", *Journal of Chromatographic Science*, vol. 23, Sep., 1985, pp. 402–406.

SFE–Plus Supercritical Fluid Extraction System brochure, Micro–Tech Scientific. Page 1 and 2.

Kalinoski, Henry T., et al., "Supercritical Fluid Extraction and Direct Fluid Injection Mass Spectrometry for the Determination of Trichothecene Mycotoxins in Wheat Samples", *Anal. Chem.* 1986, 58, 2421–2422.

Ramsey, Edward D., et al., "Analysis of Drug Residues in Tissue by Combined Supercritical–Fluid Extraction–Supercritical–Fluid Chromatography–Mass Spectrometry–Mass Spectrometry", *Journal of Chromatography*, 464 (1989) 353–357.

Sims, Marc, et al., "Design and Control of CO2 Extraction Plants", presented at 2nd International Symposium on Supercritical Fluids, May 20–22, 1991, Boston, MA; pp. 1–8.

Lack, E., et al., "Findings and Experience Acquired in Operating Industrial High Pressure Extraction Plants with Supercritical CO2", pp. 473–480.

Engineered Pressure Systems Inc. "Supercritical Fluid Extraction" brochure. pp. 1–11.

SITEC brochure on HP–Spray Drying/Micronisation/Supercritical Extraction and pilot plants. pp. 1–8.

Brochure from Extract Company GMBH on "Extraction with supercritical gases" production plants. pp. 1–10.

Brochure "Hochdruck–Extraktion—$CO_2$" from UHDE. pp. 1–36.

Korner, J. P., "New Developments in the Design and Construction of Industrial–size SCGE Plants", Proceedings of the International Symposium on Supercritical Fluids, Tome 1, Nice France, Oct. 17, 18, 19, 1988: pp. 633–641.

"Instruments for Separation and Analysis" Product Guide 12, Isco, Inc., Brochure 9501, Jan. 1995.

Suprex Corporation brochure "MPS/225" pp. 1–5.

Specs for Chassis for Ultra Plus Extrapolator by Micro–Tech Scientific, by F. Yang, Sep. 1994. pp. 1–4.

Yang, F. J., et al., "Design Concepts for a New Generation Supercritical Fluid Extraction System", Micro–Tech Scientific pp. 1–12.

McNally, Mary Ellen P., et al., "Supercritical Fluid Extraction Coupled with Supercritical Fluid Chromatography for the Separation of Sulfonylurea Herbicides and their Metabolites from Complex Matrices", *Journal of Chromatography*, 435 (1988) 64–66.

Hawthorne, Steven, et al., "Analysis of Flavor and Fragrance Compounds Using Supercritical Fluid Extraction Coupled with Gas Chromatography", *Anal. Chem.*, 1988, 60, 472–473.

Marc Sims S–F–E brochure on "Dense Gas Management System for Supercritical Fluid Extraction and Processing". pp. 1–4.

Cassat, D., et al., "Extraction of PCB from Contamined Soils by Supercritical $CO_2$", International Symposium on Supercritical Fluids, Tome 2, Nice France, Oct. 17, 18, 19, 1988, pp. 771–776.

De Ruiter, C., et al., "Design and Evaluation of a Sandwich Phase Separator for On–Line Liquid/Liquid Extraction", *Analytica Chimica Acta*, 192 (1987) pp. 267–275.

Advertisement "SFE Analyser 3000", Fisons Instruments SpA; LPI Mar./Apr. 1993. p. 1.

"RIA" Bulletin 7250, Beckman Instruments. pp. 1–9.

"Concept 4" brochure; Micromedic Systems. pp. 1–8.

"The HP 7680A Supercritical Fluid Extractor" brochure; Hewlett–Packard. pp. 1–12.

"Supercritical Fluid (Dense Gas) Chromatography/Extraction with Linear Density Programming" Lyle M. Bowman, Jr., Marcus N. Myers, and J. Calvin Giddings; *Separation Science and Technology*, 17(1) (1982) 271–287.

"Microscale Supercritical Fluid Extraction and Coupling of Microscale Supercritical Fluid Extraction with Supercritical Fluid Chromatography" Muneo Saito, Toshinobu Hondo, Masaaki Senda, *Progress in HPLC* vol. 4 (1989) Yoshioka, et al. (Eds) pp. 87–110.

"Fractionation of Anhydrous Milk Fat by Superficial Carbon Dioxide" by Joseph Arul, Armand Boudreau, Joseph Makhlouf, Rene Tardif, and Madhu R. Sahasrabudhe, *Journal of Food Science* vol. 52, No. 5, 1987, pp. 1231–1236.

"Grobtechnische Anlagen zur Extraktion mit uberkritischen Gasen" by Von R. Eggers; *Angew. Chem.* 90, 1978, pp. 799–802.

"New Pressure Regulating System for Constant Mass Flow Supercritical–Fluid Chromatography and Physico–Chemical Analysis of Mass–Flow Reduction in Pressure Programming by Analogous Circuit Model" by M. Saito, et al.; *Chromatographia* vol. 25, No. 9, Sep. 1988, pp. 801–805.

Wright, B. W., et al., 1987, "Analytical Supercritical Fluid Extraction of Adsorbent Materials", Anal. Chem., 59:38–44.

Sugiyama, K., et al., 1985, "New Double–Stage Separation Analysis Method: Directly Coupled Laboratory–Scale Supercritical Fluid Extraction–Supercritical Chromatography, Monitored With A Multiwavelength Ultraviolent Detector", J. Chromatog., 332:107–116.

Hawthorne, S. B., et al., 1986, "Extraction and Recovery of Organic Pollutants from Environmental Solids and Tenax–GC Using Supercritical $CO_2$", J. Chromatog. Science, 24:258–264.

Hawthorne, S. B., et al., 1987, "Extraction and Recovery of Polycyclic Aromatic Hydrocarbons from Environmental Solids Using Supercritical Fluids", Anal. Chem., 59:1705–1708.

Schantz, M. M., et al., 1986, "Supercritical Fluid Extraction Procedure for the Removal of Trace Organic Species from Solid Samples", J. Chromatogr., 363:397–401.

Wright, B. W., et al., 1989, "Supercritical Fluid Extraction of Coal Tar Contaminated Soil Samples", Energy & Fuels, 3:474–480.

Lee, M. L., et al., 1979, "Retention Indices for Programmed–Temperature Capillary–Column Gas Chromatography of Polycyclic Aromatic Hydrocarbons", Anal. Chem., 51(6):768–774.

Vassilaros, D. L., et al., 1982, "Linear Retention Index System For Polycyclic Aromatic Compounds", J. Chromatogr., 252:1–20.

Czubryt, J. J., et al., 1970, "Solubility Phenomna in Dense Carbon Dioxide Gas in the Range 270–1900 Atmospheres", J. Phys. Chem., 74(24):4260–4266.

Wise, S. A., et al., 1988, "Determination of Polycyclic Aromatic Hydrocarbons in a Coal Tar Standard Reference Material", Anal. Chem., 60:887–894.

Villaume, J. F., 1984, "Coal Tar Wastes: Their Environmental Fate and Effects", *Hazardous and Toxic Wastes: Technology, Management, and Health Effects*, Chapter 25, S. K. Majumdar and E. W. Miller, Eds., pp. 362–375.

Maxwell, R. J., et al., 1992, "Improved SFE Recovery of Trace Analytes from Liver Using an Intergral Micrometering Valve–SPE Column Holder Assembly", J. High Resolution Chromatogr., 15:807–811.

Levy, J. M., et al., 1990, "Qualitative Supercritical Fluid Extraction Coupled to Capillary Gas Chromatography", J. High Resolution Chromatogr., 13:418–421.

Levy, J. M., et al., 1991, "The Use of Alternative Fluids in On–Line Supercritical Fluid Extraction–Capillary Gas Chromatography", J. High Resolution Chromatog., 14:661–668.

Wright, B. W., et al., 1992, "Evaluation of a Field–Portable Supercritical Fluid Extraction Apparatus for Rapid Characterization of Contaminated Soils", *Waste Testing and Quality Assurance: Third Volume*, D. Friedman, Eds., pp. 3–14.

Richter, B. E., 1985, "Modified Flame Ionization Detector for the Analysis of Large Molecular Weight Polar Compounds by Capillary Supercritical Fluid Chromatography", J. High Resolution Chromatogr. & Chromatogr. Communciations, 8:297–300.

Daimon, H., et al., 1991, "Directly Coupled Supercritical–Fluid Extraction/Capillary Supercritical–Fluid Chromatography of Polymer Additives", Chromatographia, 32:549–554.

Levy, J. M., et al., 1989, "Quantitative Supercritical Fluid Extraction Coupled to Capillary Gas Chromatography", Chromatographia, 28:613–616.

Nielen, M. W. F., et al., 1989, "On–line System for Supercritical Fluid Extraction and Capillary Gas Chromatography with Electron–Capture Detection", 474:388–395.

Raynor, M. W., et al., 1988, "Supercritical Fluid Extraction/ Capillary Supercritical Fluid Chromatography/Fourier Transform Infrared Microspectrometry of Polycyclic Aromatic Compounds in a Coal Tar Pitch", J. High Resolution Chromatog. & Chromatog. Communications, 11:766–775

Hawthorne, S. B., et al., 1989, "Coupled SFE–GC: A Rapid and Simple Technique for Extracting", Identifying, and Quantitating Organic Analytes from Solids and Sorbent Resins, J. Chromatog. Science, 27:347–354.

Berger, T. A., et al., 1989, "Linear Velocity Control in Capillary Supercritical Fluid Chromatography by Restrictor Temperature Programming", J. Chromatog., 465:157–167.

Lipsky, S. R., et al., 1986, "High Temperature Gas Chromatography: The Development of New Aluminum Clad Flexible Fused Silica Gases Capillary Colunms Coated with Thermostable Nonpolar Phases: Part 1", J. High Resolution Chromatog. & Chromatog. Communications, 9:376–382.

Green, S., et al., 1988, "Simple Restrictors for Capillary Column Supercritical Fluid Chromatography", J. High Resolution Chromatog. & Chromatog. Communications, 11:414–415.

Raynor, M. W., et al., 1988, "Preparation of Robust Tapered Restrictors for Capillary Supercritical Fluid Chromatography", J. High Resolution Chromatog. & Chromatog. Communications, 11:289–291.

Jinno, K., et al., 1991, "Coupling of Supercritical Fluid Extraction with Chromatography", Anal. Sci., 7:361–369.

Jentoft, R. E., et al., 1972, "Apparatus for Supercritical Fluid Chromatography with Carbon Dioxide as the Mobile Phase", Anal. Chem., 44:681–686.

Campbell, R. M., et al., 1986, "Supercritical Fluid Fractionation of Petroleum– and Coal–Derived Mixtures", Anal. Chem., 58:2247–2251.

Nam, K. S., et al., 1990, "Supercritical Fluid Extraction and Cleanup Procedures for Determination of Xenobiotics in Biological Samples", Chemosphere, 20:873–880.

Campbell, R. M. et al., 1989, "Supercritical Fluid Extraction of Chlorpyrifos Methyl from Wheat at Part per Billion Levels", J. Microcolumn Separations, 1:302–308.

Onuska, F. I., et al., 1989, "Supercritical Fluid Extraction of 2,3,7,8–Tetrachlorodibenzo–p–dioxin from Sediment Samples", J. High Resolution Chromatog., 12:357–361.

Aida, T., et al., 1987, "Organic Chemistry in Supercritical Fluid Solvents: Photoisomerization of trans–Stilbene", ACS Symposium Series 329, *Supercritical Fluids: Chemical and Engineering Principles and Applications*, T. G. Squires and M. E. Paulaitis, Eds., American Chemical Society, Chapter 5, pp. 58–66.

Barber, T. A., et al., 1990, "Solubility of Solid $Ccl_4$ in Supercritical $CF_4$ Using Directly Coupled Supercritical Fluid Extraction–Mass Spectrometry", Separation Science and Technology, 25:2033–2043.

Bond, N. D., 1981, "H–Coal Pilot Plant High Pressure and Temperature Letdown Valve Experience", Proc. of the 1981 Symposium on Instrumentation and Control for Fossil Energy Processes, Argonne National Lab. Report ANL 81–62, Jun. 8–10, pp. 654–679.

Bowman, L. M., 1976, "Dense Gas–Chromatographic Studies", Dissertation, Chapter 3, pp. 35–42.

Driskell, L., 1976, "Coupling with High–Pressure Letdown", Chemical Engineering, 83:113–118.

Gardner, J. F., 1980, "Critical Valve Specifications and METC Valve–Testing Projects", Proc. of the 2nd Symposium on Valves for Coal Conversion and Utilization, DOE/MC/14522–1, Sec. 19.

Giddings, J. C., et al., 1977, "Exclusion Chromatography in Dense Gases: An Approach to Viscosity Optimization", Anal. Chem., 49:243–249.

Grancher, et al., 1973, "The SNPA–DEA Process for the Desulfurization of High Pressure Gases", Proc. of the International Conference on Control of Gaseous Sulphur Compound Emission, Apr. 10–12.

Hartmann, W., et al., 1977, "Fluid Chromatography of Oligomers", Proc. of the 6th Airapt International High Pressure Conference, *High–Pressure Science and Technology*, K. D. Timmerhaus and M. S. Barber, Eds., pp. 573–582.

Hawthorne, S. B., et al., 1990, "Quantitative Analysis Using Directly Coupled Supercritical Fluid Extraction–Capillary Gas Chromatography (SFE–GC) With a Conventional Split/Splitless Injection Port", J. Chromatogr. Science, 28:2–8.

Hawthorne, S. B., et al., 1987, "Directly Coupled Supercritical Fluid Extraction–Gas Chromatographic Analysis of Polycyclic Aromatic Hydrocarbons and Polychlorinated Biphenyls from Environmental Solids", J. Chromatogr., 403:63–76.

Hirata, Y., et al., 1989, "Supercritical Fluid Extraction Combined with Microcolumn Liquid Chromatography for the Analysis of Polymer Additives", J. Microcolumn Separations, 1:46–50.

Illing, H. H., 1982, "Design Principles of Low Impingement Type Slurry Letdown Valves", Proc. of the 1982 Symposium on Instrumentation and Control for Fossil Energy Processes, Argonne National Lab. Report ANL 82–62, pp. 461–468.

Klesper, E., 1978, "Chromatography with Supercritical Fluids", Angew. Chem. Int. Ed. Eng., 17:738–746.

Klesper, E., et al., 1978, "Apparatus and Separations in Supercritical Fluid Chromatography", European Polymer Journal, 5:77–88.

Lapple, C. E., 1943, "Isothermal and Adiabatic Flow of Compressible Fluids", Trans. American Institute of Chemical Engineers, 39:385–432.

Liepmann, H. W., et al., 1957, Flow in Ducts and Wind Tunnels", *Elements of Gasdynamics*, Chapter 5, pp. 124–143.

I. Moradinia, et al., 1987, "Solubilities of Five Solid n–Alkanes in Supercritical Ethane", ACS Symposium Series 329, *Supercritical Fluids*, T. G. Squires and M. E. Paulaitis, Eds., American Chemical Society, Chapter 11, pp. 130–137.

Nair, J. B., et al., "On–Line Supercritical Sample–Preparation Accessory for Chromatography", LC–GC, 6:1071–1073.

Nilsson, W. B., et al., 1989, "Supercritical Fluid Carbon Dioxide Extraction in the Synthesis of Trieicosapentaenoylglycerol from Fish Oil", ACS Symposium Series 406, *Supercritical Fluid Science and Technology*, K. P. Johnston and J. M. L. Penninger, Eds., Chapter 5, pp. 89–108.

Platt, R. J., 1981, "High–Pressure Slurry–Letdown Valve Designs for Exxon Coal–Liquefaction Pilot Plant, Proc. of the 2nd Symposium on Valves for Coal Conversion and Utilization, DOE/MC/14522–1, Sec. 6.

Rizvi, et al., 1988, "Concentration of Omega–3 Fatty Acids from Fish Oil Using Supercritical Carbon Dioxide", ACS Symposium Series 366, *Supercritical Fluid Extraction and Chromatography*, B. A. Charpentier and M. R. Sevenants, Eds., Chapter 5, pp. 89–108.

Saito, M., et al., 1988, "Fractionation by Coupled Micro––Supercritical Fluid Extraction and Supercritical Carbon Dioxide", RSC Chromatography Monographs, *Supercritical Fluid Chromatography*, R. M. Smith, Ed., Royal Society of Chemistry, Chapter 8, pp. 203–230.

Saito, M., et al., 1989, "Enrichment of Tocopherols in Wheat Germ by Directly Coupled Supercritical Fluid Extraction with Semipreparative Supercritical Fluid Chromatography", J. Chromatogr. Sci., 27:79–85.

Smith, R. D., et al., 1986, "Performance of Capillary Restrictors in Supercritical Fluid Chromatography", Anal. Chem., 58:2057–2064.

Temelli, F., et al., 1988, "Supercritical Carbon Dioxide Extraction of Terpenes from Orange Essential Oil", ACS Symposium Series 366, *Supercritical Fluid Extraction and Chromatography*, B. A. Charpentier and M. R. Sevenants, Eds., Chapter 6, pp. 109–126.

Wright, B. W., et al., 1988, "Analytical Supercritical Fluid Extraction Methodologies", ACS Symposium Series 366, *Supercritical Fluid Extraction and Chromatography*, B. A. Charpentier and M. R. Sevenants, Eds., Chapter 3, pp. 44–62.

Conoflow Corp. Valve Catalog sheets for 1968 and 1969.

Greibrokk, T., et al., 1984, "New System for Delivery of the Mobile Phase in Supercritical Fluid Chromatography", Anal. Chem., 56:2681–2684.

Wheeler, J. R., et al., "Is SFC Worth the Effort", Chromatography.

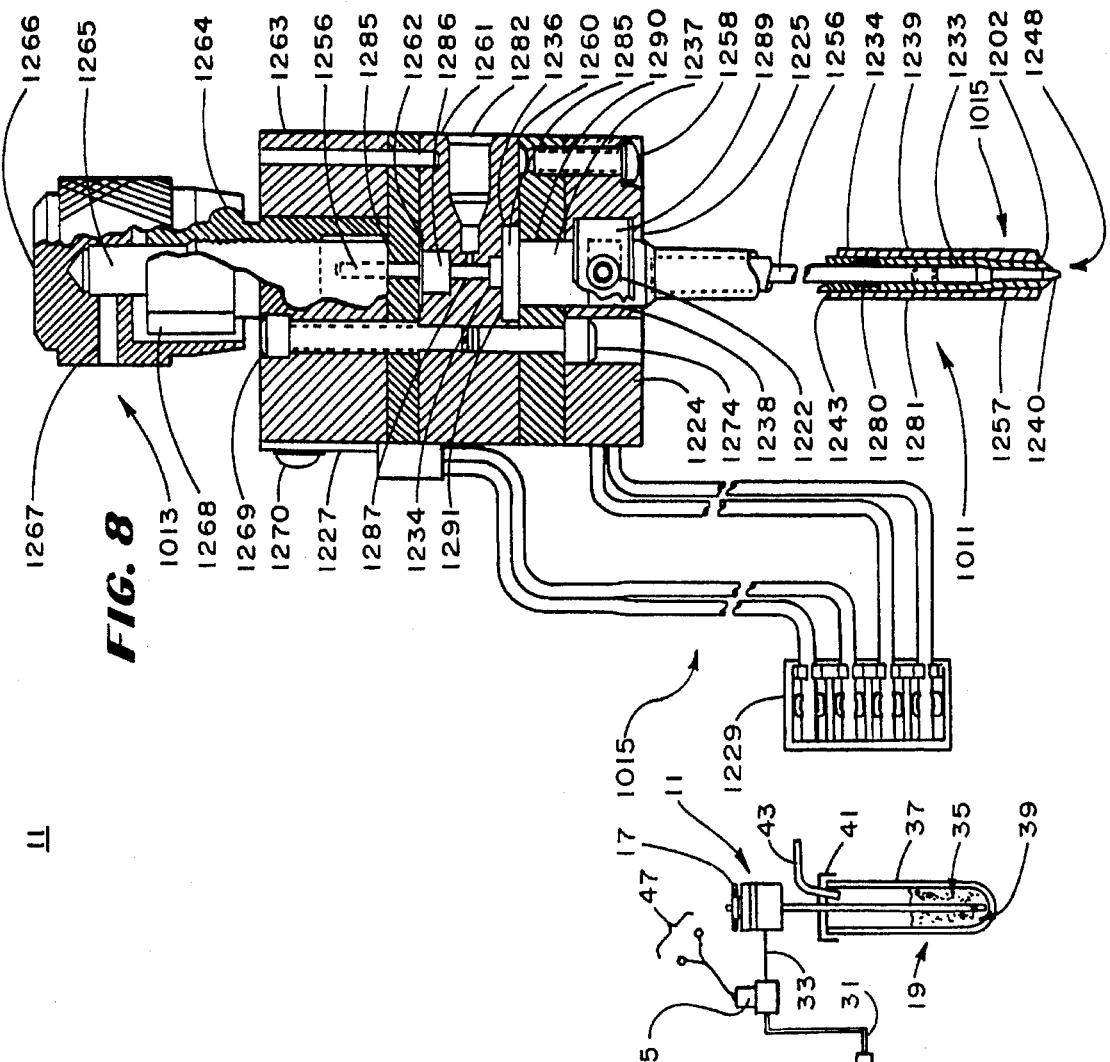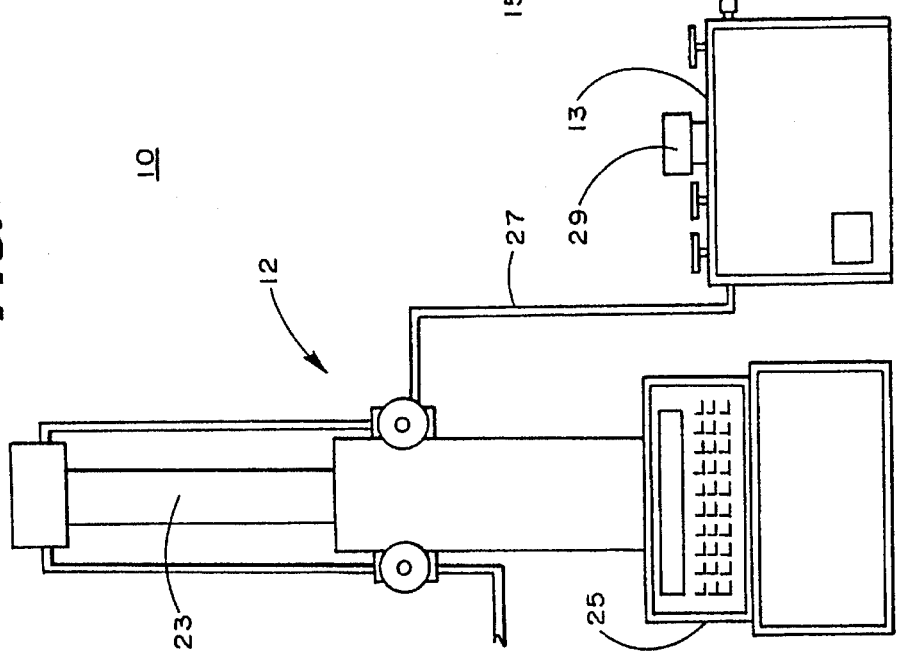

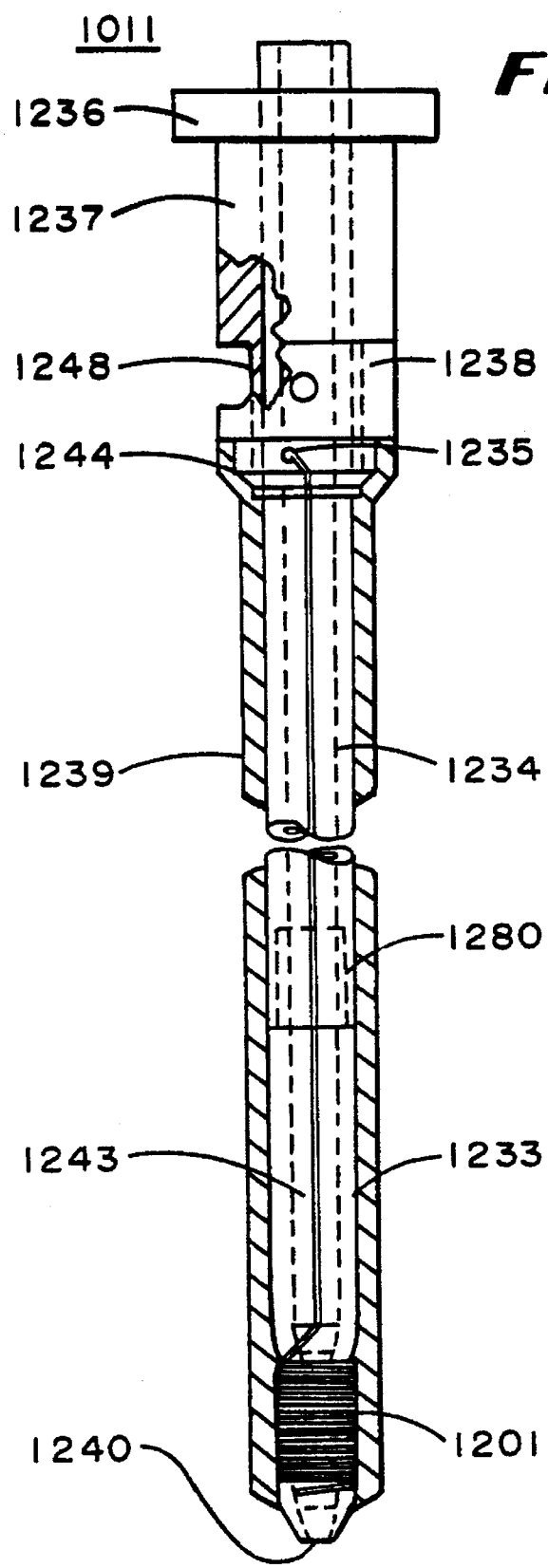
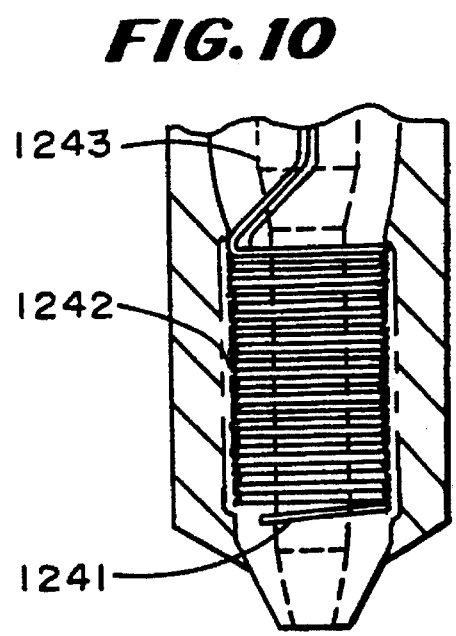
FIG. 9
FIG. 10

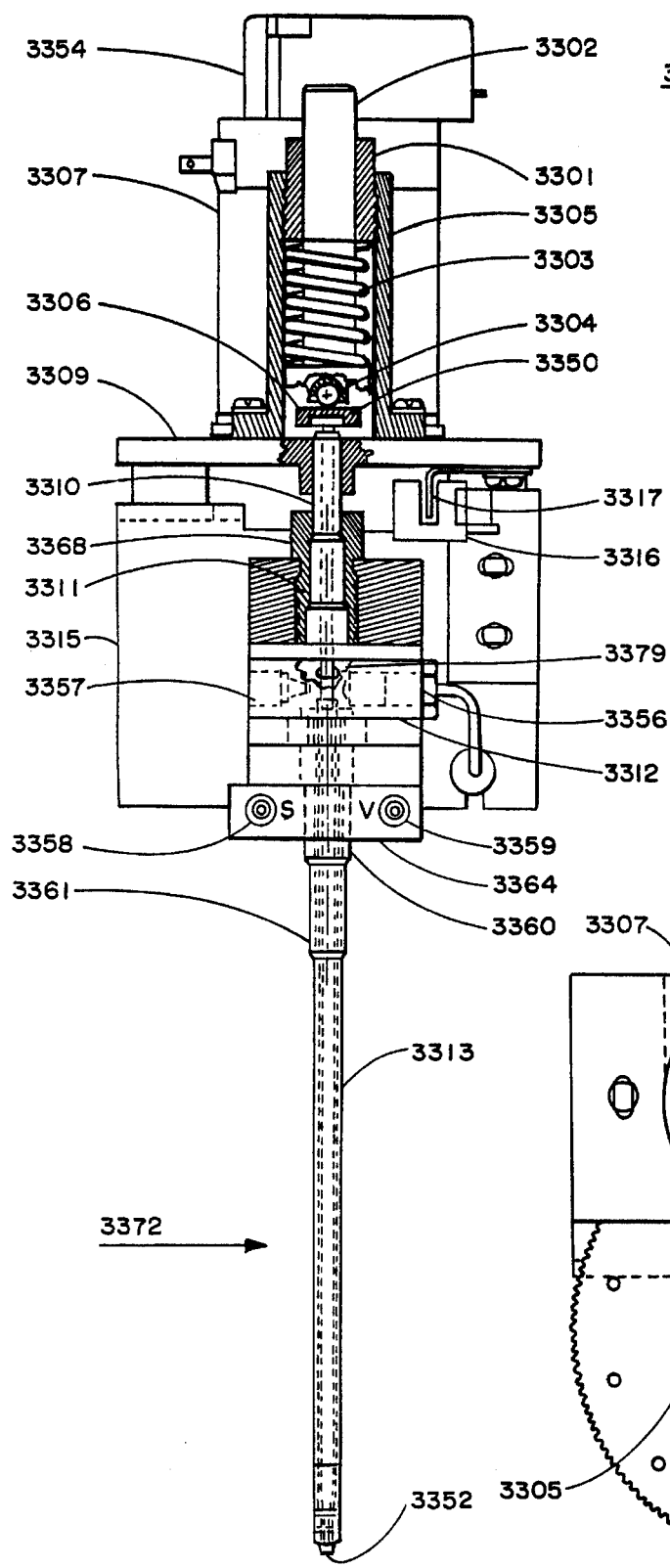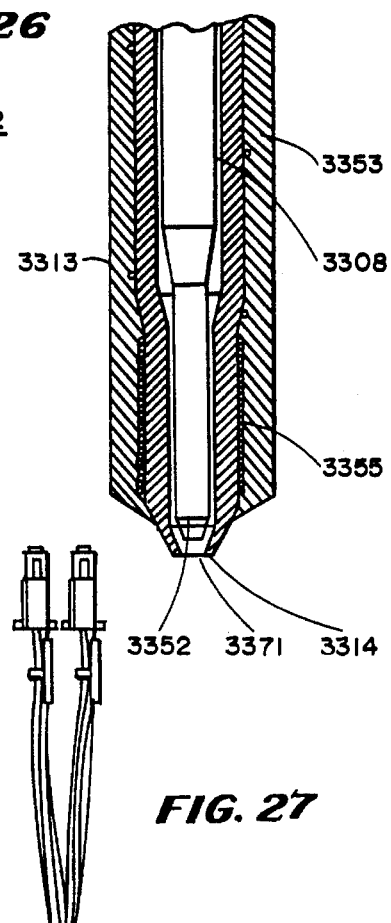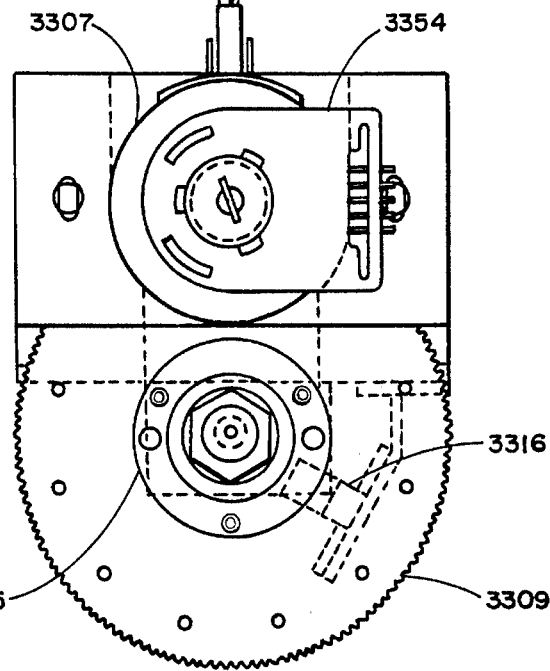

APPARATUS AND METHOD FOR SUPERCRITICAL FLUID EXTRACTION OR SUPERCRITICAL FLUID CHROMATOGRAPHY

RELATED CASES

This application is a divisional application of U.S. patent application No. 08/382,650 filed Feb. 2, 1995, which is a continuation-in-part application of U.S. patent application No. 08/096,919, filed Jul. 23, 1993, now abandoned, which is a continuation-in-part of U.S. patent application No. 08/027,257 filed Mar. 5, 1993, now U.S. Pat. No. 5,268,103 which is a continuation-in-part application of U.S. patent application No. 07/908,458 filed Jul. 6, 1992, now U.S. Pat. No. 5,198,197, which is a division of U.S. patent application No. 07/795,987, filed Nov. 22, 1991, now U.S. Pat. No. 5,160,624, which is a continuation-in-part of U.S. patent application No. 07/553,119, filed Jul. 13, 1990, now U.S. Pat. No. 5,094,753, for APPARATUS AND METHOD FOR SUPERCRITICAL FLUID EXTRACTION.

BACKGROUND OF THE INVENTION

This invention relates to supercritical fluid extraction and supercritical fluid chromatography.

In supercritical fluid extraction, an extraction vessel is held at a temperature above the critical point and is supplied with fluid at a pressure above the critical pressure. Under these conditions, the fluid within the extraction vessel is a supercritical fluid. In supercritical fluid chromatography, a similar process is followed except that the supercritical fluid moves the sample through a column, separates some of the components of the sample one from the other and removes the components from the column.

Prior art apparatuses for supercritical fluid extraction and supercritical fluid chromatography change samples and collect samples manually. These prior art systems have the disadvantages of: (1) requiring time consuming steps to open the pressurized extraction vessels before use to insert the same and again after use to remove the spent sample; and (2) under some circumstances handling hot extraction vessels.

SUMMARY OF THE INVENTION

Accordingly, it is an object of the invention to provide a novel technique and apparatus for supercritical fluid extraction or supercritical fluid chromatography.

It is a still further object of the invention to provide a novel supercritical extraction apparatus that processes a series of samples automatically.

It is a still further object of the invention to provide a novel supercritical extraction apparatus that can use different sizes of collection vials through the use of a variable orifice restrictor whose orifice is located at the end of a long, thin probe.

It is a still further object of the invention to provide a novel supercritical extraction apparatus that allows the vials to be interchanged during the extraction process.

It is a still further object of the invention to provide a novel supercritical extraction collection apparatus that improves trapping efficiency by controlling the temperature and pressure of the collection vial and yet is automatically loaded without the need for handling by an operator.

It is a still further object of the invention to provide a novel supercritical extraction collection apparatus that reduces collection solvent loss by controlling the temperature and pressure of the vial and yet is automatically loaded without the need of handling by an operator.

It is a still further object of the invention to provide a long-lived automatic variable restrictor that cleans itself by relative rotary motion between valve parts when the valve is partially open and regulates flow by relative axial motion between the valve parts.

In accordance with the above and further objects of the invention, an apparatus for supercritical extraction extracts sample with a fluid at an extraction temperature higher than the critical temperature of the said fluid and with the fluid at an extraction pressure higher than the critical pressure of the fluid. Thus, the extraction pressure and extraction temperature define a supercritical condition of the fluid.

In this supercritical extraction apparatus, a plurality of samples are placed in sample containers located on a first transport means. A programming means causes the first transport means to move a selected sample container and sample to the location of a second transport means and causes the second transport means to move said selected container and sample from the first transport means to a place of extraction where the selected container is sealed to resist the extraction pressure and is heated at the extraction temperature. The fluid at the supercritical condition is passed through the selected sample container and sample thereby extracting an analyte from the sample.

After the analyte is extracted, the program causes the second transport means to move the selected container out of the place of extraction and back to the said first transport means. Preferably, the direction of motion of the second transport means is vertical and the direction of motion of the said first transport means is horizontal. This process is repeated. A fraction collector is controlled to collect analyte from each of a plurality of samples in a corresponding one of a plurality of different receptacles.

During collection of the analyte, a controlled variable expansion of supercritical fluid used in supercritical fluid extraction or supercritical fluid chromatography is provided by a restrictor. This restrictor: (1) permits the analyte, which had been dissolved in the supercritical fluid to be deposited directly into an external environment, such as a collection vessel, instead of first depositing it into a connecting conduit that leads to an external collecting vessel; (2) can be used without a connecting conduit; and (3) allows independent control of the fluid back pressure to change the solvating power of the supercritical fluid independently of the flow rate.

The restrictor is variable and incorporates controllable metering means with at least part of said metering means being movable and controllable by an adjusting means extending out of the region comprising the analyte collection means to effect its said control and with its outlet being substantially immediately surrounded by a region comprising an analyte collection means.

Regulation of back pressure (pressure upstream of the tip of the probe) is achieved by a variable orifice created at the tip of the probe. The variable orifice allows control of the flow rate of the fluid independent of pressure, and therefore variable control over the extraction process. Once the extraction fluid is allowed to expand to a gas, its ability to carry the analyte is lost and the analyte precipitates. Because this expansion occurs at the tip of the probe, the analyte precipitates directly into the midst of the collection solvent or particulate medium, thereby improving collection efficiency.

More specifically, a variable-orifice fluid restrictor for use with a supercritical extractor or chromatograph includes an inlet line for fluid at a pressure above its critical pressure and an extended tubular probe having an inner and an outer surface and a proximal and distal end. The proximal end of the probe is disposed toward the inlet line and the distal end is disposed toward the collection environment such as in a collection chamber or the like. The distal end of the probe contains an adjustable orifice means adapted for metering the fluid, which orifice means is comprised of first and second orifice members and an adjusting stem having first and second ends.

The adjustable orifice means is located within the inner surface of the probe adjacent to the outer surface of the probe tip with at least part of the orifice means being movable to effect its said control. Its outlet is substantially immediately surrounded by a region comprising an analyte collection means and is controlled by the adjustable stem that serves as an adjusting means in the preferred embodiment, extending out of the region comprising the analyte collection means. The adjusting stem has first and second ends, the first end of the stem being adapted to movably control the metering means and said second end of the stem carrying a feature which provides for independent control of the metering means.

To automate the operation under the control of a microprocessor, a motor operated fraction collector, a motor operated sample source and a motor operated sample injector automatically move samples and collection containers into an extraction station, inject samples into the extraction pressure vessel, perform extraction and collect extractant in different appropriate collection containers in a timed sequence to permit extracting of a series of samples with minimum human handling.

In the preferred embodiment, a movable motor member is aligned: (1) with an opening in a sample cartridge reel that moves sample cartridges carrying samples into the extraction station; and (2) with an opening in the extraction pressure vessel. The movable member is dimensioned to be capable of sealing a correspondingly sized opening in the pressure vessel and adapted to move the sample cartridge into the pressure vessel and seal the pressure vessel. Motors are provided to operate the valves to permit the extraction operation on the cartridge. The movable member is removed from the pressure vessel after extraction and returns the sample cartridge back to the sample reel.

In operation, the sample to be extracted is placed within the cartridge and the cartridge inserted into and sealed within a pressure vessel. Upon insertion, one of two outlet fittings communicates with the interior of the cartridge and the other with the interior of the pressure vessel outside the cartridge. An inlet to the pressure vessel communicates with the outlet of a pump which pumps the supercritical fluid along a path that heats it and through a programmable valve into the interior of the pressure vessel and extraction cartridge. For each extraction, the valve is automatically opened by a computer controlled motor that releases a valve element to permit flow and closes it to prevent further flow.

To remove any contaminants from outside of the cartridge, the outlet communicates within the inside of the pressure vessel and outside of the cartridge and thus, permits the supercritical fluid to cleanse the outside of the cartridge and the inside walls of the pressure vessel from contaminants as it flows outwardly to a contaminant collector.

For extraction, the cartridge includes an outlet that cooperates with an extractant outlet of the pressure vessel and is connected to the fraction collector so that supercritical fluid flows into the cartridge, out of a fitting that communicates with the interior of the cartridge and into an appropriate collection container.

In the operation of an automatic supercritical fluid extractor, sample cartridges are disposed in the sample changer and are automatically transported to the pressure vessel for extraction by a supercritical fluid. In the preferred embodiment, this transport is first horizontal in a reel of successive sample vials and then vertical through an opening into the pressure vessel. The transport mechanism seals the pressure vessel and is locked in place and motor-driven valves automatically apply extracting fluid first through a purge cycle and then through one or more extracting cycles to extract fluid. A fraction collector, which in the preferred embodiment is a reel holding container, moves the fraction collector containers into position for collection. In the alternative, extractant fluid tubing may be moved from container to container.

An embodiment of collection vial piercing mechanism includes means for adding temperature and positive internal pressure control for the vial. Positive pressure in the vial suppresses misting of the collection solvent and loss of dissolved analyte. Excess gas from the vial is contained and then routed to a remote location for collection and disposal.

To collect sample, one embodiment of collection system includes multiple collecting vials partially filled with collection solvent through which the restrictor bubbles $CO_2$ with entrained analyte. Each vial has a slitted septum on its upper, open end to allow passage of the end of the restrictor into the vial. In one embodiment, the restrictor is lowered into a vial. In another embodiment, the vial is lifted onto the restrictor by a rod connected directly to the extraction cartridge elevator.

In still another embodiment, the vial is lifted by a vial lifter that is separate from the cartridge elevator. To permit changing of the vial during the extraction process, a lift that functions separately from the sample cartridge elevator is required.

This embodiment has the advantage over moving restrictor embodiments of not causing wear and breakage of the restrictor by flexing its connecting tubing repeatedly. It has the advantages of the embodiments in which the vial lifter is directly connected to the cartridge elevator of: (1) allowing the vials to be changed during the extraction process without depressurizing the extraction chamber; (2) better trapping efficiency; (3) lower extract/solvent losses; (4) reduced freezing and plugging of the restrictor; and (5) reduced icing up of the outside of the vial.

The ability to change vials during the extraction process has several advantages, such as for example: (1) it makes it relatively easy to change the conditions of the extraction, such as temperature and pressure or to remove certain substances from the sample matrix and deposit each substance in a separate vial; (2) it is useful for investigating extraction kinetics; and (3) if a separate lift is used, different size vials may be accommodated since the stroke is no longer tied to the extraction cartridge elevator.

Changing a collection vial after an extraction without having to depressurize the extraction chamber makes using multiple wash stations easier. Wash stations are used to clean the outside of the restrictor. Several vials are used in sequential washes of the restrictor to dilute any possible contamination from one extraction to another to acceptable levels. Without a separate vial lift, the chamber would have to be depressurized and repeatedly loaded with a blank for each washing step.

Trapping efficiency and low collection solvent losses can be gained by several techniques. One such technique requires reduced collection solvent temperature during extraction on the order of five degrees Centigrade or less. However, reduced temperature, while improving trapping and reducing losses, may also create problems with restrictor plugging and icing up of the vial. Ice on the outside of a vial may interfere with the vial being lowered into the vial rack after collection. To prevent these problems, heat must be supplied to the vial to maintain a minimum temperature. Ideally, a system would precool the vial before the extraction begins and then add or remove heat to maintain this temperature.

To improve trapping and reduce losses, a sealed system is used with a regulator to maintain pressure, and the collection vials are pressurized sufficiently to reduce the mist containing analyte and vapors resulting from the violent expansion of the gas exiting the restrictor in an unpressurized vial and to prevent loss of gas through the vial's vent. The pressure is sufficiently elevated to stop misting and to decrease the vaporization rate of collection solvent and analyte, and so that at a given mass flow rate of gas, the gas volume and bubble size are reduced. In the sealed system, the gases and vapors may be routed for proper and safe disposal.

To maintain an adequate solvent level, a liquid level control system with sensing of the liquid level in the vial may be provided. This system activates a collection solvent replenishment means when the collection vial loses too much collection solvent due to evaporation. The fluid level sensing system benefits from the pressurized system because increased pressure reduces the violent bubbling and this makes sensing easier. Alternatively, the replenishing fluid may be added according to a present program, with no level sensing used. This is made possible by the reproducible and predictable operating conditions that obtain when using the preferred embodiment of restrictor.

In one embodiment, the collector includes means for receiving the fluid from the extractor and supplying it to a collection liquid at a temperature that permits partition of the analyte between the trapping solvent and the extractant by avoiding freezing of the extractant before partition but at a temperature not so high as to cause the bubbling away of the extract with the extractant. This usually involves cooling the collection liquid.

The means for supplying the fluid to the trapping solvent or collection liquid is a variable orifice pressure release restrictor with the orifice immersed in the collecting liquid. To this end, the orifice is located at the end of a long, thin probe. Because the supercritical fluid often carries entrained water and because the region of the orifice is cooled through fluid expansion, ice can form at the orifice and plug it. To prevent this from happening the metal walls around the orifice are heated. The probe, especially including the heated area, is insulated to decrease the heating effect on the cold collection fluid. The heat and insulation minimize the transfer of heat to the collection liquid while maintaining the orifice which is immersed in a cold solvent at the proper higher temperature to avoid freezing or internal deposition.

As can be understood from the above description, the supercritical extraction technique has several advantages, such as for example: (1) it automates the sample injection and fraction collection part of the extraction process as well as automating the extraction itself; (2) it allows the vials to be changed during the extraction process without depressurizing the extraction chamber; (3) it provides good trapping efficiency; (4) it provides low analyte/solvent losses; (5) it eliminates freezing and plugging of the restrictor while allowing the vial to be operated at a lower temperature to increase collection efficiency; (6) it reduces icing up of the outside of the vial; (7) it permits the conditions of the extraction, such as temperature and pressure, to be changed such as to remove certain substances from the sample matrix and deposit each substance in a separate vial; (8) it provides controllable operation and reproducible results; (9) it is also useful for investigating extraction kinetics by changing the vial during the extraction for examination; (10) it permits the use of different size vials because the stroke of a lift is no longer tied to the extraction cartridge elevator; and (11) it permits the use of multiple wash stations to clean the outside of the restrictor.

DESCRIPTION OF THE DRAWINGS

The above noted and other features of the invention will be better understood from the following detailed description when considered with reference to the accompanying drawings in which:

FIG. 7 is a schematic drawing of a supercritical fluid extraction system in accordance with an embodiment of the invention;

FIG. 8 is a fragmentary partly-schematic, partly-sectioned, broken away view of variable restrictor assembly in accordance with an embodiment of the invention;

FIG. 9 is a partly broken away, partly sectioned view of a variable restrictor forming a portion of the assembly of FIG. 8;

FIG. 10 is an enlarged fragmentary sectional view of the restrictor of FIG. 9;

FIG. 25 is a partially broken away, partially sectioned front view of an automatic variable restrictor having variable restrictor action through axial motion of a valve stem and self-cleaning action through rotary motion of the valve stem;

FIG. 26 is an enlarged, fragmentary, partially sectioned view of the orifice region of the restrictor of FIG. 25;

FIG. 27 is a top view of the restrictor of FIG. 25; and

DETAILED DESCRIPTION

Figure 1:
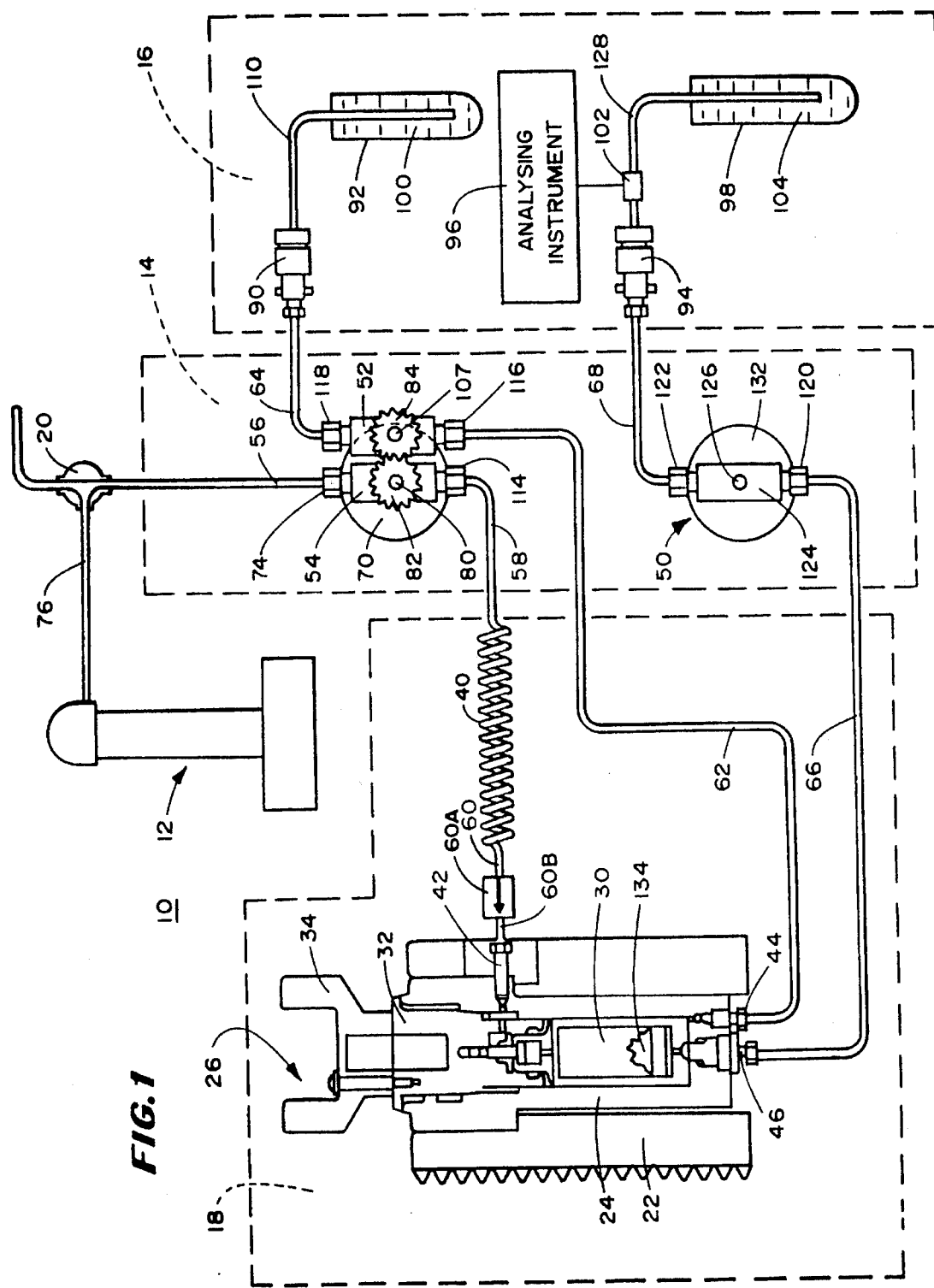
FIG. 1 is a schematic diagram illustrating the operation of a single supercritical fluid extraction system according to the invention.

In FIG. 1, there is shown a schematic fluidic diagram of one channel of a dual-channel supercritical fluid extraction system 10 having a pumping system 12, a valve system 14, a collector system 16 and a pressure vessel and fluid-extraction assembly 18. The pumping system 12 communicates with two extraction cartridges within the pressure vessel and fluid-extraction assembly 18 and for this purpose is connected through a tee joint 20 to two identical valve systems, one of which is shown at 14. Each valve system communicates with a different one of two inlets for the corresponding one of two extraction cartridges.

The valve system 14 and a second valve system (not shown in FIG. 1) which is connected to the other branch of the tee joint 20 are each connected to two different collector systems 16, one of which is shown in FIG. 1, and to different ones of the two extraction cartridges in the pressure-vessel and fluid-extraction assembly 18 so that, two extraction operations can be performed at the same time using the same pumping system 12.

With this arrangement, the valve system 14 causes: (1) supercritical fluid to flow from the pumping system 12 into a space between a cartridge and the interior of the pressure vessel of the pressure-vessel and fluid-extraction assembly 18 for purging the outside of the cartridge and the inside of the pressure vessel; and (2) applies supercritical fluid through the cartridge for extraction of a sample 134 therein. Because the fluid is applied both to the interior of the cartridge and the exterior, the cartridge does not have to withstand a high pressure difference between its interior and exterior and can be made economically.

In addition to controlling the flow of fluid into the pressure-vessel and fluid-extraction assembly 18, the valve system 14 controls the flow of: (1) purging supercritical fluid from the space between the cartridge and interior of the vessel to the collector system 16 or to a vent; and (2) the extractant from the interior of the cartridge to the collector system 16 for separate collection.

To hold sample 134 during an extraction process, the pressure-vessel and fluid-extraction assembly 18 includes a heating block 22, a pressure vessel 24 and a cartridge and plug assembly 26 with the cartridge and plug assembly 26 extending into the pressure vessel 24. The pressure vessel 24 fits within the heating block 22 for easy assembly and disassembly. With this arrangement, the heating block 22 maintains the fluids within the pressure-vessel and fluid-extraction assembly 18 at supercritical fluid temperature and pressure for proper extraction.

The cartridge and plug assembly 26 includes an extraction cartridge assembly 30, a breech plug 32 and a knob 34 which are connected together so that: (1) the pressure vessel 24 is easily sealed with the breech plug 32; (2) the extraction cartridge assembly 30 snaps onto the breech plug 32 and the assembly may be carried by the knob 34; and (3) the knob 34 serves as a handle to insert and fasten the assembly to the tube pressure vessel with the extraction tube communicating with an outlet aligned with its axis and an inlet for the space between the internal walls of the pressure vessel 24 and the exterior of the extraction cartridge 30 and for the interior of the extraction cartridge 30 being provided through a groove circumscribing the assembly inside the pressure vessel 24.

With this arrangement the extraction cartridge assembly 30 may be easily sealed in the pressure vessel 24 by threading the breech plug 32 into it and may be easily removed by unthreading the breech plug 32 and lifting the knob 34. The extraction cartridge assembly 30 contains a hollow interior, an inlet and an outlet so that a sample to be extracted may be placed in the hollow interior and supercritical fluid passed through the inlet, the hollow interior and to the outlet to a collector. The extraction cartridge assembly 30 serves as an extraction chamber or tube, the pressure vessel 24 serves as an extraction vessel and the heating block 22 serves as an oven as these terms are commonly used in the prior art.

The extraction cartridge assembly 30 has an opening which permits some supercritical fluid to enter the pressure vessel 24 to follow one path passing into the extraction tube and out through an outlet of the extraction tube into a conduit leading to a collector. Other supercritical fluid follows a second path around the outside of the cartridge to remove contaminants from the pressure vessel 24, equalize pressure and flow from another outlet. One of the inlet and outlet of the extraction cartridge assembly 30 enters along the central axis of the extraction cartridge assembly 30 and the other from the side to permit rotation of parts with respect to each other during seating of the pressure vessel 24 and yet permit communication of the extraction cartridge assembly 30 with the fluid source and with the collector.

The pressure vessel 24 is generally formed of strong material such as metal and is shaped as a container with an open top, an inlet opening and two outlet openings. The inlet opening is sized to receive an inlet fitting 42, the inlet fitting 42 being shown in FIG. 1 connected in series with check valve 60A to corresponding heat exchanger 40. Each of the two outlet openings are sized to receive a different one of a corresponding purge valve fitting 44, and a corresponding extractant fluid fitting 46. With these fittings, the pressure vessel 24 is able to receive the cartridge and plug assembly 26 in its open end and permit communication between the cartridge and the extractant fluid fittings, such as shown at 46. The inlet fittings, such as shown at 42, and purge valve fitting, such as 44, permit communication with the inside of the pressure vessel 24.

To control the flow of fluids to and from the pressure vessel and fluid-extraction assembly 18, the valve system 14 includes an extractant valve 50, a purge fluid valve 52 and an extracting fluid valve 54.

To introduce extracting fluid into the pressure-vessel and fluid-extraction assembly 18, the extracting fluid valve 54 communicates with one branch of the tee joint 20 through tube 56 and with one end of the heat exchanger 40 through tube 58, the other end of the heat exchanger 40 communicating with the inlet fitting 42 through tube 60, check valve 60A and tube 60B. With these connections, the extracting fluid valve 54 controls the flow of fluid from the pumping system 12 through the heat exchanger 40 and the pressure vessel 24 through the inlet fitting 42.

To remove purge fluid from the pressure vessel 24, the purge fluid valve 52 communicates at one port with the purge valve fitting 44 through tube 62 and with its other port through tube 64 (not shown in FIG. 1) with the collector system 16 or with a vent (not shown) to remove fluid containing contaminants from the exterior of fluid extraction cartridge assembly 30 and the interior of the pressure vessel 24.

To remove extractant from the extraction cartridge assembly 30, the extractant valve 50 communicates at one of its ports through tube 66 with the extractant fluid fitting 46 and through its other port with the collector system 16 through tube 68 for the collecting of the extracted material, sometimes referred to as analyte or extractant, from the sample within the pressure vessel and fluid-extraction assembly 18.

For convenience, the valves 52 and 54 are mounted to be operated by a single manual control knob 70. To supply fluid to the valve system 14: (1) the tube 56 carries pressurized fluid from the pumping system 12 to tee joint 20; (2) tube 76 is connected to one arm of tee joint 20 to carry pressurized fluid to another liquid extraction system unit not shown on FIG. 1; and (3) the remaining arm of the tee joint 20 is connected through the tube 56 to an inlet fitting 74 of extracting fluid valve 54.

The extracting fluid valve 54 has a rotary control shaft 80 that is rotated to open and close its internal port. This shaft is operated by hand control knob 70 and carries spur gear 82 pinned to the control shaft 80. Spur gear 84, which is pinned to control shaft 107 of purge fluid valve 52, meshes with spur gear 82 so that when control knob 70 is rotated clockwise, extracting fluid valve 54 is closed, but since the control shaft 107 of purge fluid valve 52 is geared to turn in the opposite direction, the clockwise rotation of knob 70 opens purge fluid valve 52.

The extractant valve 50 includes an inlet fitting 120, outlet fitting 122, manual control knob 132 and control shaft 126. The rotary control shaft 126 is attached to control knob 132. When the extractant valve 50 is opened by turning the control knob 132 counterclockwise from its closed position, fluid flows from the extraction cartridge assembly 30, through the extractant fluid fitting 46, the conduit 66, the valve inlet fitting 120, the outlet fitting 122, through the tube 68 and into the collector system 16.

The collector system 16 includes a purge coupling 90, a purge fluid collector 92, an extractant coupling 94, an analyzing instrument 96, and an extractant fluid collector 98. The purge fluid flowing through the valve 52, flows through purge coupling 90 into the capillary tube 110 and from there into the purge fluid collector 92 where it flows into a solvent 100. Similarly, the extractant flowing through valve 50 flows through tube 68 to the extractant coupling 94 and from there to the capillary tube 128 and extractant fluid collector 98 which contains an appropriate solvent 104 in the preferred embodiment.

The analyzing instrument 96 may be coupled to the capillary tube 128 through an optical coupling 102 in a manner known in the art. The optical coupling 102 is a photodetector and light source on opposite sides of a portion of the capillary tube 128, which portion has been modified to pass light. This instrument 96 monitors extractant and may provide an indication of its passing into the extractant fluid collector 98 and information about its light absorbance. Other analytical instruments may also be used to identify or indicate other characteristics of the extractant.

Figure 2:
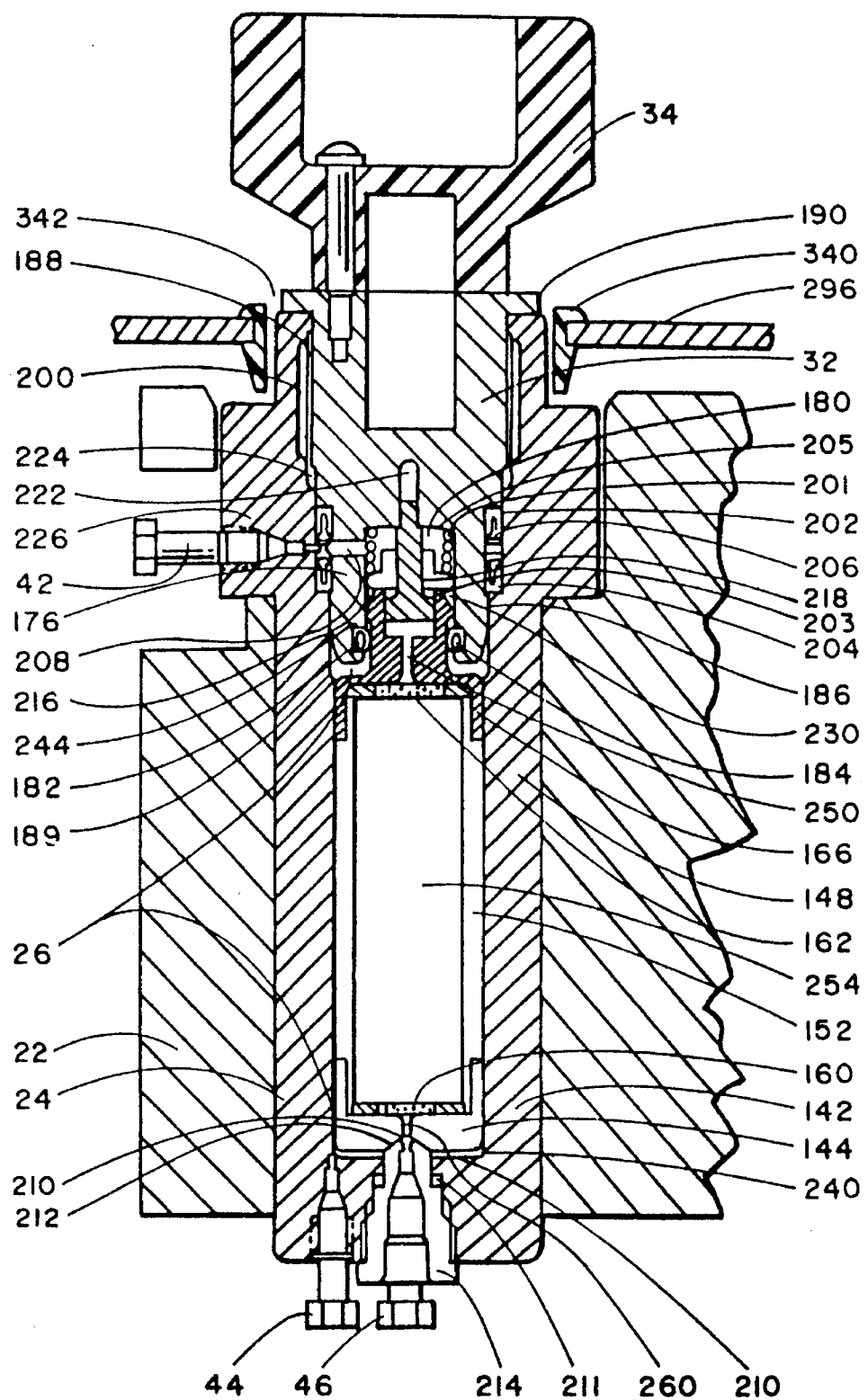
FIG. 2 is a fragmentary sectional view of the extraction cartridge, breech plug pressure vessel and heating block.

In FIG. 2, there is shown a sectional view of the clipped-together extraction cartridge 26, knob 34 and breech plug 32 replaceably installed in pressure vessel 24 which in turn has previously been permanently force fit into heating block 22.

The passageway 208 extends radially from the recess 180 in the breech plug 32 to a torroidal inlet channel, it provides an open path for fluid between the two regardless of the orientation of passageway 208. The passageway 208 opens at an uncontrolled angular location with respect to the inlet fixture 42 (inner side). Fluid flows from one side of the inwardly curved portion of an hour glass shaped spacer 206 that communicates with the outlet of fitting 42 to the other side of the inwardly curved portion and from there to the passageway 208.

When the cartridge and plug assembly 26 are inserted into the pressure vessel 24 as shown in FIG. 2, the knob 34 is rotated screwing the breech plug 32 and attached cartridge and plug assembly 26 down into the pressure vessel 24. When conical recess 210 in the bottom cap 144 reaches the external conical tip 212 of fitting adapter 214, the cartridge and plug assembly 26 is prevented from moving further down.

Screwing the breech plug 32 in further after the cartridge and plug assembly 26 has bottomed causes the upper flat annular surface of fitting nipple 176 to bear upon the flat lower surface of a hat-shaped washer 216. At this time, the hat-shaped washer 216 is residing against the upper surface of the head of a shoulder screw 218 which is threaded into cylindrical hole 222 in breech plug 32.

Further screwing of the breech plug 32 into the pressure vessel 24 causes the nipple 176 to lift the washer 216 off of the screw head and compress a coil spring 201 between annular surface 205 and the ridge of the washer 216. Continued screwing of the breech plug 32 into the pressure vessel 24 causes annular flange 190 of breech plug 32 to bear upon the upper surface of the pressure vessel 24. This provides a limit stop with the coil spring 201 compressed, as shown in FIG. 2.

The force of the compression spring 201 is enough to provide a low pressure seal between the hat-shaped washer 216 and the upper annular surface 203 of the fitting nipple 176. More importantly, this force also provides a low pressure seal on the mating concical surfaces of the recess 210 of lower cap 144 and the external conical tip 212 of the fitting adapter 214.

The maximum rated operating pressure of the embodiment shown in FIG. 2 is 10,000 psi. The maximum operating temperature is 150 degrees Centigrade. The equipment need not be designed for operating temperatures above 300 degrees Centigrade and pressure above 30,000 pounds per square inch.

After the breech plug 32 and the cartridge and plug assembly 26 are assembled into the pressure vessel 24 as described above, but before an extraction, the space between the cartridge and plug assembly 26 and the pressure vessel 24 is purged of contaminants. During such a purge or cleaning cycle supercritical fluid enters fluid inlet 42, is distributed by the annular spacer 206 and goes through passageway 208. It passes between the outer diameter of hat-shaped washer 216 and the inside cylindrical diameter 230 of the recess within breech plug 32. Fluid then continues down and passes the annular space between the outside diameter of engaging nipple 176 and inside diameter 230 of the recess 180 in breech plug 32. The fluid passes garter spring 184 and circulates with even circumferential distribution around the outside of top cap 148, the extraction tube 152, and the bottom cap 144. The flow is collected in the annular space below the bottom cap 144 and above the bottom 240 of pressure vessel 24 and exits through vent discharge fitting 44, carrying contaminants with it.

Figure 3:
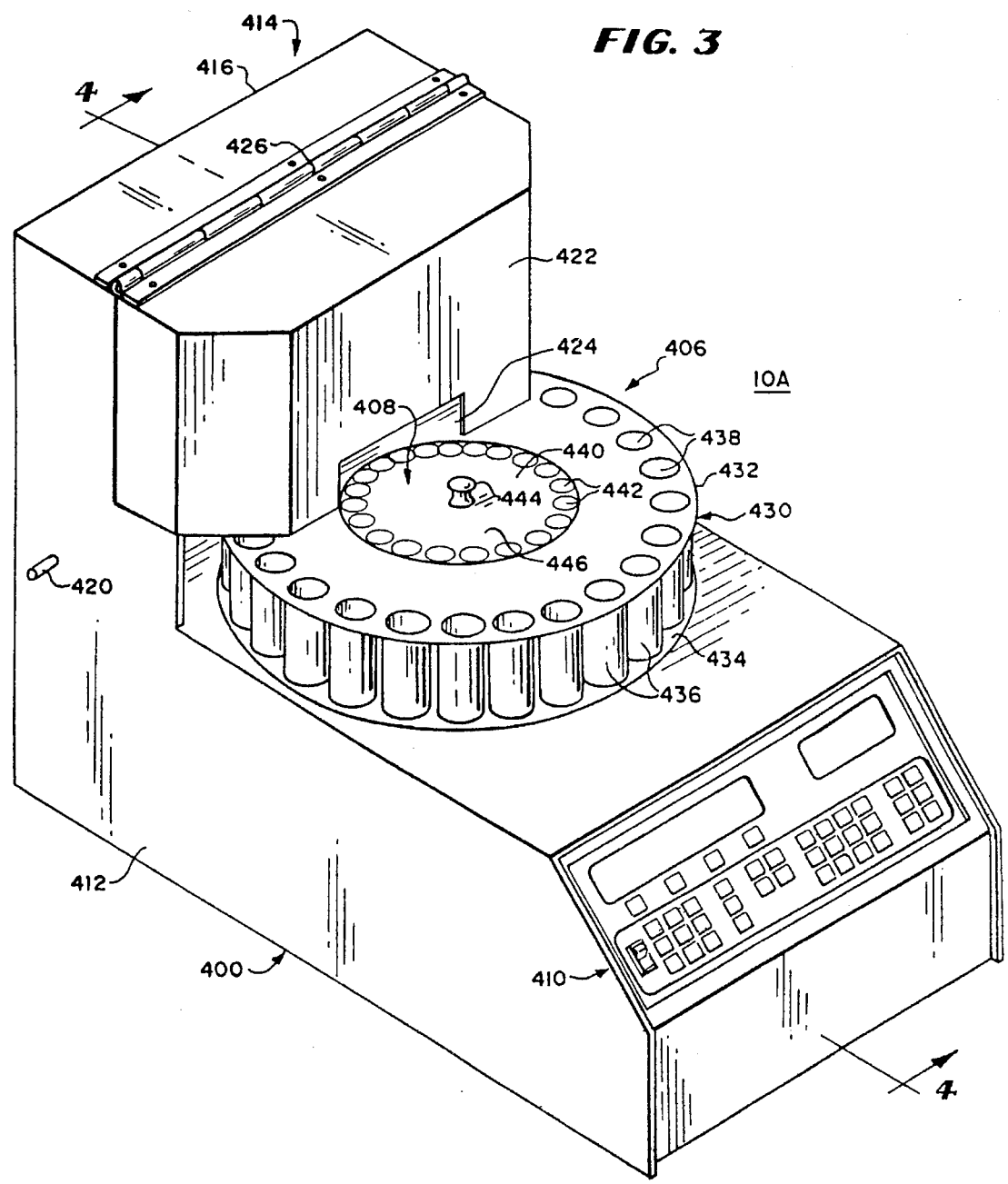
FIG. 3 is a perspective view of another embodiment of the invention capable of automatic extraction of a series of samples.

For extraction, supercritical fluid entering fitting 42 is distributed in the space occupied by spacer ring 206, flows through passageway 208 and flows down the few thousandths of an inch radial gap between the shoulder of shoulder screw 218 and the inside diameter of washer 216. The fluid continues to flow down and flows through passageway 250, porous frit 162 and into extraction volume 254 where it passes through material to be extracted. Extraction volume 254 is shown sized in FIG. 2 for a 10 cubic centimeter volume to receive sample. After passing the extraction volume fluid, it is exhausted for sample collection through frit 160, passageway 260, fitting adapter 214 and out through fitting 46. The operation of the embodiment of FIGS. 1 and 2 is more fully explained in U.S. Pat. No. 5,094,753, the disclosure of which is incorporated herein by reference. In FIG. 3, there is shown a simplified perspective view of another embodiment 10A of supercritical fluid extraction system having a cabinet 400 containing a drive section in its lower portion (not shown in FIG. 3), an extraction section in the upper portion of the cabinet (not shown in FIG. 3), a sample injection section 406 and a fraction collection section 408. The supercritical liquid extraction system 10A is controlled from a panel 410 on the front of the cabinet 400 and the drive section operates the extraction section, the sample injection section 406, and the fraction collection section 408, which cooperate together to extract a plurality of samples sequentially and collect the extractant from the samples in separate containers with minimum intervention by an operator.

The supercritical fluid extraction system in the embodiment 10A operates in a manner similar to that of the embodiment of FIG. 1 but is adapted to cooperate with the novel sample injector and fraction collector. With this arrangement, a series of samples to be extracted are preloaded into a means for holding the samples and the samples are automatically injected one at a time into the extractor. In the extractor, supercritical fluid is supplied to the samples and an extractant is removed from the samples one by one. To aid in correlating the embodiment 10 (FIG. 2) and the embodiment 10A (FIG. 3), similar parts have the same reference numerals but in the embodiment of FIGS. 3, 4, 5 and 6, the numerals include the suffix "A".

The extractant is supplied to individual containers or individual compartments of one container in a fraction collector. Thus, a plurality of extractions are performed on a plurality of different preloaded samples without the need for manually loading samples or initiating the flow of the supercritical fluid for each individual sample. The samples are automatically mechanically moved one by one into the extractor for extraction instead of being individually physically injected by an operator.

The cabinet 400 has a lower portion 412 generally shaped as a right regular parallelopiped with an angled control panel 410 and upstanding upper portion 414 which is another right regular parallelopiped extending upwardly to create a profile substantially shaped as an "L" having a common back portion or rear panel 416 which may contain fans and connections for supplementary pumps and the like. A fluid fitting 420 extends from one side to permit liquid or near supercritical fluids to be introduced into the cabinet 400. The L-profiled cabinet 400 has an angled front panel 410 for convenient use of controls and a top surface on the foot of the "L" for manipulation of samples to be injected and extractants that are collected.

To permit access to the interior of the cabinet 400, the upper portion 414 includes a hinged front access panel 422 having hinges 426 at its top so that it can be pivoted upwardly. It includes an opening 424 near its bottom to permit the entrance of fraction collector receptacles that are relatively tall. It extends downwardly to a point spaced from the top surface of the lower portion 412 of the cabinet 400 a sufficient distance to permit the entrance of normal receptacles used in the sample injector and the fraction collector.

The sample injection section 406 includes a sample reel 430 which is formed of upper and lower rotatable plates 432 and 434 spaced vertically from each other and containing holes in the upper plate 432 and openings in the lower plate 434 which receive cylindrical tubular sleeves 436 having vertical longitudinal axes and open ends. The upper open end 438 permits samples to be received and to be removed as the sample reel 430 is rotated into the extractor.

With this arrangement, the sample reel 430 may be rotated to move samples one by one into the extractor for processing. The sample reel 430 is horizontal and extends into the upper portion 414 of the cabinet 400 and into the extractor assembly with its vertical center of rotation being outside of the upper portion 414 to permit ready access to a number of the sleeves 436 by users and yet to permit sequential rotation by automatic means into the extractor. In the preferred embodiment, there are 24 sleeves for containing 24 distinctly different samples which can, without human intervention, be moved into the extractor.

To receive extractant, the fraction collection section 408 includes a horizontal fraction collector reel 440 mounted concentrically with the sample reel 430 but having a smaller diameter to be inside the sample reel 430 having a plurality of openings 442 circularly arranged in spaced apart relationship with each other about the periphery of a top plate 446 of the fraction collector reel 440 and having in its center a knob 444 by which the fraction collector reel 440 may be lifted and removed from the cabinet 400. With this arrangement, the fraction collector reel 440 may be lifted and removed or reinserted after the hinged access panel 422 is pivoted upwardly about the hinges 426.

When the fraction collector reel 440 is in place, it is rotated automatically through the opening 424 into a location in which one or more individual containers 442 may receive extractant. The fraction collector reel 440 is moved alternately with the sample reel 430 and independently of it so that, after a sample injection and extraction, one or more of the openings 442 are moved into position to receive the extractant prior to the injection of another sample for extraction.

Because the reels 430 and 440 rotate within the upper portion 414 of the cabinet 400 with a portion of its periphery outside of the cabinet 400, the collected extractant may be removed and new sample added during operation of the equipment. For this purpose, the receptacles for the fractions and the receptacles for the samples have upward open ends and are mounted with their axes vertical.

Figure 4:
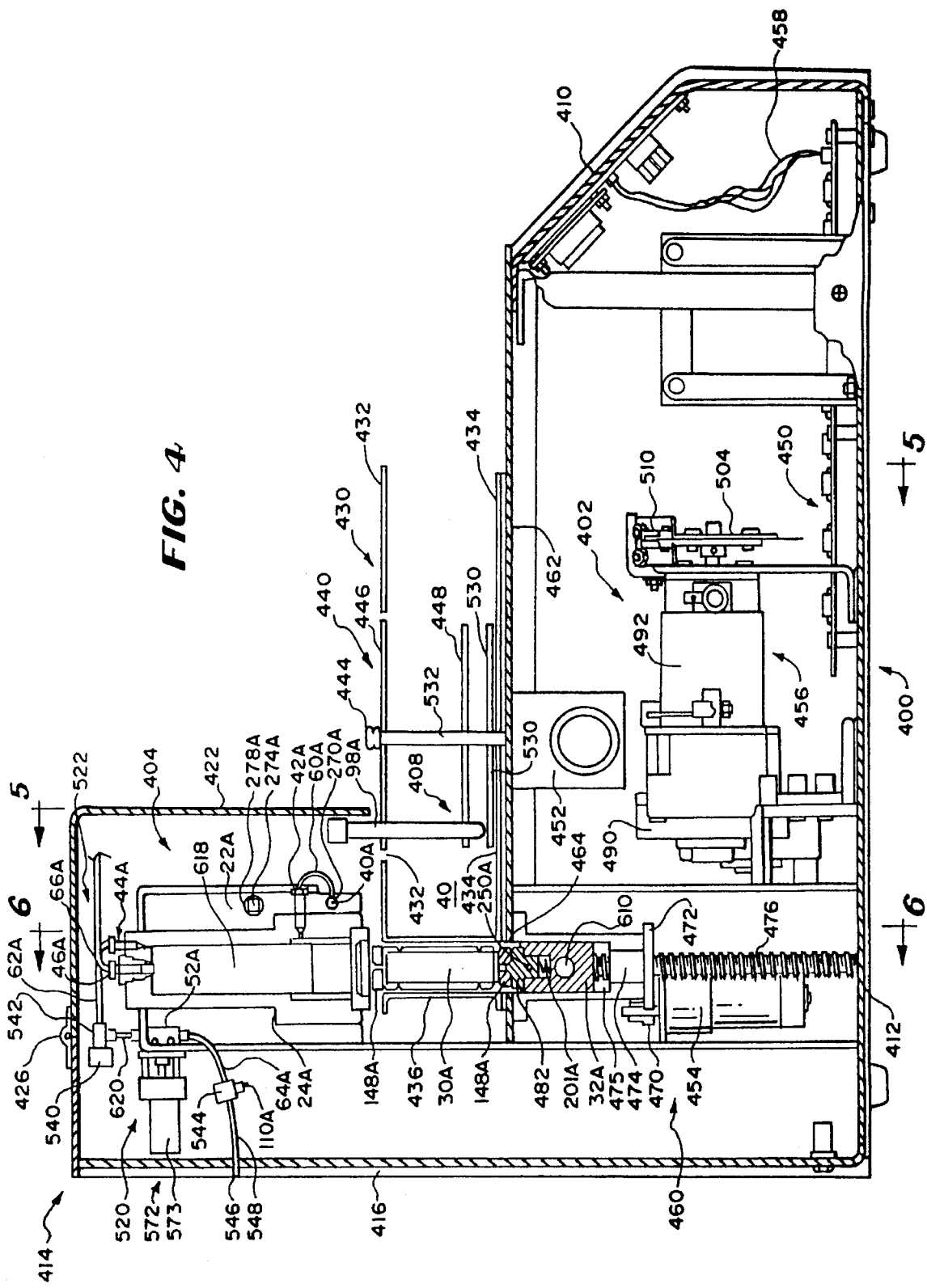
FIG. 4 is a sectional view taken through lines 4—4 of FIG. 3.

In FIG. 4, there is shown a longitudinal sectional view through lines 4—4 of FIG. 3 showing the cabinet 400, the drive section 402 within the cabinet 400, the extraction section 404, the sample injection section 406 and the fraction collection section 408. The drive section 402 includes a control system 450, a sample-and-extractant container reel drive assembly 452, a sample injector drive 454 and a fluid drive or pump 456. The control system 450 receives information from the control panel 410 and conveys information to it through a cable 458. It also controls the pump 456, the sample-and-extractant trap container reel drive assembly 452 and the sample injector drive 454, which cooperate together to move samples into position, inject them into the extractor, pump fluids through the extractor to extract the samples and collect the samples in sequence one by one.

To inject samples into the extraction section 404, the sample injection section 406 includes the sample-and-extractant container reel drive assembly 452, the sample reel assembly 430, and a cartridge injector assembly 460. The sample-and-extractant container reel drive assembly 452 drives the sample reel assembly 430 to carry a cartridge assembly 30A onto the cartridge injector assembly 460 which lifts it under the control of the sample injector drive 454 upwardly into a pressure vessel 24A for the purpose of extracting a sample within the cartridge assembly 30A. The cartridge assembly 30A and the pressure vessel 24A are similar to the cartridge assembly 30 and pressure vessel 24 of the embodiment of FIGS. 1 and 2 and are only adapted such as by having their top and bottom sides reversed to permit the cartridge assembly 30A to be inserted from the bottom into the pressure vessel 24A and be more easily sealed therein for extraction and removed by gravity after extraction.

To drive the sample reel assembly 430, the sample-and-extractant container reel drive assembly 452 includes a central transmission and motors on each side that drive the transmission under the control of the control system 450 to drive either one or both the sample injector reel assembly 430 and the fraction collector reel 440.

The sample injector reel assembly 430 includes the top plate 432, the bottom plate 434, both of which are rotatable together to carry a plurality of sleeves 436 sequentially, one at a time, into position for the repeated injecting of cartridges one by one into the pressure vessel 24A and the removal of the cartridges from the pressure vessel 24A and the return of them to the reel assembly 430 one by one so that only one cartridge is in the pressure vessel 24A at a time.

Within the extraction section 404, a stationary bottom plate 462 has a hole 464, with the hole being aligned with the open-bottom end of the pressure vessel 24A and the upper end of the cartridge injector assembly 460. Consequently, the cartridge assemblies such as 30A are rotated one by one above the open end 464 in the bottom plate 462 for movement upwardly into the pressure vessel assembly 24A by the cartridge injector assembly 460 under the control of the sample injector drive 454 for extraction of the sample therein. With this arrangement, a stationary plate 462 holds the cartridge assemblies 30A in place as they are rotated by the upper and lower plates 432 and 434 until they are sequentially brought over the opening 464 through the stationary plate 462 for elevation into the pressure vessel 24A.

To inject cartridges into the pressure vessel 24A, the cartridge injector assembly 460 includes the sample injector drive 454, a pinion 470, a gear 472, a multi-threaded, fast action nut 474, a corresponding screw 476, and piston or plug 32A. The pinion 470 is mounted to the output shaft of the drive gear motor 454 and engages the teeth of gear 472. The gear 472 is fastened to or integrally formed with the drive nut 474 which, as it rotates, moves the screw 476 upwardly or downwardly. The support platform 475, piston or plug 32A and sample container 30A are carried by the top of the screw 476 and are moved upwardly and downwardly. The top surface of the plug 32A, which is supported by the screw 476 in its lower position is flush with the bottom of the opening 464 in the fixed plate 462 to support a cartridge such as 30A therein and in its top position positions the piston or plug 32A at the bottom of the pressure vessel 24A. Plug 32A carries self-actuated, spring-biased, cylinder seals, such as those made by the Bal-Seal Corporation. These seals provide a high pressure fluid-tight seal between the plug 32A and the inner wall of the pressure vessel 24A.

With this arrangement, the piston or plug 32A is sealable against the walls of the pressure vessel 24A during the extraction process after moving the cartridge assembly 30A upwardly into the pressure vessel 24A, and after extraction, can move the cartridge assembly 30A downwardly back to the sample reel assembly 430 for rotation out of the upper injector housing 414 as a new cartridge is moved into position for injecting into the pressure vessel 24A. A bearing mount rotatably supports the nut 474 while maintaining it in the same vertical position to move the rapid-advance screw or other screw 476 upwardly and downwardly.

The plug 32A serves a function similar to the breech plug 32 in the embodiment of FIGS. 1–2 and contains within it an opening supporting a spring 201A and a support block 482 so that the support block 482 is biased inwardly against the cartridge end 148A to move the cartridge 30A into place against fittings for supercritical fluid.

To extract the sample in the cartridge 30A after it has been moved into position and the breech plug 32A fastened in place for a seal, extracting fluid is applied through the fitting 42A in a manner similar to the embodiment of FIG. 1, so that the extracting fluid flows through one path into the cartridge 30A and through another path over the outside of the cartridge 30A into the fitting 44A and from there to a purge collector or vent. The extractant, after passing through the cartridge and the sample, exits from a fitting 46A and proceeds to the sample collector in a manner to be described hereinafter.

To pump fluid such as carbon dioxide into the pressure vessel 24A at a temperature proper for supercritical extraction: (1) the pump 456 includes a pump head 490 and an electrical motor 492; and (2) the pressure vessel 24A has an aluminum heating block 22A over it, an opening 278A in the aluminum heating block, a rod-shaped heating element 274A in the aperture 278A, the extracting fluid fitting 42A and a heat exchanger 40A entering the aluminum heating block 22A at aperture 270A. The motor 492 drives the pump mechanism 490 to pump fluid into the aperture 270A, through the heat exchanger 40A within the aperture 270A, through the connecting tubing 60A and the fitting 42A and into the cartridge 30A and the pressure vessel 24A. The aluminum block 22A controls the temperature of the fluid, which may be carbon dioxide or any other useful extracting fluid to keep it above the supercritical temperature for that fluid, and for that purpose, the heating rod 274A within the aperature 278A is used when necessary to heat the aluminum block 22A.

To collect extractants, the fraction collector section 408 includes the fraction collection reel 440, the sample-andextractant container reel drive assembly 452, a purge fluid outlet system 520 and an extractant fluid outlet system 522. The fraction collection reel 440 moves receptacles such as 98A into position within the housing 414 where the extractant fluid outlet system, 522 to be described in greater detail hereinafter, causes fluid from the fitting 46A in the pressure vessel 24A to flow outwardly and into the receptacle 98A after piercing a seal therein. The purge fluid system 520 causes purge fluid to flow from the purge fluid fitting 44A to a pressure control unit and finally to an exhaust or collection unit.

To move the collection receptacles 98A into position, the fraction collection reel 440 includes a knob 444, an intermediate plate 448, an upper plate 446, a lower disk plate 530 and a drive rod 532. The drive rod 532 rotates within the fixed disk 530 and carries above them the upper and lower plates 446 and 448. The upper and lower plates 446 and 448 have aligned circumferentially spaced holes through them, each of which can receive a collection vial such as 98A. The lower disk 530 does not have holes and supports the plates as they are moved. The knob 444 may be used to lift the fraction collector reel 440 from the center of the sample injector reel 430 after the hinged front access panel 422 has been opened about its hinge 426.

The sample-and-extractant container reel drive assembly 452 moves the collection vials one by one inside the upper portion of the housing 414 to receive extractant. One or more such vessels 98A may be moved in place each time a sample cartridge 30A is extracted so that the receptacles 98A are moved alternatively with the sample cartridges 30A, although several receptacles 98A may be moved in the time between moving one of the sample cartridges 30A into a pressure vessel 24A and the time the sample cartridge is removed from the pressure vessel 24A. The extractant passes through fitting 46A and into the fraction collector receptacles 98A in a manner to be described hereinafter.

The purge fitting 44A communicates with the extraction volume in the cartridge 30A and is connected to a Tee-joint tube 542 through tubing 62A. A second arm of the Tee-joint tube 542 is connected to an over-pressure safety diaphram 540 calibrated to burst at 15,000 pounds per square inch. This is an excess of the maximum rated working pressure of 10,000 pounds per square inch for pressure vessel 24A. The remaining arm of the Tee-joint tube 542 is connected to the purge valve 52A. The other side of the purge valve 52A is connected to the first side of a second Tee-joint tube 544 through the tube 64A. The second side of the Tee-joint tube 544 is connected to an exterior vent port 546 through a tube 548. The third arm of the Tee-joint tube 544 is connected to the exhaust tube 110A which vents the fraction collection vial 98A. With this arrangement, the purge fluid flowing through fitting 44A is removed and a tube connected to the vent port 546 is also used to vent the sample receptacle 98A in a manner to be described hereinafter.

Figure 5:
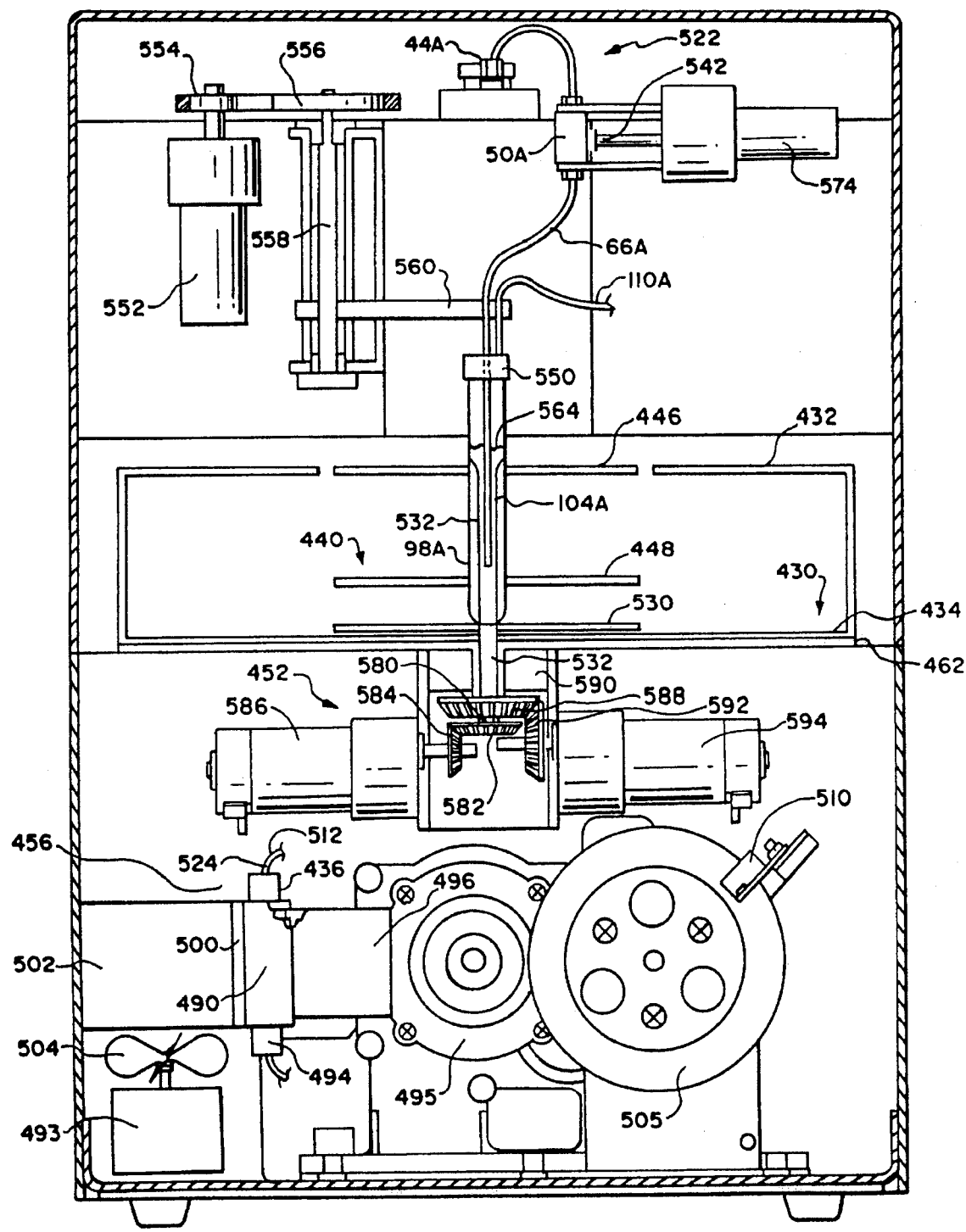
FIG. 5 is a sectional view taken through lines 5—5 of FIG. 4.

In FIG. 5, there is shown a simplified sectional elevational view of the embodiment 10A of supercritical fluid extractor taken through lines 55—of FIG. 4 having the sample-and-extractant container reel drive assembly 452, the pump 456 and the extractant fluid outlet system 522. The sample-and-extractant container reel drive assembly 452 may selectively move either the sample reel 430 or the fraction collection reel 440 under the control of the controller 450 (FIG. 4).

To selectively drive the fraction collection reel 440, the sample-and-extractant container reel drive assembly 452 includes a fraction collection spindle 532, a tubular shaft 580, a bevel gear 582, a bevel gear 584 and a gear motor 586.

The controller 450 controls the gear motor 586 to rotate the fraction collection reel 440. For this purpose, the spindle 532 is held by the tubular shaft 580. The bevel gear 582 is fastened at the end of the spindle 532 and meshes with the bevel gear 584 on gear motor 586. The controller 450 moves these gears into meshing position and causes the motor 586 to rotate its output shaft so as to drive the collection reel 440 (FIGS. 3 and 4) and not the sample injector reel 430.

To move the sample injector reel 430, the sample-and-extractant container reel drive assembly 452 includes the tubular shaft 580 supported by bearing block 590, fraction collection spindle 532, bevel gear 588, bevel gear 592 and gear motor 594. The controller 450 actuates gear motor 594 to cause the bevel gear 592 to rotate. The bevel gear 592 meshes with the bevel gear 588 which is attached to the bottom end of the fraction collection spindle 532.

To cause extractant to flow into the fraction collection vial 98A, the extractant fluid outlet system 522 includes a gear motor 552, a pinion 554, a gear 556, a lead screw 558, an arm 560, and a restrictor tube 66A. The vials 98A have a seal 550 over the top, which seal can be pierced. To cause the seal 550 to be pierced and extractant to flow into the vial 98A, the controller 450 starts the gear motor 552 which rotates its pinion 554 which is in engagement with the gear 556. The pinion 554 rotates the gear 556, which engages and is fastened to the rotating lead screw 558. The arm 560 is mounted for movement by the lead screw 558 and lowers it into a position where the restrictor tube 66A pierces the cap 550 on the collection vial 98A and moves its tip below the surface 564 of the collection fluid within the vial 98A. As the extractant flows into the tube, exhaust is removed from the tube through an exhaust tube 110A (FIG. 4 in addition to FIG. 5).

Extractant flows through the fitting 46A (FIG. 4) from the sample cartridge 30A (FIG. 4) through the tubing 522 (FIG. 4), the valve 50A and the restrictor tube 66A. Extractant residing in bubbles from the tube are captured through trapping fluid 104A whereby extractant is trapped in the trapping fluid 104 in the vial 98A and extracting fluid passes out through the exhaust tube 110A, Tee-joint tube 544 (FIG. 4), tube 66A and exhaust port 546 (FIG. 4). After collection of the extractant, the motor 552 moves in the reverse direction and raises arm 560 which removes the restrictor tube 66A and exhaust tube 110A from the vial 98A.

Figure 6:
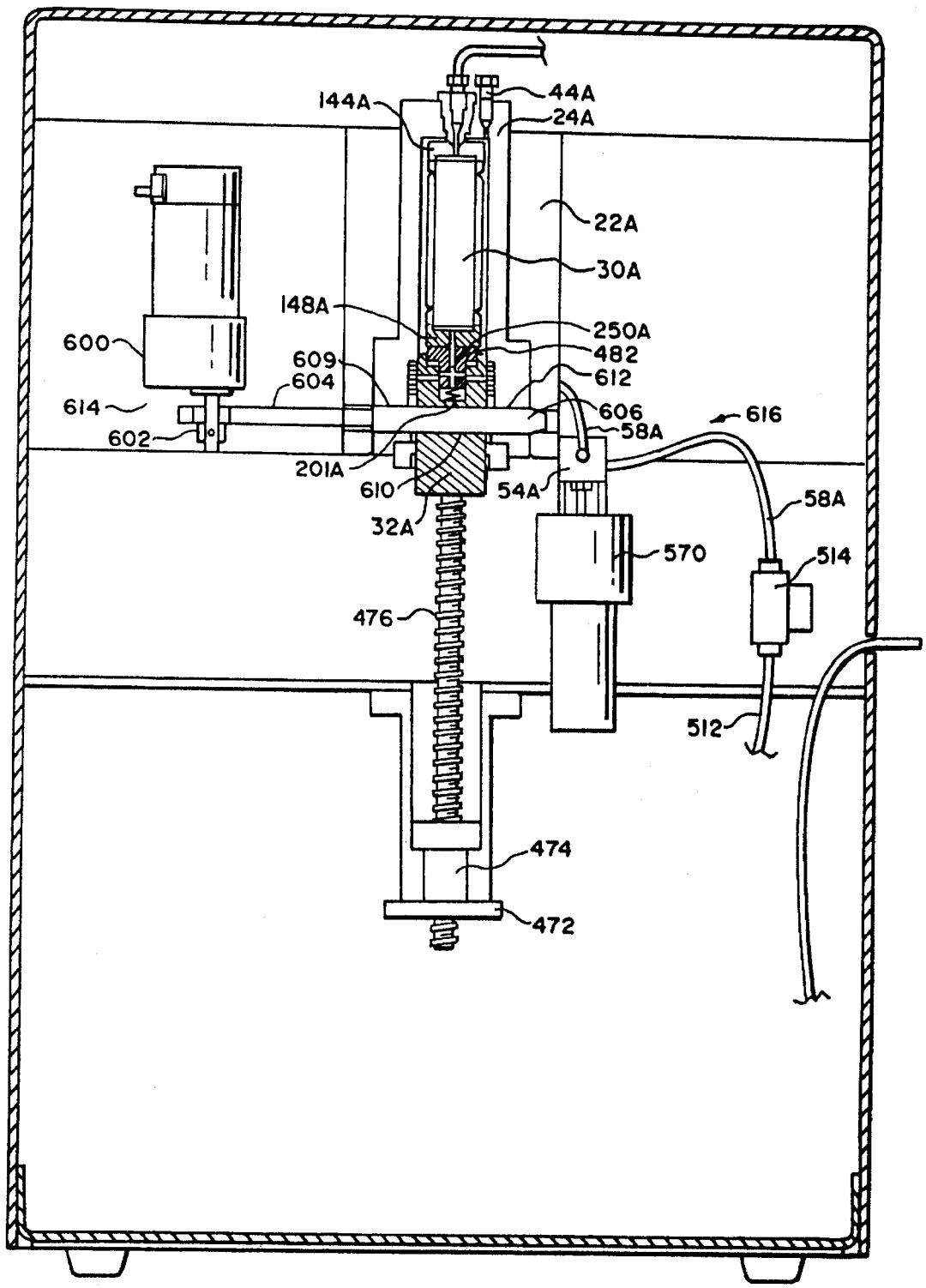
FIG. 6 is a sectional view taken through lines 6—6 of FIG. 4.

In FIG. 6, there is shown a sectional view, partly simplified, taken through lines 6—6 of FIG. 4 having a locking mechanism 614 for locking plug 32A into the pressure vessel 24A and a control mechanism 616 for controlling the extraction fluid. As best shown in this view, the locking mechanism 614 includes a gear motor 600, a pinion 602, a rack 604, a locking pin 606, a hole 609 in the pressure vessel 24A and a hole 610 in the piston or end piece or breach plug 32A and a hole 612 through the other side of the pressure vessel 24A.

Instead of a pin 606, a yoke of the type conventionally used as a Winchester 94 rifle locking mechanism advantageously may be used. This type of locking mechanism is a yoke mounted to a pinion 602 and rack 604 as shown in FIG. 6. In this mechanism, a plate with a slot cut out of it to form a yoke is moved by the rack and pinion to pass under the plug 32A to hold it against pressure and provide strong support therewith by further engaging slots in the pressure vessel 24A. The aforementioned slot in the plate provides clearance for the screw 476.

The embodiment of FIGS. 3–6 are more fully described in U.S. Pat. No. 5,160,624, the disclosure of which is incorporated herein by reference.

In FIG. 7, there is shown a supercritical fluid extraction system 10 having a pumping system 12, a supercritical fluid extractor 13, a pressure transducer 15, a variable restrictor system 11 and collection system 19. The pumping system 12 pumps supercritical fluid through the fluid extractor 13 where it dissolves sample. The sample and supercritical fluid then flows from the fluid extractor 13 through the conduit 31 where it influences the pressure transducer 15 to indicate pressure on electrical conductors 47 and to the variable flow restriction system 11 into the collection system 19.

To pump supercritical fluid, the pumping system 12 includes a pump 23 and a pump controller 25 connected to the extractor 13 through the tubing 27. Clean, supercritical extraction grade $CO_2$ enters a conventional syringe pump 23 and is pressurized to supercritical pressures. A suitable pump controller 25, monitors and controls the pressure developed in the pump. The controller 25 and pump provide for measurement of fluid pressure and fluid flow rate. The controller also provides a pressure set point and pressure controller for constant pressure operation and a flow set point and flow controller for constant flow operation.

The analytical sample is within an extraction chamber inside the extractor 13 under plug 29, and the supercritical fluid extracts the analytes from the sample. The extraction chamber has a fluid inlet for extraction fluid to extract the sample and an outlet for fluid with extracted analyte in solution.

To receive the analyte, the collection system 19 includes a tube 34, an orifice tip 39 at the end of the tube 34, a collection vessel 37, collection solvent 35 within the collection vessel 37, a pierceable septum 41 and a vent tube 43. The supercritical fluid with dissolved analytes flows from the outlet of the extractor through tubing 31 to pressure transducer 15 and then to the variable restriction system 11 through transfer tubing 33. If the transfer tubing 31, transducer 15, tubing 33 and restrictor 11 are not heated, the supercritical fluid may cool to a liquid before reaching the orifice tip 39. This is often of no consequence as the liquid may satisfactorily solvate the analyte and the orifice tip serves to depressurize either supercritical fluid or liquid.

The orifice tip 39 of the variable restriction system is immersed in the collection solvent 35 in a collection container 37. The rate at which the supercritical fluid is discharged into the collection fluid is set by control knob 17 on the variable restriction system 11. At the discharge orifice 39 of the variable restriction system 11, the supercritical fluid or liquid expands into a gas and bubbles through the collection solvent 35, depositing the extracted analyte in the collection solvent.

To insure that as much as possible of the analyte is deposited in the collection solvent 35 or collection container, the supercritical pressure conditions are maintained all of the way down to the orifice tip 39. The collecting tube has a pierceable septum 41 covering its mouth. The septum is pierced by the probe of variable restrictor 11 and by vent tube 43. The vent tube may be led to a fume hood (not shown) in case the gas issuing from it is toxic or flammable. Conductors 47 receive pressure representing electrical signals from the transducer, which signals are used to control pressure as explained hereinafter.

In FIG. 8, there is shown a partly-schematic, partly-sectioned view of a manually-controlled variable-valve restrictor assembly 11 having a valve adjustment section 1013, a temperature control section 1015 and a needle valve section 1011. The needle valve section 1011 is: (1) adjusted as to orifice opening size by the valve adjustment section 1013 to which it is connected to control the pressure in the pressure chamber or column by controlling the release of fluid; and (2) is positioned to provide the effluent directly into a collection chamber environment to avoid loss of sample and the use of time in removing sample from tubing. The temperature control section 1015 controls the temperature of the effluent at the orifice to avoid undesired cooling.

As shown in FIG. 8, the restrictor valve is of the needle valve type and the needle valve section includes a metering restriction orifice or expansion area 1248, a control needle 1256, a control needle tip 1257, a barrel tube 1234, a barrel tube tip 1233, a fluid-passing orifice 1240 and a fluid connection hole 1287. The control needle 1256 cooperates with the hole 1287 to carry the flow of effluent into the needle valve where it is received in a space between the barrel tube 1234 and control needle 1256 that leads to the expansion area 1248. At the expansion area 1248, the barrel tube tip 1233 and control needle tip 1257 cooperate to control the expansion and release of the effluent through the fluid-passing orifice 1240 directly into the collection environment.

To permit fluid flow to the clearance area, there are a connecting annular clearance between control needle 1256 and hole 1287 and an annular clearance between the inside diameter of barrel tube 1234 and the coaxial needle 1256. These provide clearance for fluid flow from the fitting 1282 down to the metering, restriction, or expansion area 1248 of the valve where the pressure drop takes place. For this purpose, the control needle tip 1257 rotates and reciprocates within the barrel tube 1233 varying the size of the fluid-passing orifice at expansion area 1248. The point angle of the needle tip 1257 is more acute than that of the female seat in the barrel tip 1233, making the narrowest portion of the orifice at the far distal surface of the tip at 1240.

The expansion of the supercritical fluid occurs essentially at the discharge opening 1240 of the tip 1233, 1257, making the extent of conduit exposed to expanded extraction fluid almost without length, so the expansion occurs in contact with the collection solvent, and the analyte precipitates from the extraction fluid directly into the collection solvent or other collecting trap. This improves collection efficiency and decreases plugging at the orifice.

Supercritical pressure is maintained down to the orifice or restriction region 1240 of the distal end of the barrel tip, which is inserted into the midst of a collection solvent or other collection trap. The distance between point of the needle tip 1257 and the recessed seat in the barrel tip forms a variable orifice at 1240 which controls the flow rate.

To adjust the pressure and flow rate at the variable orifice 1240, the adjustment section 1013 includes an adjustment knob 1266, a control needle head 1265, male and female screw threads 1264, and an actuation nut 1268. The needle is adjusted using knob 1266 which is fastened to the control needle head 1265 for rotation therewith. The upper end of the needle 1256 is silver soldered into a recess in the underside of control needle head 1265 for rotation and reciprocation with the control needle head and adjustment knob 1266 and head 1256 within the control actuation nut 1268. The control actuation nut includes internal threads that cooperate with the external threads on the control needle head.

With this arrangement, rotating the knob 1266 threads the needle head 1265 and needle 1256 up and down through female threads in the actuation nut 1268. The resulting vertical motion causes the space between the end of the needle tip and the end of the barrel tip to vary, developing a variable orifice 1240. Expanded fluid is then discharged directly into the collection fluid or into the collection vessel. In this design, the entire needle and knob assembly rotates with respect to the barrel tip 1233.

The expansion of the supercritical fluid occurs essentially at the discharge opening 1240 of the tip 1233, 1257, making the extent of conduit exposed to expanded extraction fluid almost without length, so the expansion occurs in contact with the collection solvent, and the analyte precipitates from the extraction fluid directly into the collection solvent. This improves collection efficiency and decreases plugging.

supercritical pressure is maintained down to the orifice or restriction region 1240 of the distal end of the barrel tip, which is inserted into a collection solvent or collection vessel. The distance between the point of the needle tip 1203 and the recessed seat in the barrel tip forms a variable orifice at 1240 which controls the flow rate, and is adjusted using knob 1266.

For such adjustment, the control needle head 1265 is finely threaded, using 80 threads per inch. Rotating the knob 1266 threads the needle 1256 up and down through action of female threads in the actuation nut 1268 upon needle head 1265. The resulting vertical motion causes the space between the end of the needle tip and the end of the barrel tip to vary, developing a variable orifice 1240. Expanded fluid is then discharged directly into the collection fluid or into the collection vessel. In this design, the entire needle and knob assembly rotates with respect to the barrel tip 1233.

In FIG. 9 there is shown a partly broken away, partly sectioned view of a variable restrictor forming a portion of the assembly of FIG. 8 and in FIG. 10 there is shown an enlarged fragmentary sectional view of the restrictor of FIG. 9. The needle tip 1257 shown in FIG. 8 is not shown in either FIG. 9 or FIG. 10 but a heater for heating the restrictor is shown comprising a winding 1201 of resistance wire 1243 that is connected to the temperature control section 1015 (FIG. 8). This heater is used to electrically heat the barrel tip 1233 in the vicinity of the orifice or metering or restriction region 1240. The heating decreases plugging at the orifice. The helical coil 1201 comprises approximately 30 turns of resistance wire 1243 having a high temperature coefficient of resistance.

The wire 1243 is Pelcoloy (registered trademark of Molecu-Wire Company), 0.004" diameter insulated with a polyimide coating with a thickness of about 0.00025". This wire is composed of 70% nickel and 30% iron and has a temperature coefficient of +4,000 parts per million per degree celsius. One end of the wire 1243 is resistance welded to the barrel tip 1233 at location 1241. (FIG. 10). The other end of the coil is led up the barrel and resistance welded at location 1235 onto step 1244 of electical connection ring 1238.

To insure a good thermal contact between the wire 1243 and the barrel, the barrel is first given a coating of uncured epoxy resin mix (Epoxylite Corp. type #5403) underneath the location upon which the wire is to be set. When the wire is wound on the barrel through the epoxy resin 1242, the epoxy resin fills all of the gap between the wire and the barrel. The epoxy is also placed along the length of wire 1243 which extends from the coil to the resistance weld at electrical connection at 1235. Electrical connection ring 1238 lies on the step 1245 of electrical insulator ring 1237.

From FIG. 9 it is apparent that, if a voltage is applied between electrical connection ring 1238 and barrel holding flange 1236, an electric current flows through ring 1238, resistance weld 1235, wire 1243, heating coil 1201, resistance weld 1241 (FIG. 10), barrel tip 1233, barrel 1234 and flange 1236. This heats the barrel tip 1233 in the region of the metering restriction tip 1240, therefore heating the metering orifice and preventing the formation of either ice or precipitated analyte. Preferably the heating is effected through a temperature controller which senses temperature by substantially constantly monitoring the electrical resistance of the aforedescribed circuit.

Figure 11:
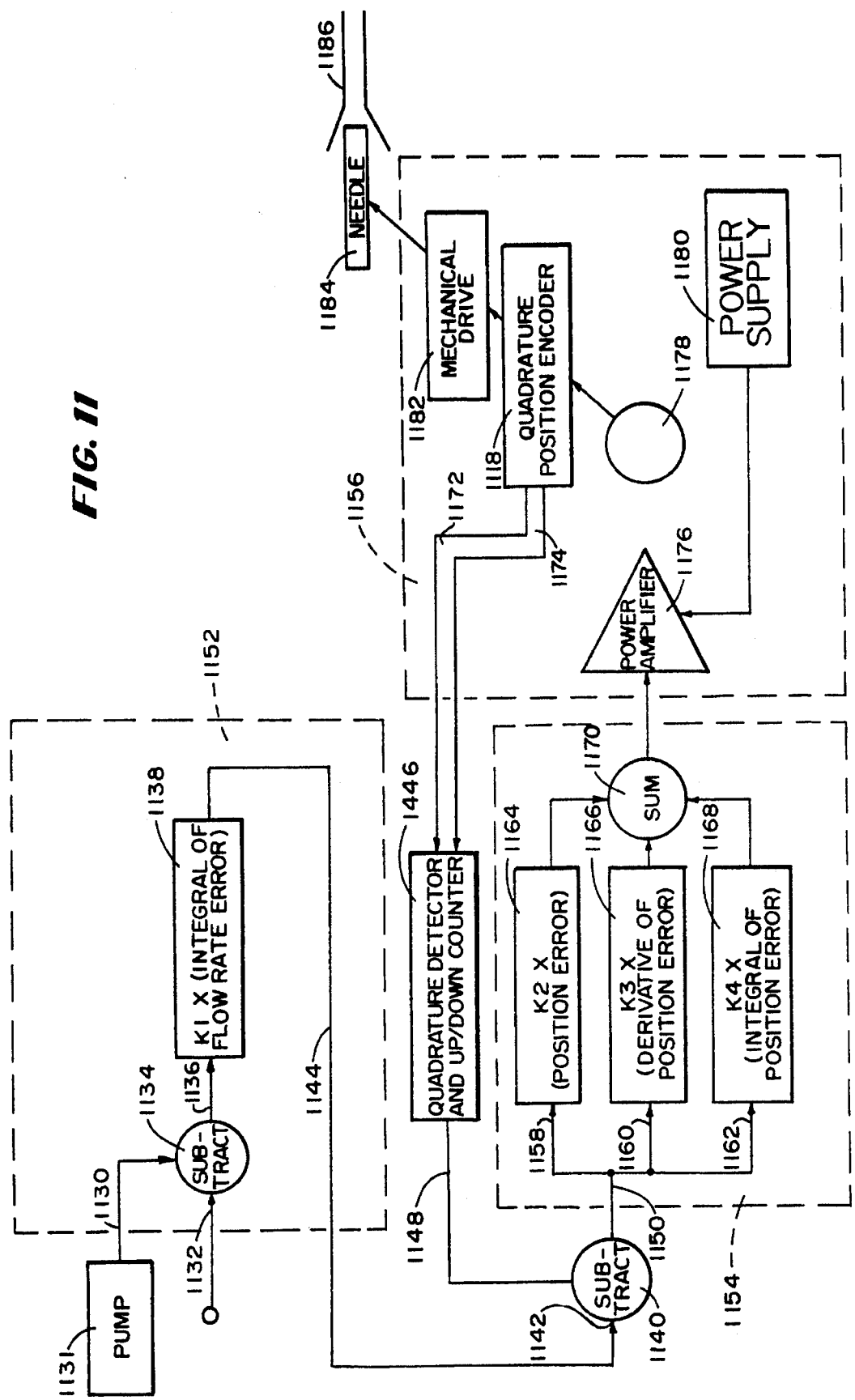
FIG. 11 is a block diagram of a circuit usable in accordance with the embodiment of FIG. 7.

In FIG. 11, there is shown a block diagram of the restrictor and the controller for the restrictor. This controller may be used for control of the motorized variable restrictor for automatic independent control of the pressure within, and fluid flow rate through, an associated supercritical fluid extractor or supercritical fluid chromatograph. In this embodiment, the pump sets a constant pressure and the restrictor sets a constant flow.

The restrictor controller of FIG. 11 has a motor angular position set point signal generator 1152, a servo amplifier 1154, a restrictor-valve control circuit 1156, an up/down counter and decoder, a subtractor 1142, a needle 1184 and a valve seat 1186. An Isco "D" series pump 1131 keeps the system at constant pressure and the restrictor is servo-operated to maintain a desired flow rate.

A flow rate feedback signal on the flow rate feedback conductor 1130 is read from the volume (piston displacement) sensor in the syringe pump 1131. Thus, no gas flow rate measuring transducer is required at the outlet. This pump piston feedback signal is subtracted from the flow rate set point signal on the flow rate set point conductor 1132 entered by the operator in a signal subtraction circuit 1134. The result is a flow rate error signal on conductor 1136 (a difference) which is integrated and multiplied by a constant K1 in multiplier 1138 and is sent to a second subtraction circuit 1140 as a valve motor angular position set point signal applied to input 1142 through a conductor 1144.

The restrictor valve position is sensed by motor shaft position encoder 1118, converted to motor position by quadrature detector/counter 1146 and presented as valve motor position signal on conductor 1148.

The valve motor angular position signal on conductor 1148 is subtracted from the motor angular position set point signal 1142, resulting in a valve position error signal on conductor 1150. This signal is applied to a servo circuit 1154. An amount equal to the constant K2 times the position error signal on conductor 1158, plus a constant K3 times the rate of change of position error on conductor 1160, and plus a constant K4 times the integral of the position error on conductor 1162 is then numerically summed in adder 1170 and the power amplifier 1176 is controlled based on this sum from 1170.

The power amplifier 1176, deriving power from power supply 1180, excites the valve motor 1178, causing it to rotate. A quadrature position encoder 1118 attached to the motor shaft 1178, signals the current position and direction of rotation using two phase signals 1172 and 1174. These signals 1172 and 1174 are measured by the quadrature detector and up/down counter 1146, which provides the valve motor angular feedback signal 1148 to the position subtraction circuit 1140.

The motor 1178 is also attached to the mechanical drive 1182 that moves and positions the needle 1184 with respect to the seat 1186. This can be any mechanism that translates the rotational motion of the motor 1178 into a position adjustment of the needle 1184.

Figure 13:
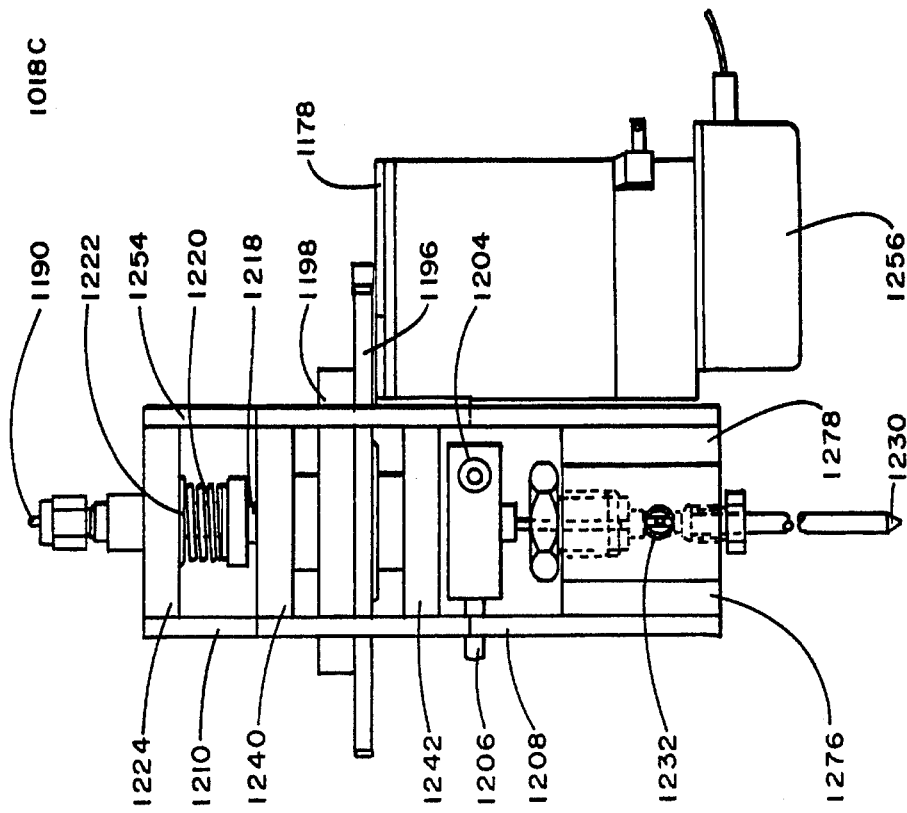
FIGS. 12 and 13 are front and side elevational sectional views of variable restrictors in accordance with an embodiment of the invention.
Figure 12:
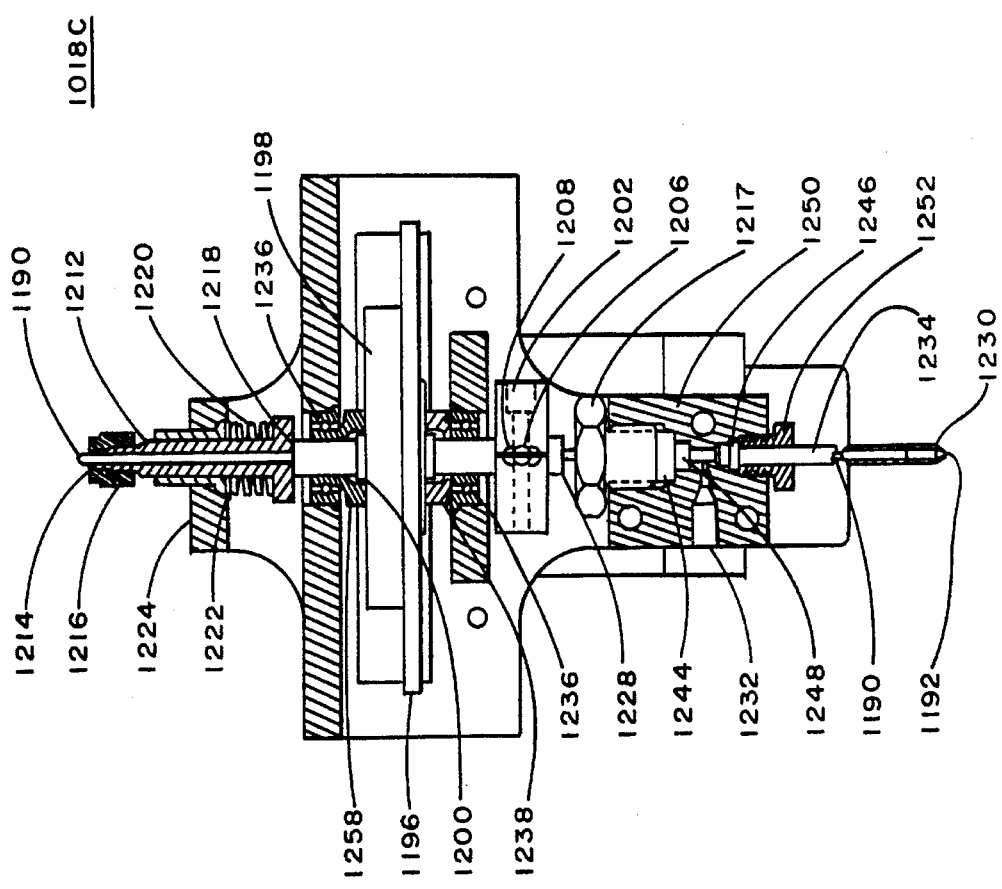

In FIGS. 12 and 13, there is shown a front elevational sectional view and a side elevational sectioned view of a motor controlled restrictor operated by spring compression. Mechanically, the closing force is supplied by spring compression, rather than by a torsion spring. In this arrangement, the needle 1190 can be positively prevented from rotating during closing, preventing destructive galling of the needle tip 1192.

The opening motion is provided by motor 1178, a Lo-Cog (registered trademark of Pittman Motor Co., Harleyville, Pa. 19438-0003) D-C Servo Motor, model 9413, manufactured by Pittmann. Any suitable motor or mechanical device creating rotational motion at enough torque would work as well.

A 64 pitch, 11 tooth gear, supplied by Pittman attached to and part of motor 1178, rotates a 64 pitch, 192 tooth 20° pressure angle Delrin™ (DuPont) spur gear 1196, purchased from Forest City Gear, part number 69-0943-237. Spur gear 1196 is mounted to a support spool 1198, machined from 17-4 PH stainless steel, hardened to Rockwell C42-48. Spool 1198 is threaded onto 182FM (Carpenter Technologies) stainless steel shaft 1200 with 5/16–48 UNS threads. The shaft 1200 is prevented from rotating by clamp 1202, which is held to the shaft by friction force created by a #4-40 cap screw 1204 (FIG. 13). The rotation of clamp 1202 is prevented by pin 1206, which travels in a slot 1208 in the support plate 1210. The rotation of spool 1198 results in a vertical motion of shaft 1200, which presses against the spring retainer 1212 at 1218, lifting the needle 1190. The needle 1190 is attached to the spring retainer 1212 by a compression fitting (Vespel TM DuPont ferrule) 1214, which is compressed and held in place by compression nut 1216.

As the spring retainer 1212 is lifted by action of motor 1178, gear 1196, spool 1198 and shaft 1200, the helical compression spring 1220 is compressed. When this spring 1220 is compressed flat, the mechanism stalls the motor 1178, limiting the distance the needle 1190 can be lifted.

When the motor 1178 is operated in the opposite direction, closing the variable orifice 1192, the shaft 1200 is lowered, and the spring 1220 force the needle 1190 downward. A type 316 stainless steel wear spacer 1222 is used to prevent damage to the aluminum top block 1224 by spring 1220. Once the variable orifice is fully closed, shaft 1200 separates from the spring retainer 1212, and the variable orifice is held closed by spring force only.

When the orifice 1192 is fully closed, the spring 1220 is still somewhat compressed, and hold the orifice 1192 closed with 20 to 40 lbs. of force. As the motor 1178 continues to lower the shaft 1200, the shaft 1200 contacts the seal capture nut 1217 at 1228, causing the motor 1178 to stall. This limits the distance shaft 1200 can move downward, eliminating the need for shaft position switches.

The spool 1198 and gear 1196 assembly rotates freely on ball bearings 1236, and is supported by spacers 1238 from the bearings 1236. Bearings 1236 are lightly pressed into the support plates 1240 and 1242. Shaft 1200 is about 0.001" smaller in diameter than the inner diameter of bearings 1236, and can freely move vertically inside the bearing 1236.

The needle 1190 is attached to the spring retainer 1212 using a compression ferrule 1214 and nut 1216. This method allows the needle 1212 to be positioned during assembly and adjusted if necessary. The needle 1212 is prevented from buckling in operation by being contained throughout its length inside the spring retainer 1212, shaft 1200, seal capture nut 1217 and probe 1234. Throttling of the supercritical fluid takes place between the narrow coned end 1192 of the needle 1190 and a broader angled female cone in tip 1230.

Supercritical fluid enters the apparatus through a compression fitting port 1232, and flows in the annular space created by the probe 1234 and the needle 1190. The fluid is prevented from flowing upwards along the needle 1190 by the PTFE seal with canted coil backing spring 1248, type X15829 made by Bal-Seal and described above. A 303 stainless steel backing ring 1244 holds the seal 1248 in place in the body 1250, and is retained by a seal backing nut 1217. A 303 stainless ring 1246 is soldered to the probe 1234, and makes a metal to metal seal with the body 1250 due to the compression action of the holding nut 1252. Optionally, a gasket washer can be incorporated to facilitate sealing. The fluid path formed is as small as possible, to reduce dead volumes and prevent the necessity of washing out the apparatus. None of the drive components and anti-rotation features are in the fluid path.

The components of the apparatus are held together by two parallel side plates 1210 and 1254. A spring support block 1224 transfers the spring force to the side plates 1210 and 1254, which transfers the spring force to the spacer blocks 1276 and 1278 and body 1250. The probe 1234 is attached to the body 1250 with the holding nut 1252, and holds the tip 1230. The spring force is transferred to the tip through this path, and results in a tensile loading of the outer tube of the probe.

The upper end of the spring 1220 transfers the spring force to the spring retainer 1212, which transfers the force to the needle 1190 through the compression ferrule 1214 held in place by the nut 1216. This results in a compressive force on the needle 1190 that produces the tensile force in the probe 1234. The needle 1190 can be driven downwards into tight fit within the tip 1230 only through force from the spring 1220. The motor 1178 can lift the needle away from the tip and against the springs. Force from the motor does not lower the needle, and therefore the action of the valve is "motor-to-open/spring-to-close". This prevents damage to the end 1192 of the needle and to the seat within tip 1230. The motor position is sensed by encoder 1256. The motor is indicated as 1178 in FIGS. 14 and 17.

Figure 14:
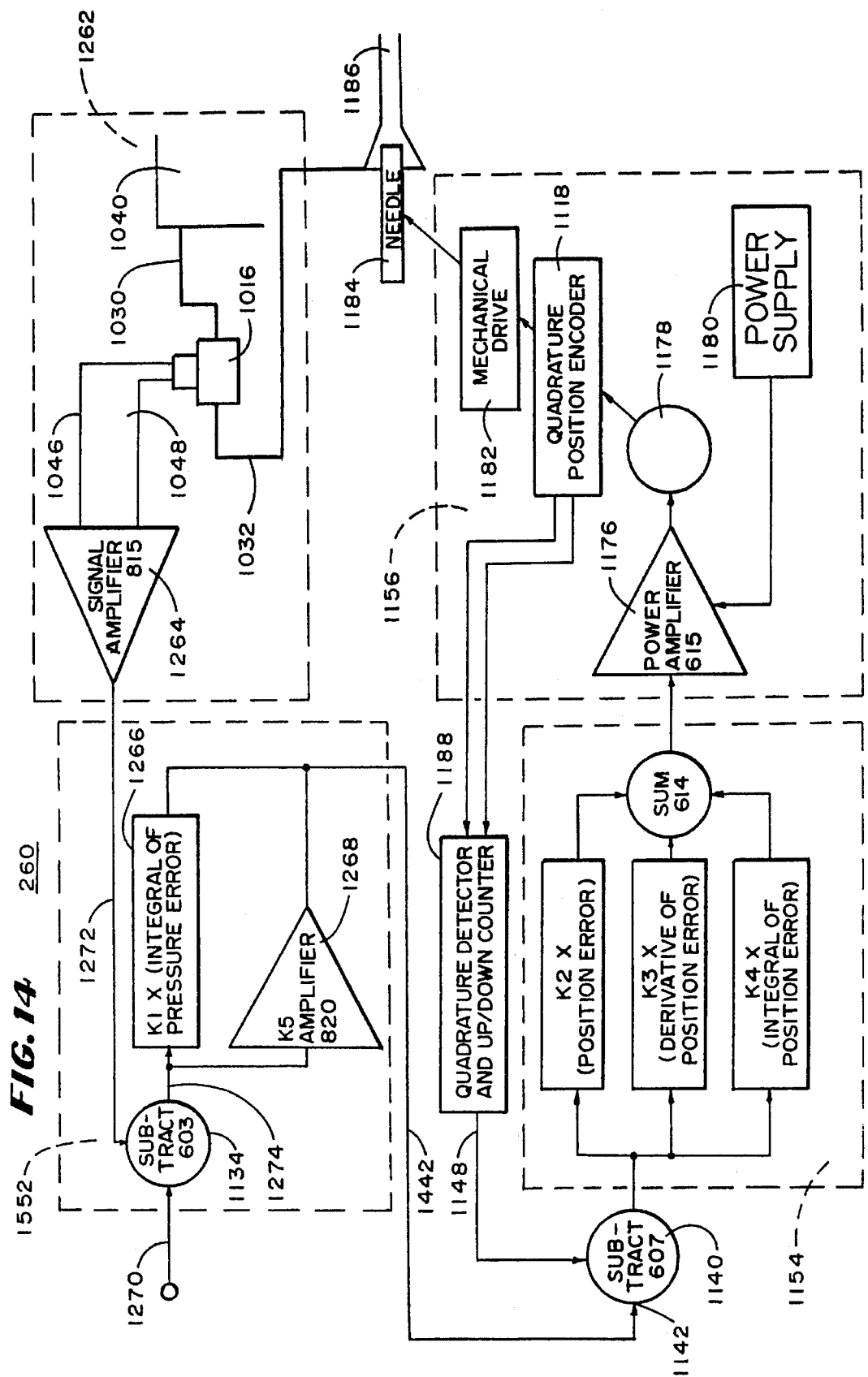
FIG. 14 is a block diagram of another embodiment of circuit usable with the embodiments of FIG. 7 and 12.

In FIG. 14, there is shown another automatic restrictor control embodiment in which the pump sets a constant flow and the restrictor sets a constant pressure. The restrictor and restrictor controller have a motor angular position set point signal generator 1152, an up/down counter 1188, a subtractor 1140, a servo amplifier 1154, a restrictor valve control circuit 1156, a movable needle 1184, a valve seat 1186 and a pressure monitoring system 1262. The pump (not shown) driven by motor 1178 supplies the fluid to the apparatus as a constant volumetric flow and the restrictor regulates the expansion process by controlling the pressure.

In cooperation with the circuit of FIG. 14, the pressure transducer 1016 monitors pressure in tubing 1030 connected to the outlet of supercritical fluid extractor 1040 and in connecting tubing 1032 upstream of the variable restrictor needle 1184 and seat 1186. An electrical signal from the transducer is carried on leads 1046 and 1048 to signal amplifier 1264. The output of the amplifier on lead 1272 is a pressure feedback signal. The pressure feedback signal 1272 is subtracted from a desired pressure set point 1270 using a subtraction circuit 1134. The result is a pressure error 1274 signal, which is multiplied at amplifier 1268 by a constant K5 and integrated at 1266. The outputs of amplifier 1268 and integrator 1266 are added together and create a valve motor angular position set point signal on lead 1142. This valve motor angular position set point signal is logically and functionally identical to the motor angular position set point based on flow rate 1142 (FIG. 11). The remainder of the control circuit is the same as in FIG. 11, except that since the principal feedback is pressure instead of pump piston displacement, the restrictor controls pressure rather than flow rate.

Figure 15:
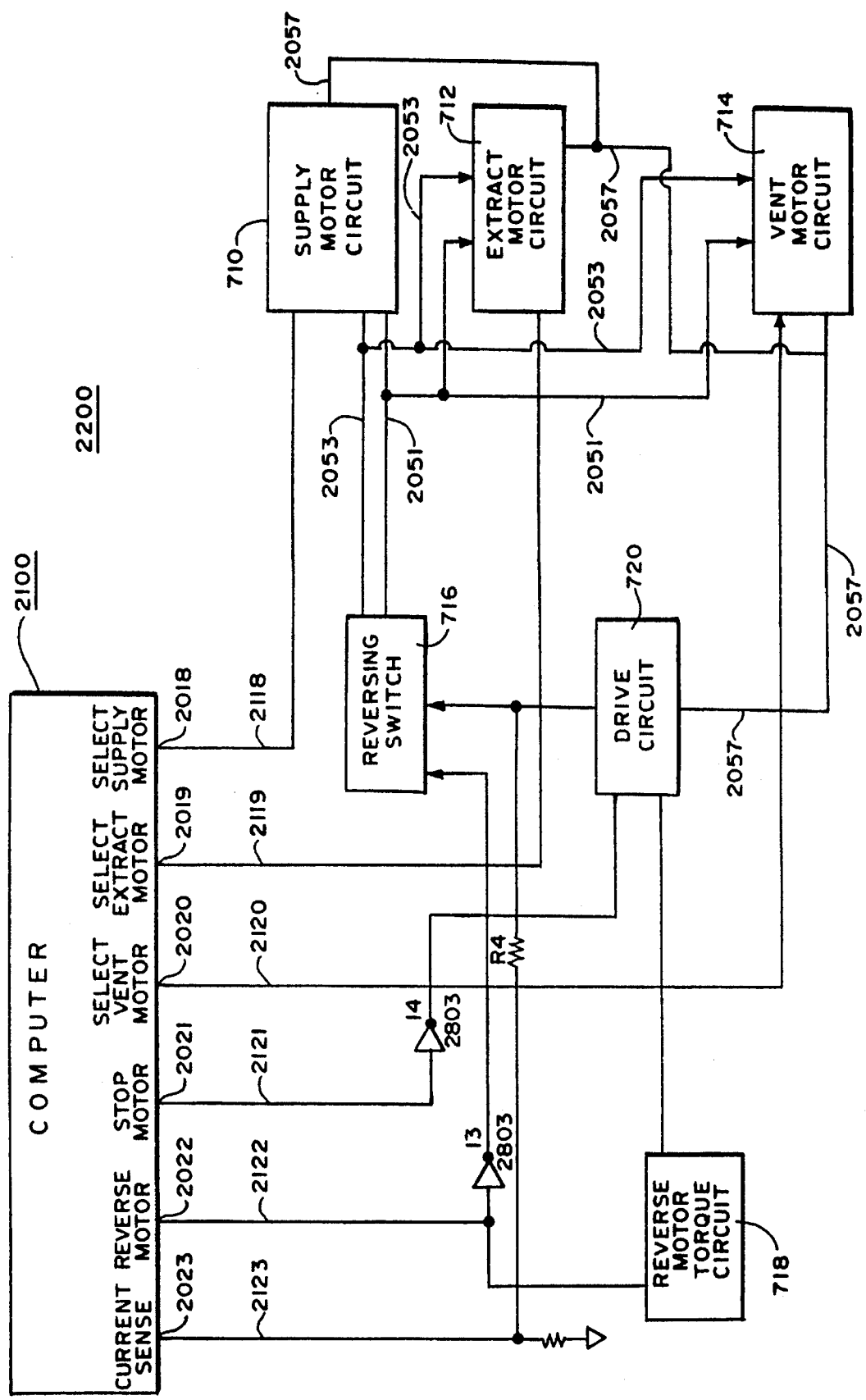
FIG. 15 is a block diagram of the circuitry for operating the system.

In FIG. 15, there is shown a block circuit diagram of the control circuitry 2200 for gear motor 570 (FIGS. 4, 5 and 6) which operates supercritical fluid supply valve 54A (FIG. 6), gear motor 574 (FIG. 5) which operates extraction valve 50A (FIG. 5), and gear motor 573 (FIG. 4) which then operates valve 52A (FIG. 4).

The control circuitry 2200 includes a programmer or other computer 2100, controlling a supply motor circuit 710, an extract motor circuit 712 and a vent motor circuit 714 to control the valves 54A (FIG. 6), 50A (FIG. 5) and 52A (FIG. 4), respectively, a reversing switch 716, a drive circuit 720 and a reverse motor torque circuit 718. The computer 2100 is electrically connected to the supply motor circuit 710, the extract motor circuit 712 and the vent motor circuit 714 through a conductors 2118, 2119 and 2120 electrically connected to output terminals of the computer 2100.

The drive circuit 720 supplies power to a reversing switch 716 that is also electrically connected to the supply motor circuit 710, the extract motor circuit 712 and the vent motor circuit 714 to apply power to the selected one of those motors with a polarity that controls the direction of movement of the motors to open a valve or close a valve. The reversing switch 716 is electrically connected to conductor 2122 from a port 2022 in the computer to activate the reverse direction for closing the valve. This port is electrically connected to the reverse motor torque circuit 718 which controls the amount of torque in opening the valve and is for that purpose electrically connected to the drive circuit 720. A feedback circuit on conductor 2057 is electrically connected to the supply motor circuit 710, extract motor circuit 712 and vent motor circuit 714 to provide a feedback signal to the controller which controls the stopping of the motor when the valves close fully. The stop motor signal comes from conductor 2121 from the port 2021 in the computer or programmer 2100.

In the preferred embodiment, a programmable computer with timing circuits is utilized. It is the same computer used to operate the embodiment of FIG. 3. However, a manual switch can be used instead which switch is connected to a positive voltage supply to energize the corresponding motor when closed.

The control circuit 2200 includes a supply motor circuit 710, an extract motor circuit 712, a vent motor circuit 714, a computer or programmer 2100, a reversing switch 716, a drive circuit 720 and a reverse motor torque circuit 718. The supply motor circuit 710, extract motor circuit 712 and vent motor circuit 714 open and close corresponding ones of the valves 54A, 50A and 52A.

To control the valves, the computer or programmer 2100 has a plurality of output conductors that determine which valve is to be moved and the direction in which it is to be moved. This, in the preferred embodiment, is the computer which operates the extractor 10A (FIG. 3) but may be any timing device or indeed, instead of a programmer, manual switches may be used to close circuits to 15-volt DC voltages to open and close the valves as desired by an operator.

In the preferred embodiment, conductors 2118, 2119 and 2120 are connected to outputs 2018, 2019 and 2020, respectively, of the computer or programmer 2100 and to corresponding ones of the supply motor circuit 710, extract motor circuit 712 and vent motor circuit 714 to select those valves for opening or closing. A low-level signal on lead 2127 attached to computer output port 2021 is electrically connected through inverter 2026 to the drive circuit 720 to cause it to supply power to the selected valve through the reversing switch 716 which is electrically connected to the port 2023 through conductor 2123 to the reversing switch 716 and drive circuit 712.

The reversing switch 716 is electrically connected through conductors on the same cartridge may be made by leaving the sample cartridge 30A in place and advancing only the collection reel. The cycle of opening the valves and extracting is then repeated until the number of extractions from the single sample cartridge 30A (FIG. 3) have been made and the extractant deposited in a number of successive collection vials.

Figure 16:
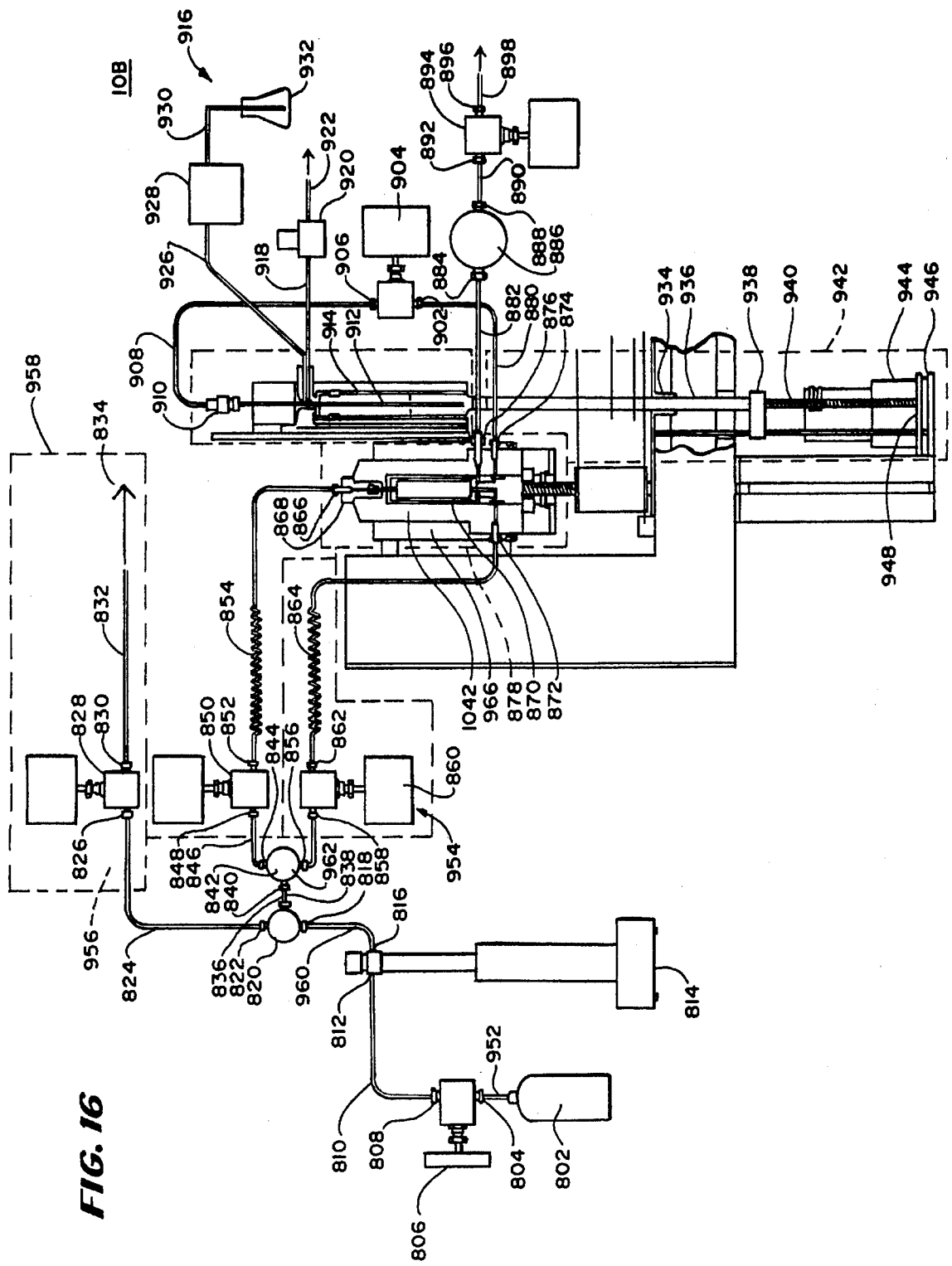
FIG. 16 is a schematic diagram illustrating another embodiment of automated supercritical fluid extraction.

In FIG. 16, there is shown a schematic fluidic diagram of an automated supercritical fluid extraction system 10B similar to the supercritical fluid extraction systems 10 (FIG. 1) and 10B (FIG. 3) having a pumping system 814, a fluid-extraction assembly 878, and a collection system 916.

To supply extracting fluid to the pumping system 814, the tank 802 communicates with the pumping system 814 through tubing 952, a manual valve 806 and a fitting 804 for the valve 806. The outlet of the valve 806 is connected to the inlet port 812 of the pumping system 814 through the tubing 810 which is connected to the valve 806 by fitting 808 and to the pump by another fitting not shown.

The outlet of the pumping system 814 communicates with the fluid-extraction assembly 878 through two different lines, the inlet valve system 956 (enclosed by dashed lines) and the wash valve system 954 (also enclosed by dashed lines). The pumping system 814 also communicates with the collection system 916 through the cooling valve system 958.

Prior to an extraction, a sample cartridege 870 is moved into the pressure chamber in the manner described above in connection with the embodiment of supercritical fluid extractor 10B (FIG. 3). The pump supplies clean extracting fluid from a source of extracting fluid to one port in the breech plug assembly so that it flows adjacent to the seals to clean them and out of the fluid extracting assembly 878. This fluid does not flow during extracting of a sample.

During an extraction the pump communicates with the sample cartridge 870 located in the fluid-extraction assembly 878 through the inlet valve system 956. The fluid flow path goes from the pump to tee connector 820 through tubing 960 which is connected by fittings 816 and 818. The first tee 820 is connected to a second tee 842 through tubing 838 and fittings 836 and 840.

One outlet of the second tee 842 is connected to an electrically-actuated valve 850 by tubing 846 which is connected using fittings 844 and 848. This electrically-actuated valve 850 is described in U.S. Pat. No. 5,173,188 issued Dec. 22, 1992, form application Ser. No. 07/847,652, filed Mar. 5, 1992, in the names of Robin R. Winter, Robert W. Ailington, Daniel G. Jameson and Dale L. Clay, the disclosure of which is incorporated by reference. The electrically-actuated valve 850 is connected to the inlet housing 868 through a coiled heat exchanger 854 and fittings 852 and 866. In FIG. 16, this heat exchanger, actually located in a recess in aluminum temperature control jacket 966, is shown removed for clarity. A heating element and temperature-sensing thermocouple (neither are shown) are imbedded in the jacket 966. A conventional temperature controller regulates the heating to control the temperature of the jacket and therefore the temperature of extraction vessel 1042.

Pressurized supercritical $CO_2$ is heated in the heat exchanger 854 and enters the extraction vessel 1042 and the interior of the sample cartridge 870. This fluid entry is from the top of the extraction vessel and sample cartridge through an inlet housing as will be explained in greater detail hereinafter.

The inlet housing splits the flow during the initial fill when the chamber is pressurized between the outside and the inside of cartridge 870. The inlet housing is sealed to prevent leakage and to prevent fluid from communication with the surroundings. Inside the cartridge 870 is a void space above the sample. After passing through the void space and sample the fluid enters a nozzle of the breech plug below the cartridge 870.

During extraction there is no fluid flow in tubes 864 or 882 used to clean the breech plug seals as briefly described above. The fluid from the extraction cartridge enters an opening in the nozzle of the breech plug 1010 and proceeds up and around the upper seal and down and around the lower of the seals that seal the breech plug to the pressure vessel. This design eliminates any dead space and, hence, extractant loss. The fluid flow is sufficient to wash out the seals in less than a minute with clean fluid.

A washout port is provided for this purpose. This port communicates directly with the pumping system 814 through the wash valve system 954. This wash valve system 954 communicates with pumping system 814 through the second tee 842. This tee is connected to an electrically-actuated valve 860 by tubing 962 and fittings 858 and 856.

The connection from the valve 860 and the wash out port is provided by a heat exchanger 864 which is actually, physically, located in a recess (not shown) in aluminum temperature control jacket 966. This heat exchanger is connected by fittings 862 and 872. The heat exchanger is made of 1/16" tubing with 0.005 I.D. This small inside diameter is to reduce the volume of the tube to minimize fluid and extract from becoming trapped inside during the extraction cycle when the wash valve is closed.

During washing, valve 850 is closed and fluid in the radial passage within the breech plug 1010 is stationary. Fluid 1022 (FIG. 17) entering the wash port 1046 is directed to the same point 1024 that the fluid from the cartridge reaches just before it diverges to pass over the inner surfaces of the seals. From this point, whether the fluid is from the wash port or cartridge the flow path is the same. The fluid flows through the seals in a split circular path as will be described better in connection with FIG. 18. The fluid converges and exits through the outlet port at fitting 874, the valve 904 and to the collection system. This washing takes place after each extraction to prevent cross-contamination.

After the extraction is complete, valves 850, 860 and 904 are closed. The fluid in the pressure vessel chamber remains stagnant until the pressure is released by vent valve 894. This valve is an electrically-actuated valve and is connected to the chamber through tubing 882 with fittings 876 and 884, and to the over pressure safety diaphragm 886 with tubing 890 and fittings 888 and 892. The fluid is then routed away from the unit to a point of safe disposal through tubing 898 which is connected to valve 894 by fittings 896. The fluid exiting the tube is a gas.

The fluid exiting the outlet port for extractant is routed to restrictor 912 in the collection system 916. Located along this path is tubing 880 which connects the outlet port to the electrically-actuated outlet valve 906 through fittings 874 and 914. The fluid is then routed to a filter 910 by tubing 908 which is connected using fitting 906. Fluid passes through the filter and then through the restrictor 912 which is inserted into vial 914.

The extractant is partitioned within the collection solvent in the vial 914 and the gas leaves through tubing 926. A septum retains gas pressure in the vial and the port maintains pressure with the backpressure regulator 920. A backpressure of greater than 20 psi prevents misting of the solvent. Misting will carry away and lose some of the analyte.

Figure 17:
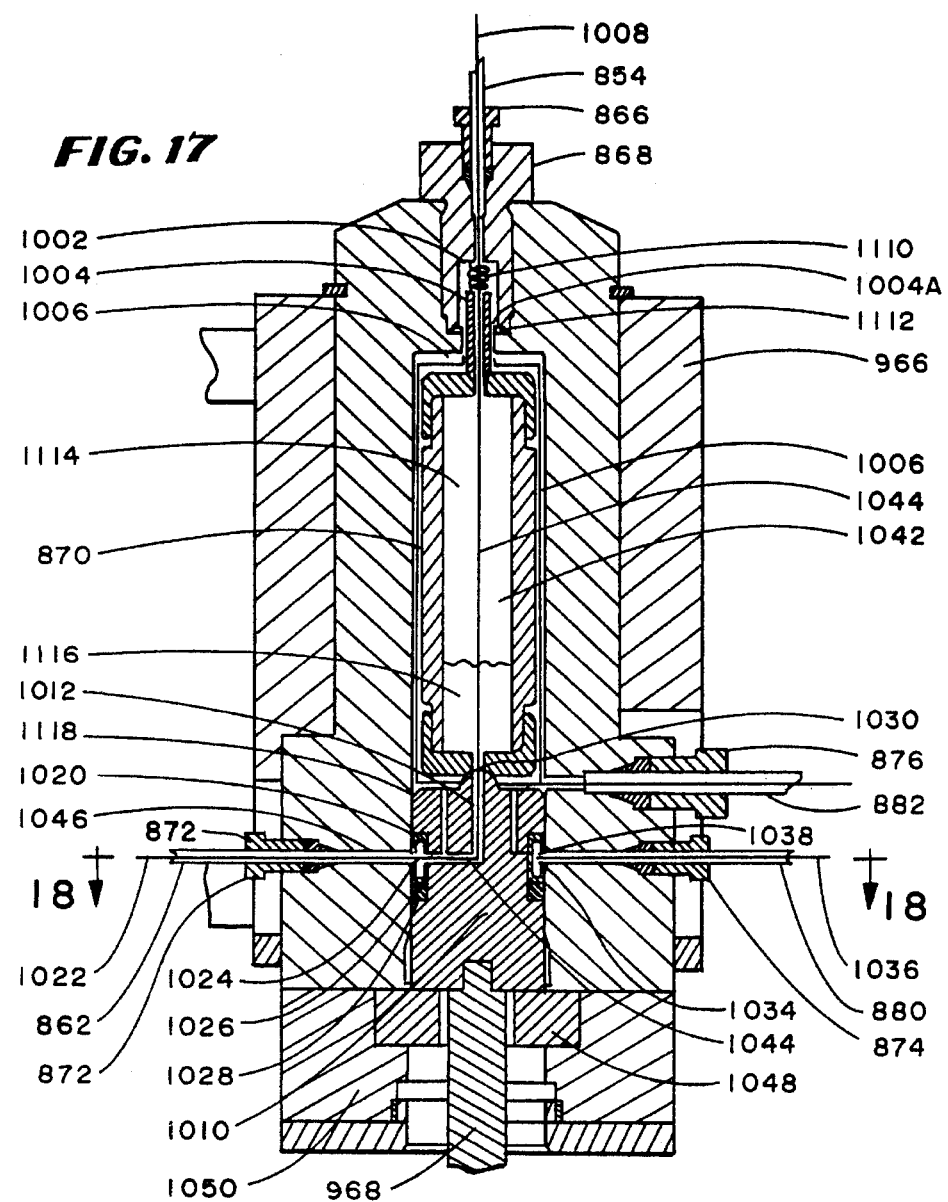
FIG. 17 is a sectional view of one embodiment of extraction chamber, cartridge, breech plug, and flow splitter.

In FIG. 17, there is shown a fragmentary sectional view of the fluid extraction assembly 878 having as its principal parts the cartridge 870, an outlet port at fitting 876 connected to tubing 882, an extracting fluid inlet port fitting 866, a cleaning inlet port fitting 872 and a pressure vessel cleaning fluid outlet port fitting 876.

In operation, pressurized supercritical $CO_2$ is heated in the heat exchanger 854 and enters: (1) the outer chamber space 1006 between the pressure vessel walls and the cartridge through tubing 1008; and (2) the interior 1014 of sample cartridge 870. This fluid entry is through inlet housing 868.

The inlet housing 868 splits the flow during the initial fill when the chamber is pressurized. The flow is split between the outside 1006 and the inside 1014 of cartridge 870. The flow splitter consists of a chamber 1002 inside the inlet housing 868, a spring 1110, and a nozzle 1004. The inlet housing 868 is sealed to prevent leakage and to prevent fluid from communication with the surroundings by a washer seal 1112.

In the preferred embodiment, the seal is made from a soft metal such as copper. The spring 1110 forces the nozzle 1004 against the cartridge and prevents direct communication of fluid between the inside 1014 and space 1006 outside of the cartridge. However, during initial pressurization the nozzle 1004 splits the fluid flow between the inside and outside of cartridge 870 by passing some of the fluid through its center and the rest along slits 1004A along its length on the outside.

The point at which the fluid splits is in a small chamber 1002 located in the inlet housing. The fluid then passes between the nozzle 1004 and washer seal 1112 before entering the chamber space 1006. The design is such that the pressure between the inside and outside of the cartridge is nearly equal at all times. Before and during extraction there is no fluid outflow through tubing 882. The fluid in the space 1006 is static or stagnant during extraction.

Inside the cartridge 870 is a void space 1114 above the sample 1016. After passing through the void space 1114 and sample 1016 the fluid enters the nozzle 1030 of the breech plug 1010.

The breech plug assembly consists of the breech plug 1010, lower seal 1026, seal spacer 1034, upper seal 1020, outlet port or point 1038 and a port tube 1012. During extraction there is no fluid flow in tubes 864 or 882. The fluid from the extraction cartridge enters an opening in the nozzle 1030 of the breech plug 1010 and proceeds through the port tube 1012 which is press fit into breech plug 1010.

The port tube 1012 transports the fluid to the center 1024 of the upper and lower breech plug seals 1020 and 1026. It also locks the orientation of the seal spacer 1034. There are two openings in the seal spacer, one at the port tube 1012 and the other near the outlet port or point 1038. The fluid diverges at point 1024 into a four way split flowing up and around the upper seal and down and around the lower seal. The seal spacer 1034 takes up the space between the seals, thereby forcing the fluid into the seals. This design eliminates any dead space and, hence, extractant loss. The fluid flow is sufficient to wash out the seals in less than a minute with clean fluid.

A washout port is provided for this purpose. This port communicates directly with the pumping system 814 through the wash valve system 954 (FIG. 16). This wash valve system 954 communicates with pumping system 814 through the second tee 842. This tee is connected to an electrically-actuated valve 860 by tubing 962 and fittings 858 and 856.

Figure 18:
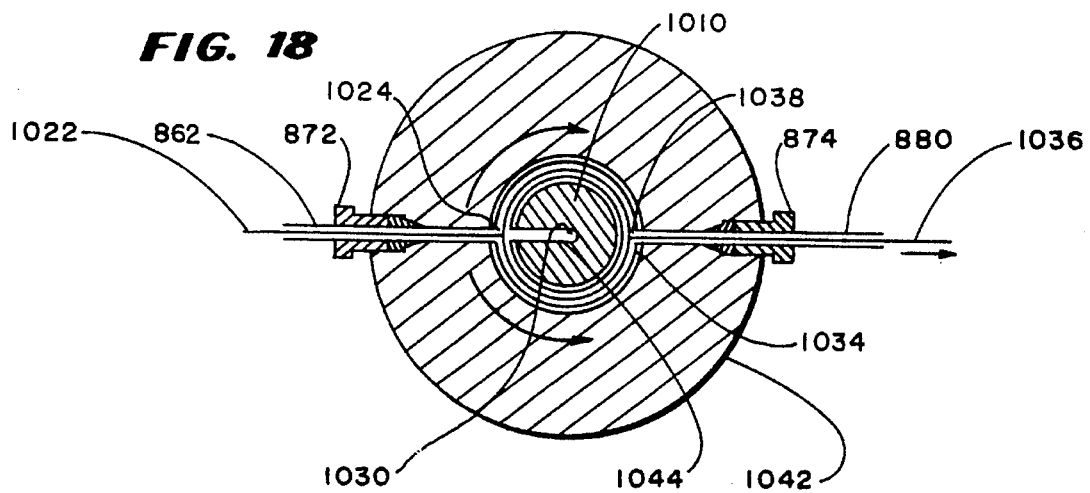
FIG. 18 is a sectional view of the chamber of FIG. 17 taken through lines 21—21 in FIG. 17.

During washing, valve 850 is closed and fluid in passage 1044 is stationary. Fluid 1022 (FIG. 17) entering the wash port 1046 is directed to the same point 1024 that the fluid from the cartridge will reach just before it diverges to pass over the inner surfaces of the seals. From this point, whether the fluid is from the wash port or cartridge the flow path is the same. The fluid flows through the seals in a split circular path as can be seen in FIG. 18 and converges at point 1034. From here it exits through the outlet port 1038 and to the collection system. This washing takes place after each extraction to prevent cross-contamination.

After the extraction is complete, valves 850, 860 and 904 are closed. The fluid in chamber 1006 remains stagnant until the pressure is released by vent valve 894. This valve is an electrically-actuated valve and is connected to the chamber through tubing 882 with fittings 876 and 884, and to the over pressure safety diaphragm 886 with tubing 890 and fittings 888 and 892. The fluid is then routed away from the unit to a point of safe disposal through tubing 898 which is connected to valve 894 by fittings 896. The fluid exiting the tube is a gas.

The fluid exiting the outlet port is routed to restrictor 912 in the collection system 916. Located along this path is tubing 880 which connects the outlet port to the electrically-actuated outlet valve 906 using fittings 874 and 914. The fluid is then routed to a filter 910 by tubing 908 which is connected using fitting 906. Fluid passes through the filter and then through the restrictor 912 which is inserted into vial 914.

In FIG. 18, there is shown a sectional view through lines 21—21 of FIG. 17 showing the seals between the breech plug 1010 and the extraction vessel 1042 and the wash or cleaning inlet port and outlet port at fittings 872 and 874 respectively. The arrows show the circulating of the wash fluid from point 1024 in counterclockwise and clockwise directions between the upper and lower seals from the fitting 872 and out of the fitting 874.

Figure 19:
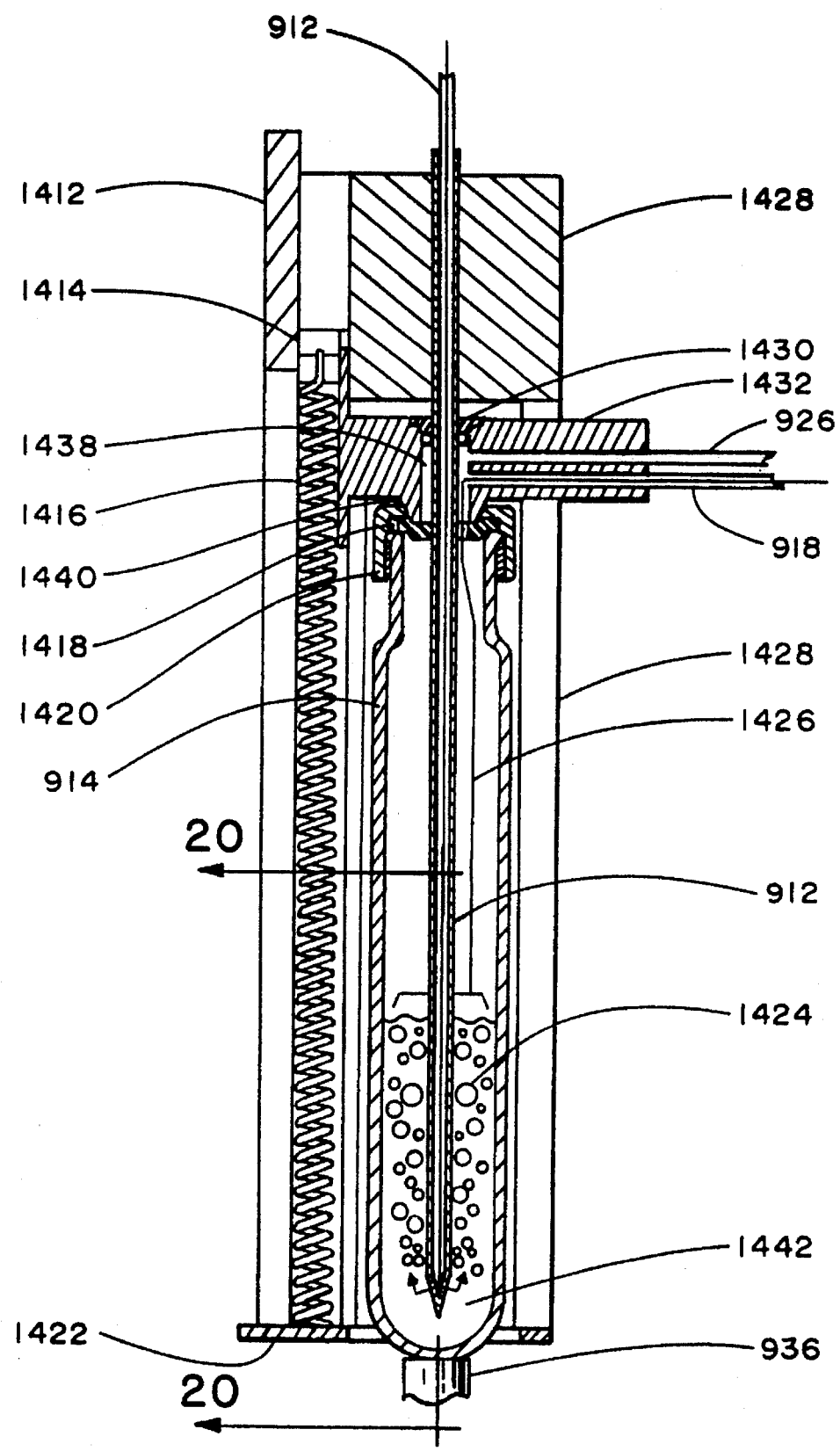
FIG. 19 is a sectional view of the vial septum piercing and solvent collection system assembly.

In FIG. 19, there is shown a fragmentary sectional view of the collection system 916 having as its principal parts a restrictor 912, a solvent 1442, a push tube 936, a vial 914, solvent port or tubing 926 and septum 1418. The fluid containing extract flows through restrictor 912 and exits as a gas at the bottom of vial 914. The expanded gas bubbles 1424 rise upward through solvent 1442 leaving the extract behind in the solvent.

The gas 1426 above the solvent continues rising and passes through a slit in the septum 1418. The septum is held to the mouth of vial 914 by vial cap 1420. The slit in the septum provides a passage for the restrictor. The septum is made of silicone rubber or other flexible, elastic material with a Teflon backing. The restrictor opens the slit in the septum in such a manner that an opening is formed on both sides of the restrictor through which the gas exiting the vial passes. Gas enters a large opening 1438 in the vial guide 1432. The vial guide is sealed against the septum by spring 1416. The other end of spring 1416 is anchored to bottom piece 1422. The large opening 1438 is also sealed by a flange seal 1430 around the restrictor.

The restrictor 912 may be a capillary tube restrictor formed of stainless steel tubing, available from Sterling Stainless Tube Corporation of Englewood, Colo., or it may be a variable restrictor such as shown in FIGS. 8, 12, 13, 15, 16, 28, 29, 30 or 31. Typical useful solvents are liquid dichloromthane and liquid isopropanol. The septum is make of silicone rubber or other flexible elastic material with a Teflon backing (Teflon is a trademark for tetrafluoroethyline fluorocarbon polymers sold by DuPont de Numours, E. I. and Co., Wilmington, Del., 19898).

This design prevents the gas from communicating with the surroundings. The gas passes through tube 918 to a back-pressure regulator 920 (FIG. 16). This regulator causes pressure to build inside the collection vial and decreases collection solvent and extract losses. Misting is essentially eliminated. Also, elevated pressure minimizes the violent bubbling that occurs and allows the amount of solvent to be measured.

A pressure of 40 to 50 psig is satisfactory, as are other pressures in the range of 20 to 200 psi. The gas leaving regulator 920 is routed to a proper disposal point through tubing 922. Also, the vial guide is designed such that if the pressure exceeds a safe value the pressure forces vial guide 1432 up and breaks the seal. This prevents the pressure from exceeding the safety limit of the glass collecting vial. Nevertheless, the vial is located in an enclosure to decrease the risk due to its shattering from the pressure. Control of collecting vessel termperature by refrigerated bath and pressurizing the vessel to the extraction chamber pressure by multiple, mannually operated, needle valves is described by Nam, et al. *Chemosphere*, 19, n. 1–6, pp. 33–38 (1989). Nam does not disclose gassifying a supercritical fluid through a restrictor, nor settable or regulated control of collecting vessel pressure. Nam's system is not suitable for dynamic or flowing extractions.

Although the slitted septum 1418 is not entirely air-tight when the vial 914 is lowered from restrictor 912 and placed in the vial rack (not shown), the septum substantially prevents evaporation of collection solvent and extract when the vial is in the vial rack. The slit tends to reclose.

If additional solvent is needed in the vial, some may be pumped in from a reservoir 932 using pump 928. The fluid is pumped from the reservoir 932 through tubing 930 and then to the vial guide through tubing 926. The fluid enters the opening 1438 inside the vial guide 1432. It then enters the interior of the vial through the same openings in the septum slit from which the gas escapes.

Elevated pressure and reduced temperature generally increases trapping efficiency. Therefore, a provision for precooling and maintaining the collection solvent temperature is provided. Also, low collection solvent temperature may create a problem with restrictor plugging and ice formation.

Figure 20:
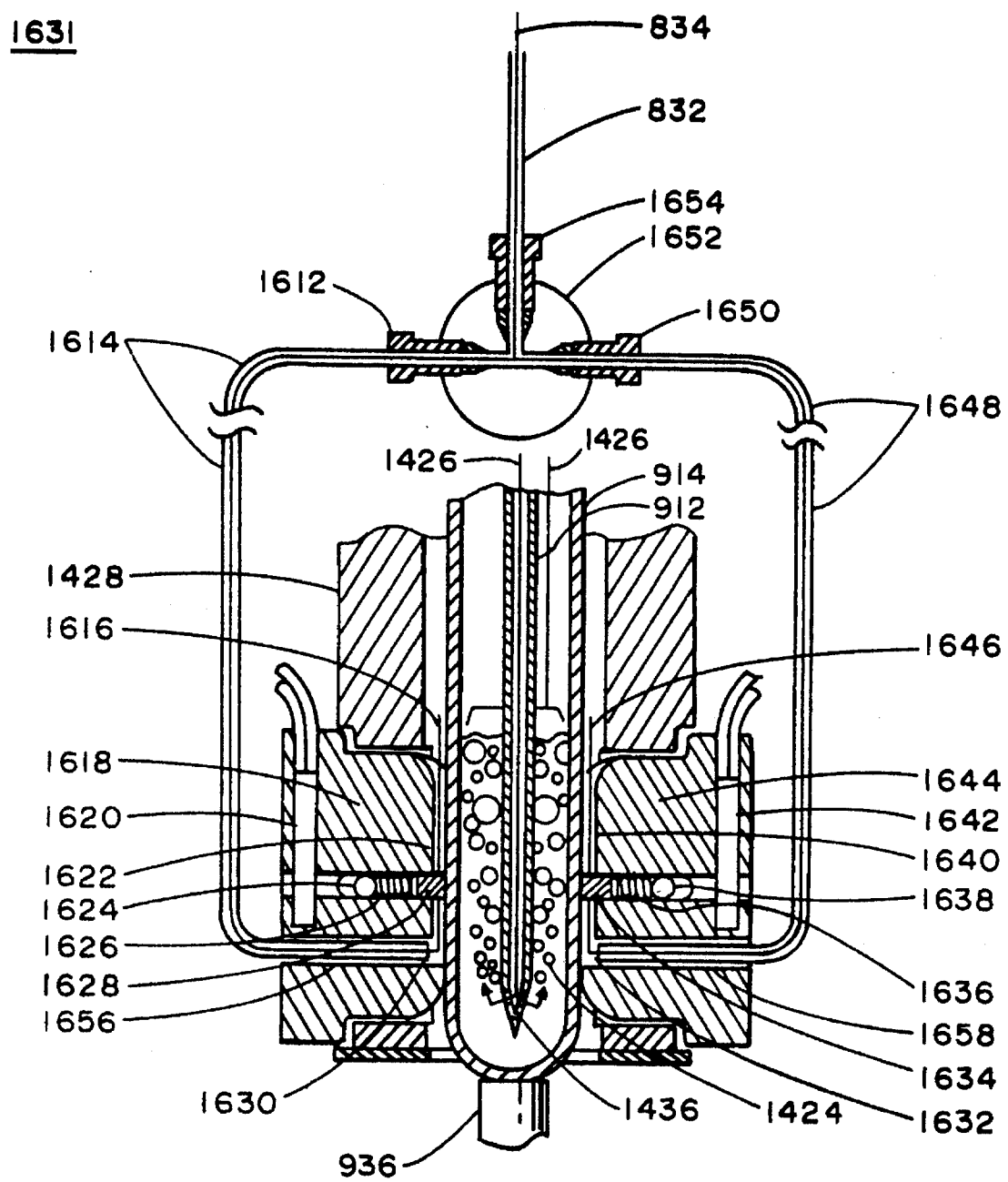
FIG. 20 is another sectional view of the piercing and solvent collection system assembly taken through the vial heater and cooler.

In FIG. 20, there is shown a heating and cooling device 1631 having as its pricipal parts cooling lines 1614, 1648 and 832, blocks 1618 and 1644 and electric heaters 1620 and 1642. The heaters and coolers are arranged to be selectively in thermal contact with the collection vial 914.

For this purpose, lines 1614, 1648 and 832 communicate with the pump through the valve cooling assembly 958 (FIG. 16). This assembly is connected to the first tee 820. The connection is made by tubing 824 which is attached to the electric valve 828 by fittings 822 and 826. This valve is then connected to another tee 1652 located above the collection system.

This connection is made by tubing 832 and fittings 830 and 1654. Fluid 834 enters tee 1652 and is split in two directions. The fluid then flows through two restrictor cooling tubes 1614 and 1648 which are attached to the tee by fittings 1612 and 1650. This pair of restrictors may be made of a flexible material such as stainless steel capillary. Vaporization of liquid $CO_2$ supplied by line 832 cools the collection vial 914 and its contents. Each restrictor provides the same function to opposite sides of the vial. Therefore, each component which controls the temperature of the vial is duplicated on either side.

The blocks 1618 and 1644 to which the restrictor cooling tubes are routed, are spring-clamped onto opposite sides of the vial. These blocks are located in the collection system housing 1412. This housing is preferably made of a non-heat-conducting material such as plastic. Each block is attached to the housing by spring pins, 1624 and 1638. The opening in the block in which the pin passes through are slots. This allows the blocks not only to move toward and away from the vial but to rotate as well. This allows the blocks to be forced out of the way by the vial as it is lifted into position. The rotation makes it easier for the blocks to clear the vial cap 1420 which is larger than the vial 914. Without rotation the blocks may bind when the vial is lifted.

The blocks 1618 and 1644 are forced against the vial by spring 1626 and 1636. These springs are larger than the slots and are inserted in an opening in the side of each block and held in place by set screws, 1628 and 1634. The blocks 1618 and 1644 are made from aluminum which transfers heat from the electric heaters 1620 and 1642 which are also located in the blocks.

Heat is transferred by conduction from the heaters to the surface of the vial. The heaters 1620, 1642 and the $CO_2$ supply valve 828 are controlled by a conventional temperature controller equipped with a thermocouple (not shown) in thermal contact with liquid-filled portion of the vial 914.

To cool the vial, the cooling lines are routed into openings 1656 and 1658 in the blocks. These openings go all the way through the block and allow the cold $CO_2$, which exits the restrictor capillary tubing at points 1630 and 1632, to be directly against the vial. There are small grooves, 1622 and 1660, located along side of the blocks. They form pathways which guide the $CO_2$ along the sides of the vial to increase cooling. The $CO_2$ gas at points 1616 and 1646 is vented to the surroundings and is driven away by natural or forced air convection. This produces the maximum amount of cooling in the least amount of time since this technique does not require that the blocks be cooled before vial cooling begins.

The vial 914 is raised by vial lift 942. This is best illustrated in FIG. 16. The gear motor 944 drives gear 946. This gear is attached to the drive screw 940. The drive screw is held in place by bearing 948. As the drive screw rotates, rotational motion is translated into linear motion by guide nut 938. This nut is attached to the push tube 936 which in turn lifts the vial. The guide nut is prevented from rotating by the guide rod 952 which is anchored top and bottom. The push tube 936 is guided by a linear bearing 934.

After extraction, fluid is discharged from the chamber region 1006 through tube 882, past overpressure blowout plug safety device 886, valve 894 which is opened at this time, and atmosphere vent tube 898. The blowout safety device 886 is always in communication with the chamber 1006, and incorporates a blowout disc that ruptures at a pressure of 15,000 psi. This protects the extraction vessel 1042 (FIG. 17) from dangerous rupture, as it is designed to hold a pressure in excess of 70,000 psi. The normal maximum operating pressure within the extraction vessel 1042 is 10,000 psi.

In order to achieve down flow in the automated unit, the $CO_2$ inlet and a flow splitter must be relocated to the top of the chamber. These devices must fit within the confines of the upper section of the chamber and are contained in an assembly which consists of an inlet housing, spring, nozzle and seal washer. This flow splitter assembly allows the pump to communicate with the inside and outside of the extraction cartridge. The nozzle and spring are captivated in the housing by the seal washer and the nozzle and spring are positioned as such that the spring forces the nozzle out of the housing and into the chamber.

When a cartridge loaded into the chamber compresses the nozzle back into the housing, the force from the spring creates a seal between the nozzle and the cartridge. This prevents fluid in the outer chamber space 1006 from entering the cartridge unless it diffuses through the tortuous path back up around the outside of nozzle 1004.

The washer seal which holds the nozzle in place also seals the housing and prevents fluid from leaking to the outside environment. During an extraction, the fluid enters the housing 868 and flows through a pathway to cavity 1002 where the spring and nozzle are located. From this cavity, the fluid can communicate with either the cartridge or the chamber. The nozzle has a pathway through its center which directs fluid from the cavity to the inlet of the cartridge. Also, there is a slit down the side of the nozzle which creates a pathway from the cavity to the chamber. This design is such that the pressure will remain the same inside and outside the cartridge when filling and during extractions.

After the fluid has passed through the cartridge, and hence the sample, it contains extract from that sample. The fluid must pass through an opening in the breech plug, flow across the seals and exit through the outlet port. During extraction the seals are constantly swept by extraction fluid carrying progressively less and less extract. This prevents accumulation of extract on the seals. Therefore, this flow path must not have any dead space or stagnant regions.

To avoid dead space, the outlet port in the breech plug is oriented 180 degrees from the outlet port of the chamber. This forces the fluid to sweep around the full circumference of the seals. There is a tube 1012 pressed into the outlet port of the breech plug which directs the fluid to the center of the seals. The fluid is forced up into the seals by the seal spacer 1024 which is located between the seals 1020 and 1028. The fluid diverges into four different directions and converges at the chamber outlet port.

To ensure that the seals are clean, a washout port is provided. This port communicates with the pump and delivers clean fluid to the same point that the outlet of the breech plug does. This clean fluid from the pump washes not only the seals but all the tubing including the restrictor which is located downstream.

The collection vial is lifted into the collection system assembly by the vial lift, cooled to a preselected temperature, and then heated or cooled (if necessary) to maintain that temperature. Also, the vial is sealed such that pressure may be maintained and controlled in the vial, and gases are vented to a proper location.

The vial lift mechanism operates independently from the sample cartridge lift which allows vials to be changed at any time during or after the extraction process without depressurizing the extraction chamber. This mechanism is driven by a gear motor and consists of the motor, drive screw, guide nut, and push tube. The drive screw and guide nut converts the rotation of the motor to linear motion which then lifts the vial to the collection assembly.

This collection assembly contains a vial guide, flanged restrictor seal, spring, stationary restrictor, and a collection system housing 1412. The restrictor is anchored by block 1428 to the housing and is centered over the vial. The vial guide is restrained by the assembly housing but is designed such that it may slide up and down its length. There is a large opening in the guide that contains a flanged seal 1430 that the restrictor passes through as the guide moves. This seal and the seal provided by the truncated cone 1440 bearing against septum 1418 prevent communication of gases and vapors in the large opening with the surroundings.

Before the vial is lifted up, the vial guide 1432 has been pulled near the bottom piece 1422 (FIG. 19) by the action of tension spring 1416. The vial first comes into contact with truncated cone 1440 located on the vial guide. This cone enters the hole in the top of vial cap 1420 and causes the vial to center itself on the vial guide before the stationary restrictor becomes inserted through the vial septum 1418.

The septum is held in place by a vial cap 1420 and has a slit which allows the restrictor to pierce through and then close up when it is removed. When there is no vial in the collection system, housing tension spring 1416 pulls down vial guide 1432. The vial lift raises the vial until it contacts the lowered vial guide. Then it lifts both the vial guide and the vial until they have reached the proper location which is when the stationary restrictor is about 0.25 inches from the bottom of the vial, as shown in FIG. 20. The spring 1416 connected between the guide and housing forces the guide down onto the vial septum thereby creating a seal between the two. This seal and the seal 1430 around the restrictor allows pressure to build up in the vial.

The vial guide has 5 basic functions, which are: (1) it guides the vial to the proper position; (2) its spring forces the vial off of the restrictor and back into the vial rack when the vial lifter lowers the vial and this prevents the vial from catching in the collection assembly if it is covered with frost due to cooling; (3) it seals against the vial septum to the truncated cone 1440 and around the restrictor and this seal is capable of holding at least 50 psig; (4) it has a port for adding collection solvent to the vial; and (5) it has a port which vents the extraction gases and vapors.

The replenishment solvent port 926 intersects with the large opening 1438, which the restrictor goes through, on the vial guide. Collection solvent is pumped into the vial through this port from a reservoir. The solvent passes through the port, the large opening and enters the vial through a gap in the septum. This gap is created on either side of the round restrictor when the restrictor is pressed through the pre-made slit in the septum. The solvent is prevented from communicating with the outer environment by the seal between the septum and the vial guide, and also the seal around the restrictor.

The vent port, which intersects the large opening, is connected to a regulator that controls the pressure inside the vial. The gases coming from the restrictor exit the vial through the same slit and gaps around the restrictor that the solvent from the solvent port passes through. Then the gases pass through the large opening port and on to the regulator. From the regulator the gases and vapor are routed to a point of proper disposal.

The temperature of the vial is controlled by heaters and $CO_2$ expansion devices imbedded in two aluminum blocks. These blocks are spring loaded against the vial and are curved on the mating surface such that there is full contact with the vial walls. Also, they are held in place by a pin anchored to the collection system housing. This pin passes through a slot in the blocks and a spring located between this pin and the block is what forces the block against the vial. This pin and slot arrangement enables the blocks to float over the vial cap and vial by rotating as well as move in and out.

The heaters imbedded into the block heat the vial by conduction through the aluminum block. The cooling lines, which communicate with either a $CO_2$ tank or pump, are inserted into an opening in each block which passes all the way through to the vial. This arrangement allows the $CO_2$ to expand from the cooling lines and come into direct contact with the vial without having to cool the entire heating block first. The vial housing, which contains the blocks, is made of plastic which resists heat transfer thereby reducing the thermal mass which is heated or cooled to reach the desired temperature.

The parameters that are controlled for the extraction process include the chamber and heat exchanger temperature, the collection solvent temperature and collection vial pressure, the extraction time and extraction pressure, the wash time and whether multiple vials are needed for the extraction. A conventional microprocessor collecting controller provides all of the control functions.

Prior to the start of an extraction sequence, the valves, refill valve 806, cooling valve 828, inlet valve 850, wash valve 860, and outlet valve 904 are closed. The only exception is the vent valve 894 which may be left open for now.

If the pumping system 814 is empty, the refill valve 806 is opened to allow the $CO_2$ cylinder 802 to communicate with the pumping system 814. The pump is then activated to refill. When complete, refill valve 806 is closed and pumping system 814 is switched to run and is pressurized to the desired extraction pressure.

A vial 914 and cartridge 870 are lifted into position in the manner described previously. A sample cartridge 870 is lifted into position by cartridge elevator 808 which supports Nitronic 60$^R$ breech plug 1010. The breech plug is locked in place by a Nitronic 60 split locking bar 1048 which locks and unlocks through motion perpendicular to the plane of FIG. 17. The operation is similar to that of the locking mechanism of a Winchester model 94 rifle. The locking bar is captivated to the extraction vessel 1042 by slotted plate 1050. The plate 1050 and vessel 1042 are made of 17-4 PH stainless steel hardened to H1050. The material choices of 17-4 PH and Nitronic 60 are made for strength, corrosion resistance and resistance to galling.

After the pumping system 814 is pressurized, the vent valve 894 is closed and the inlet valve 850 is opened. The pumping system 814 now communicates with the chamber 1042 and pressurizes chamber 1042, the interior 1014, 1016 of cartridge 870 and its exterior 1006 through the flow splitter 1002, 1004, 1110.

While the chamber 1042 is pressurizing, the vial 914 may be cooled if desired. If so, the cooling valve 828 is opened allowing the pumping system 814 to communicate with the cooling restrictors 1614 and 1648. The vial 914 will continue to be cooled until it reaches the selected temperature. At this time the heaters 1620 and 1642 may be turned on by their associated temperature controller to regulate this temperature, unless a very low temperature is selected.

When the pumping system 814 has pressurized the chamber 1042 to its selected pressure, the outlet valve 894 is opened. The pumping system 814 is now communicating with the restrictor and hence the vial 914. The fluid flows through the heat exchanger 854, is heated to supercritical temperature, and enters the cartridge at a selected supercritical temperature. After passing through the sample 1016 the fluid proceeds to the restrictor 912 through the breech plug 1010 and seals 1020 and 1026. At the vial 914 the pressure builds due to the pressure regulator 920 located downstream of the vent port. When the preset, regulated pressure inside the vial is reached, the gas and vapors will proceed to a disposal point.

If during the extraction, additional collection solvent is needed in the collection vial 914, a pump 928 is activated and fluid is pumped from reservoir 932 to the vial 914.

This extraction process continues for the preselected time interval and at the end the process is either terminated and a new cartridge 870 and vial 914 are loaded or only vial 914 may be changed along with any of the extraction parameters such as temperature and pressure. If the latter is chosen, the outlet valve 904 is closed and the wash valve 860 is opened for a preselected interval. At the end of the wash interval, wash valve 860 and outlet valve 904 are closed and the vial 914 is lowered and a new one inserted in a manner described previously. At this time the outlet valve is reopened if all the parameters are stabilized.

When the sample cartridge has been extracted, a new vial 914 is selected, which may be a wash vial. A group of several wash vials may be used in sequence after each collecting vial. For each, the wash valve 860 is opened for another preselected interval and the vial loading and unloading process is repeated until the new collection vial is loaded. The same group of wash vials can be used to wash all of the collecting vials because the dilution of contaminants is exponential for each wash vial change.

After this cycle, when no further changing of vials is required, the outlet valve 904 and inlet valve 850 are closed and the vent valve 894 is opened for a length of time sufficient to vent the chamber. When the chamber is at atmospheric pressure the sample cartridge 870 and vial 914 are unloaded and unit is ready for the extraction sequence to be repeated on another sample.

The embodiment of FIGS. 19–23 may be modified to provide a variable restrictor similar to the variable restrictors of FIGS. 7–13. In such a modification, a probe assembly and point restrictor similar to that disclosed in FIGS. 8, 12, 13, 15, 16, 28, 29, 30 or 31 is used instead of a restrictor tube such as the restrictor 912. In the preferred embodiment, a variable restrictor of the type shown in FIGS. 28, 29, 30 and 31 is used.

In another modification the adjustable orifice at 1240 is formed and controlled differently so as to avoid the need for the needle tip 1257 and the mechanism that adjusts its position with respect to the barrel tip 1233 to control the pressure in the extractor, the tubing between the extractor and the point restrictor and to control the rate of release and the expansion of effluent into the collection environment. In this modification, the point restrictor is formed between the end of the probe and the adjacent surface of the collection container.

The rate of release of effluent is controlled by adjusting the distance between the end of the probe and the bottom wall of the collection container. This distance can be adjusted by moving the push rod 936 up or down as described in connection with FIGS. 19, 22 and 23 while holding the probe stationary or by moving the probe such as with an electromagnet or screw drive with respect to the bottom wall of the collector container. The distance between the tip of the probe and the wall of the container controls the rate of release of the fluid from the probe.

Figure 21:
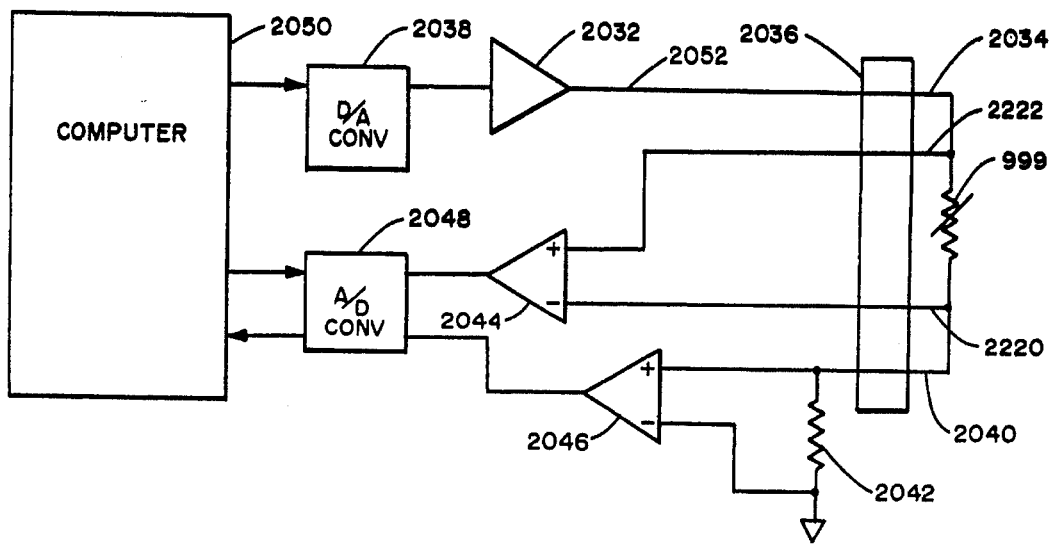
FIG. 21 is a schematic circuit diagram of an interface and computer control system useful in measuring and controlling the temperature of restrictors in accordance with the embodiments of FIGS. 1–20 and 25–28.

In FIG. 21, there is shown a block diagram of an interface and computer control system 2051 that measures and controls the temperature of a heater on a restrictor. One end of the heater is connected to the power amplifier 2032 by a conductor 2034 through connector 2036. The computer drives the power amplifier 2032 through D/A converter 2038. The output current from power amplifier 2032 flows through conductor 2034, through the electrical resistance provided by the circuit path through the heater 999, wire 2040, and through current sensing resistor 2042 to the power return.

The voltage across the heater is amplified by a differential amplifier 2044. The current through the heater generates a proportional voltage across resistor 2042. This voltage is proportional to current and is amplified by differential amplifier 2046. The voltage and current signals are digitized by multiplexing A/D converter 2048 and transmitted to a computer 2050 which measures the voltage across and current through the heater. The resistance is then computed in the computer by division. The resistance relationship to temperature is described by equation 1, where R=heater resistance at temperature T, $R_o$=heater resistance at 0° Centigrade, K=temperature constant for the heater wire, (K is about 0.004 for type Pelcoloy (Molecu Wire Co.). For a maximum overall temperature range of 150° C., this reflects a 60% change in resistance.)

The temperature can then be calculated by equation 2.

The parameter $R_o$ is measured automatically by the interface and computer control system 2051 of FIG. 21 at a known temperature such as at ambient temperature before the restrictor is heated. This is done by the computer 2050 causing the digital to Equation 1

$$R = R_o * (1 + KT)$$

Equation 2

$$T = (R - R_o)/KR_o$$

Equation 3

$$R_o = R/(1 + KT)$$

Equation 4

$$(K_1 * V) - (K_2 * I) = 0 \text{ or } V/I = K_2/K_1 = \text{heater resistance}$$

$$R = \frac{V}{I} = R_o * (1 + KT) \quad \text{Equation 5}$$

Equation 6

$$V_2 = V * (R_s/(R_s + R_l))$$

analog converter 2038 and the amplifier 2032 to provide a very small r.m.s (root mean square) voltage on conductor 2052. This allows the resistance measurement to be made without heating the restrictor appreciably.

If a fast A/D converter circuit is used, the voltage and current measurements can be made during a voltage pulse having a duration that is short compared to the thermal response time of the heater on the restrictor. In this case, the signal to noise ratio of the measurements is improved by applying the full voltage available from power amplifier 2032. The heating energy is low because the voltage is applied for only a short time. After measuring the resistance R at any known temperature T, $R_o$ is calculated from equation 3.

When the barrel of the valve restrictor or the outer tube of the capillary restrictor is used as the current return path, it and the resistance of conductors such as 3362 and 3363 (outside of the Kelvin connections) connected to the barrel contributes to the total resistance. Since the barrel of a valve restrictor may be at a different temperature than the heating coil at the orifice, its resistance and the resistance of any conductor lying upon it is not necessarily related to the orifice temperature. Similarly, the outer tube of capillary restrictor is not necessarily at the same temperature as the restrictor capillary. For most applications, it is not necessary to compensate for the outer tube or barrel temperature. The barrel or outer tube has a very much larger conducting cross-sectional area than the heater and the lead conductor lying upon the barrel is short. For this reason, and because it is insulated in the middle and heated to the same temperature at both ends, temperature variation of the barrel is not a significant factor.

The closed-loop temperature control can be performed by several means which control the output of the power amplifier driving the heater, whether wire or capillary. The power amplifier is adjusted to maintain the heater resistance at a constant value and therefore maintain a constant temperature. Although in the following implementations will emphasize the use of a valve restrictor with a heated orifice, the comments also apply to capillary restrictor electrically heated along its length. Three means (first to third) of implementing the control of the orifice temperature are as follows.

Firstly, a current sensing resistor is placed in series with the heater. The capillary current signal as sensed is amplified by this fixed resistor and the capillary voltage using separate gains which are opposite in polarity. The gains are chosen to balance the voltage signal with the current signal at the desired capillary resistance. An imbalance (difference) is amplified by the power amplifier to heat the heater and maintain the desired resistance. Feedback is completed by amplifying a voltage corresponding to the error in heater resistance.

Secondly, the heater resistance is computed as the ratio of measured voltage divided by measured current and this value is used as the feedback in a closed loop control system that maintains the heating wire resistance constant. The conductor resistance can be used to compute its temperature as described above. The computed orifice heater temperature is then used as the feedback signal in a closed loop temperature control circuit which accepts temperature as the control input and produces an electric output that both electrically heats the orifice and provides the measurement signals.

Thirdly, the orifice heater conductor is placed in one arm of a resistance voltage division circuit in series with a fixed resistor. The ratio of voltage across the orifice heater to the sum of voltages across the heater wire and fixed resistor is maintained constant. This in effect maintains a constant resistance ratio and therefore, a constant heater resistance. Feedback is completed by amplifying a voltage corresponding to the error of heater resistance. The heater resistance can be considered to be one of the four arms in a Wheatstone bridge.

Figure 22:
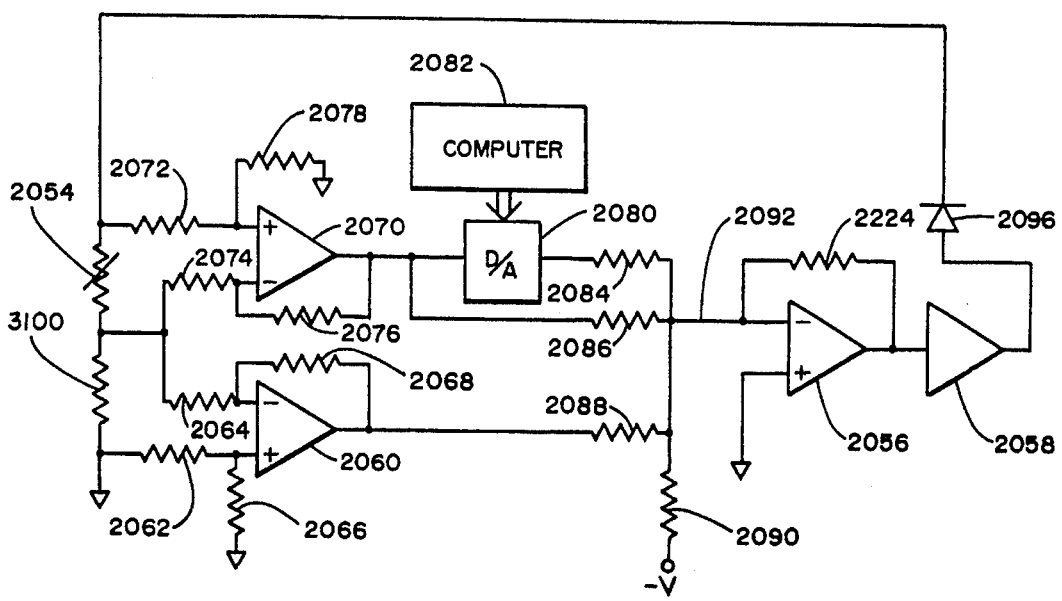
FIG. 22 is a schematic circuit diagram of a circuit useful in sensing the resistance and controlling the temperature of a restrictor in accordance with previous embodiments.

In FIG. 22, there is shown a schematic of a circuit that may be used to provide feedback control of the temperature of the restrictor orifice. This control method is similar to that described in U.S. Pat. Nos. 4,438,370 and 5,268,103, the disclosures of which are incorporated herein by reference.

With this circuit, the electrical power is applied to heater 2054 by servo-amplifier 2058. Current through heater 2054 is sensed by resistor 3100 and amplified by an inverting differential amplifier composed of amplifier 2060 and gain setting resistors 2062, 2064, 2066, and 2068 which produce a voltage proportional to the heater current and opposite in polarity. The voltage across heater 2054 is amplified by a non-inverting differential amplifier composed of amplifier 2070 and gain setting resistors 2072, 2074, 2076, and 2078. The output of amplifier 2070 is applied to the reference voltage input of digital to analog converter 2080.

Computer 2082, which controls converter 2080, selects the percentage of voltage at the output of amplifier 2070 to be applied to resistor 2084. The output of amplifier 2070 is also applied to resistor 2086. Resistors 2084, 2086, and 2088 connect to the summing node 2092 of amplifier 2056. Resistor 2086 and resistor 2084 with the D/A circuit inject a positive current into the summing node which is in variable proportion to the heater voltage. Resistor 2088 draws an opposing current from the summing node which is proportional to the heater current.

When these two currents are balanced, the output of amplifier 2056 is zero. The current gain and the voltage gain determine the ratio of heater voltage to heater current at which the summing currents will exactly offset each other. Resistor 2090 is connected to a negative voltage −V to turn on amplifiers 2056 and 2058 when the apparatus is turned on. This prevents the circuit from hanging up before heating starts.

This is expressed mathematically in equation 4 in which V=voltage across the heater, I=current through the heater, $K_1$=voltage gain associated with amplifier, 2070, D/A 2080 and resistors 2086 and 2084, and $K_2$=current gain.

These equations show that the null point can be shifted to a new ratio of voltage to current: a new temperature, by changing either gain $K_1$ or $K_2$. In practice, it is only necessary to change one gain as the desired heater resistance change is about 60 to 70 percent. Therefore, this circuit is designed to change the voltage gain over a range which will adjust the voltage/current ratio by about 60 to 70 percent. Resistors 2084 and 2086 are chosen to set the fixed and variable gains to achieve this result. The variable portion of the voltage gain is set by multiplying D/A 2080 with the set point provided by computer 2082.

If the heater temperature and therefore the heater resistance is lower than the set point, the positive current into summing node 2092 decreases. In addition, if the output voltage from amplifier 2056 is constant, the current through the heater increases due to the lowered load resistance. The increased current results in a larger current being drawn from summing node 2092 through resistor 2088. These two current shifts both act to shift the voltage at summing node 2094 below the non-inverting input of amplifier 2056. In response, the amplifier output voltage increases to balance the currents into and out of the summing node.

Figure 23:
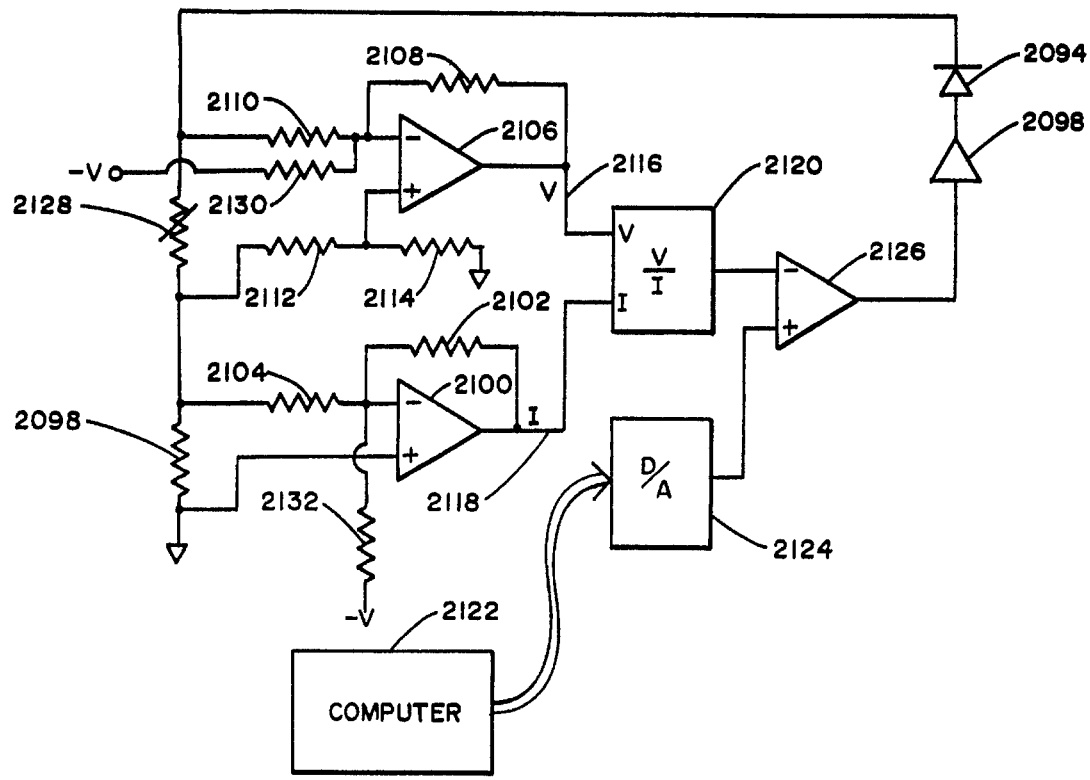
FIG. 23 is a schematic circuit diagram of a circuit that computes the electrical resistance of a restrictor for use in a temperature feedback loop control system.

The increased output voltage from amplifier 2056 drives servo-amplifier 2058 which heats heater 2054, which will increase its resistance and restore the voltage/current ratio selected by the computer. Amplifier 2058 is designed to have a transfer function which provides stable control of the heater temperature. A PID (Proportional-Integral-Derivative) transfer function of the type typically used in control systems is suitable. This closed-loop control system maintains the heater resistance, and therefore temperature at a selected value. Diode 2096 prevents reverse current flow through the heater wire 2054 if the temperature of the tube is higher than the set point value. FIG. 23 is a schematic circuit diagram of a circuit useful in calculating the resistance of the heater for control purposes in accordance with the embodiments of FIGS. 8, 9, 10, 15, 16, 22, 23, 28, 29, 30 and 31. The heater current is sensed by resistor 2098 and scaled in magnitude by amplifier 2100 and gain-setting resistors 2102 and 2104. The heater voltage is amplified by a differential amplifier consisting of amplifier 2106 and associated gain-setting resistors 2108, 2110, 2112, and 2114. The voltage signal conducted by conductor 2116 and the current signal conducted by wire 2118 enter ratio circuit 2120 where a signal proportional to the voltage divided by the current is generated. The relationship of resistance to temperature is described by equation 5, in which V=heater voltage, I=current through heater, R=heater resistance at temperature T, $R_o$=heater resistance at 0° Centegrade, and K=temperature constant for the heater wire. (K is about 0.004 for type Pelcoloy alloy. For a maximum overall temperature range of 150° C., this reflects a 60% change in resistance.)

Computer 2122 generates a digital resistance set point which is proportional to the desired heater temperature. The resistance signal is converted to a voltage by digital to analog converter 2124. The resistance feedback signal from ratio circuit 2120 is subtracted from the resistance set point signal from D/A circuit 2124 by differential amplifier 2126 and this difference or resistance error signal is amplified by power amplifier 2098 to heat the heater conductor 2128.

The resistor 2130 is led from a negative potential to the inverting input of amplifier 2106 and resistor 2132 is similarly led to the inverting input of amplifier 2100 to insure turn-on of amplifier 2098 when the apparatus is turned on. This prevents the circuit from hanging up before the heating starts. The amplification transfer function is designed to heat the capillary when the resistance, and therefore the temperature, is too low. The transfer function of amplifier 2098 is of the usual proportional-integral-derivative (PID) type used in control systems. Diode 2094 illustrates that the control signal is unidirectional, or that it can only run current through the heater in one direction.

As the heater heats, its resistance increases until the voltage/current ratio matches the set point from computer 2122. This control system functions as described to maintain a constant ratio of heater voltage to heater current and therefore a constant heater resistance. The theory of operation is the same as given in explanation of FIG. 21, and the same equations apply. Elements such as the ratio computation, and other control computations can be performed by a computer if one is present in the system.

Figure 24:
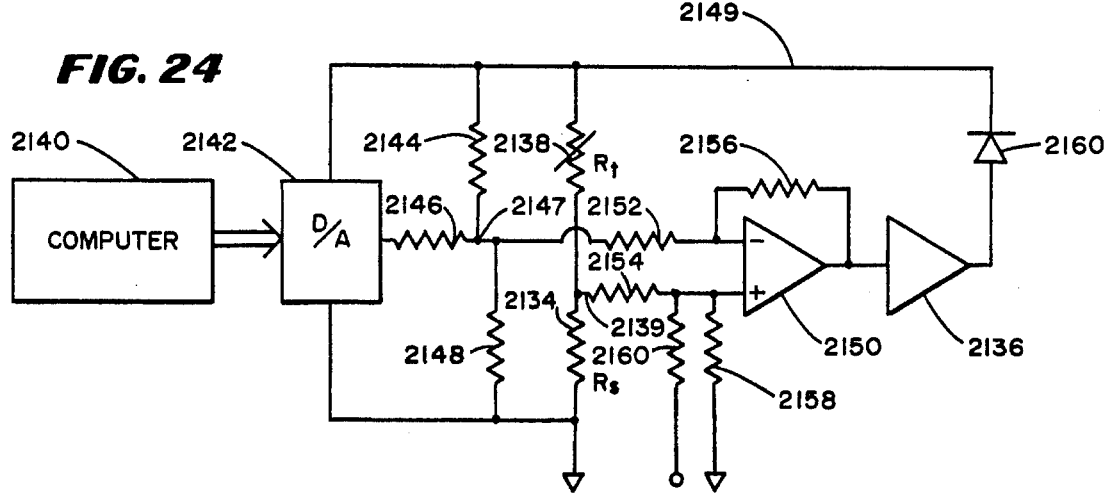
FIG. 24 is a schematic circuit diagram of the bridge circuit useful in the control system for the temperature of a restrictor.

FIG. 24 is a diagram of implementation number three. The heater 2138 is connected in series with current sense resistor 2134. The voltage $V_2$ across resistor 2134 is equal to the output voltage of amplifier 2136 multiplied by the ratio of resistor 2134 ($R_s$ divided by the sum of resistor 2134 plus the heater 2138 resistance ($R_t$) as shown in equation 6.

Set point voltage $V_1$ is generated by computer 2140 in conjunction with digital to analog converter 2142. The reference voltage for the D/A converter is the amplifier voltage V (2149) or a voltage proportional to V. In this way, the output of the D/A circuit is equal to the digital input multiplied by the amplifier output voltage V. The D/A output is shifted and scaled by a level shift circuit composed of resistors 2144, 2146, and 2148.

Since the heater resistance change over a typical operating temperature change of 150° C. is only about 60 to 70 percent, it is preferable to shift the D/A output and compress the full scale set point voltage $V_1$ into the operating range of feedback signal $V_2$. The set point voltage $V_1$ is a percentage of servo amplifier output voltage V with the percentage determined by the output of computer 2140. The voltage $V_1$ is subtracted from $V_2$ and amplified by a difference amplifier composed of amplifier 2150 with resistors 2152, 2154, 2156, and 2158. The output current from servo-amplifier 2136 heats heater 2138 so as to maintain the voltage $V_2$ at the set point voltage $V_1$. Resistor 2160 is electrically connected to positive voltage $V_3$ to turn on amplifier 2150 and 2136 when the apparatus is turned on. This prevents the circuit from hanging up before heating starts. The amplified error signal is applied to heater 2138 through diode 2160 to heat the heater.

As an example, suppose that the heater 2138 temperature is lower than desired. The resulting resistance will be lower than the set point value. As a result, voltage $V_2$ will be larger than set point voltage $V_1$. Amplifier 2136 incorporates the usual PID transfer function and amplifies the derived difference or error signal and heats heater 2138 to increase its resistance and restore the balance between $V_1$ and $V_2$.

Although the restrictor valves described earlier are relatively plug-free, they still tend to plug when extracting difficult samples. Perhaps the worst is elemental sulfur bearing samples such as certain river sediments. Many other solid or semisolid analytes are also a problem. A new valve of the preferred embodiment, which works very well with such difficult samples, will now be described.

In FIGS. 28, 29, 30 and 31, there are shown the valve restrictor, automatic restrictor or variable restrictor of the preferred embodiment. As best understood from these drawings, the restrictor operates as follows.

When the valve is closed, the 45 degree included angle needle tip 3352 is held against the valve seat 3314 under spring force generated by spring 3303, through ball 3304, bearing surface 3306, and needle or stem 3308 which lies within tubular probe 3372. In this position, flow is stopped by closure of the valve seat 3314. Seat 3314 has a 45 degree included internal angle, matching the external included angle of the needle or stem tip 3352. Equal seat and needle tip angles provide more contact area and therefore are relatively robust. The annular orifice 3371 formed by needle tip 3352 and seat 3114, where fluid metering takes place, is distanced from valve body 3312 by elongated barrel 3353, which is the core of an elongated tubular probe 3372 with the valve control body 3312 and fluid inelt 3357 at one end of probe 3372, and the fluid metering valve orifice 3371 in the opposite end of the probe. The restrictor valve is shown opened in FIG. 26.

In this position, supercritical fluid is intended to enter the inlet 3357 (FIG. 25), flow the length of the interior passage of tubular probe 3372 and flow out the orifice 3371. When it is closed, needle tip 3352 is flush with, or protrudes several thousandths of an inch from orifice 3371. This prevents needle tip 3352 from pressing a ring-shaped step into the seat 3314. Gear 3309 is fastened to lift 3310. As servomotor 3307 operates to open the valve, it rotates 11-tooth pinion 3351 (FIG. 28), causing 192-tooth gear 3309 to rotate, which causes the tubular lift 3310 to unscrew because of external threads 3311 (FIG. 25) cooperating with internal threads in bushing 3368. This moves the lift 3310 upward. Threads 3311 are fine threads, at least 20 threads per inch and 80 threads per inch in the preferred embodiment. The inside diameter of tubular lift 3310 is a slip fit on the needle 3308. Assume to start that the valve is shut with needle tip 3352 in positive contact with seat 3314. As the lift starts to move upward, the needle 3308 is not coupled to the rotation of the lift, preventing galling of the needle tip 3352 in the seat 3314. As the lift continues to move upward, it comes in contact with the cap 3350 of the needle 3308, causing the base to pull upward on the needle. As the top 3373 of the lift 3310 contacts the cap of the needle, the top of the lift imparts a rotational friction torque on the needle. The top 3373 of the lift 3310 is chambered to form a frustum of a cone. The resulting decrease in maximum contact radius decreases the rotational torque to a desired amount. Upward movement of the gear 3309 and lift 3310 decreases the downward force of the needle tip 3352 against seat 3314, thereby decreasing the static friction torque between the needle tip and the orifice and between the side of needle 3308 and the inside wall of barrell 3353.

When the gear 3309 and lift 3310 rotate sufficiently further, the rotational friction torque between lift 3310 and needle cap 3350 becomes greater than the static frictional torque between needle tip 3352 and seat 3314 plus the static frictional torque between the side of needle 3308 and the inside wall of metal barrel 3353. At this point, needle 3308 rotates with gear 3309, assisting in smooth lifting motion of the needle by breaking or scouring away analyte that may have deposited between tip 3352 and seat 3314, or between the side of needle 3308 and the inside surface of metal barrel 3353. This is a self-cleaning action that takes place when there is little or no contact force between the needle tip 3352 and the seat 3314, and therefore no damage to the needle tip or seat. Flow regulation is accomplished by axially positioning the needle by the motor driven lift. Note that the needle 3308 is not engaged in screw threads 3311, so screw thread friction does not affect the precise positioning and application of force.

A conventional automatic restrictor valve with axial-only motion of the stem or needle has a tendency to pack or tamp deposited analyte into the valve seat where it builds up and causes erratic or gross hunting motion of the servo-driven stem, producing erratic flow rates. The automatic restrictor valve of the preferred embodiment has controlled rotary motion of the stem due to frequent and minor servo adjustment action whenever the valve is partially open. This produces a scouring action on any deposited analytes so they do not build up on the seat. The result is a much more constant and reproducible flow rate. Servomotor and servo control arrangements are described in accordance with FIGS. 1, 3, 14, 15, 16 and 17. Such arrangements control the extraction system pressure or flow rate or both by programming. Both pressure and flow rate change during a change in the pressure setpoint.

During closing, the needle rotates and moves downward with the lift until the tip 3352 contacts the seat 3314. The rotational (tangential) movement clears away deposited analyte that may be on the needle tip 3352 or seat 3314. After further rotation, the static torque at the needle tip exceeds the rotational torque at the needle base 3350 and the lift 3310 is no longer able to impart enough rotational torque on the needle to turn it, preventing galling as the needle tip 3352 comes into positive contact with the seat. The needle is held in a valve-closed position by spring force exerted by spring 3303 through ball coupling 3304 and 3306. This spring force may be between 10 and 300 pounds and preferably is about 55 pounds. As the lift continues to move downward, only spring force is exerted on the needle, so damaging overclosure force is not possible.

When the needle rotates, relative motion of the surface of the needle tip 3352 with respect to the seat 3314 has a tangential (rotary) component of motion and an axial (opening or closing) component of motion. The mean tangential motion along the tapered tip should be at least equal to the axial motion to provide adequate cleaning action. In the preferred embodiment, the mean tangential motion is about eight times the axial motion.

Optical sensor 3316 and flag 3317 attached to gear 3309 provide reference position sensing for one rotation of the gear. Optical encoder 3354 provides fine sensing of the shaft rotation of servomotor 3307, gear and lift position for feedback purposes (FIGS. 14 and 17), and has a resolution greater than 1/50 of a revolution, and preferably is sensitive to 1/2048 of a revolution. Position feedback is required for stable control of flow or pressure with the autorestrictor, and is implemented as described earlier in this disclosure in connection with FIGS. 14 and 17. The resolution of the preferred embodiment is $11/(192 \times 80 \times 2048) = 0.35$ microinch movement of the needle 3308. The resolution is smaller than 40 microinches and preferably smaller than 5 microinches. Gear 3309 is a precision gear and the position of the motor is adjusted to provide very low backlash between pinion 3351 and gear 3309.

Regulated heating element 3355 heats the metal barrel 3353 near the orifice 3371 to prevent freezing of entrained freezable liquid due to cooling from $CO_2$ phase change or Joule-Thomson expansion and to at least decrease the tendency toward analyte deposition. The heater can heat the orifice to at least +30 degrees Celsius and preferably to +150 degrees Celsius. When a solvent trap is used, the orifice is immersed in the midst of the solvent so that no connecting tubing is used between orifice and solvent. Such connecting tubing is susceptible to plugging. The immersion of the orifice is enabled by locating the orifice on the end of a long narrow probe. The fluid conditions inside the probe are supercritical so no analyte or frozen-liquid deposits occur. With conventional orifice location on a valve body instead of in the probe, a connecting tube would be necessary to extend the fluid path from the orifice into the midst of the trapping solvent. The pressure in this tube would be atmospheric, causing deposition problems and plugging. However, even with probe having a heated orifice at its tip, the self-cleaning action described above is still necessary, especially with problem extractions, where all three of these features are necessary: scouring, heating and elimination of connecting tubing operating at atmospheric pressure.

Thermostat-controlled heating element 3356 heats valve block 3312, to prevent deposition in the valve block. Molded plastic sheath 3313 electrically and thermally insulates barrel 3353 and heater 3315. Barrel 3353 and sheath 3313 extend five inches from the bottom 3364 of valve of the probe 3372 and the outside diameter of the sheath is 3/16 inch. The ratio of barrel length to sheath diameter exceeds 4, and preferably should exceed 10. Barrell length should exceed 1 inch. The diameter of probe 3372 (including sheath, if any) should not exceed 0.5 inch. These barrel dimensions and ratios also apply to the other elongated probe embodiments including those generally depicted in FIGS. 7, 8, 9, 10, 12, 13, 15 and 16. In these foregoing embodiments as well as the preferred embodiment, the restrictor valve has an elongated fluid-conducting probe with a variable orifice at the distal end and means controlling the orifice at the proximal end of the probe.

Conductors 3362 and 3363 provide Kelvin-connections for a temperature control power supply and temperature self-sensing of high temperature coefficient heater 3355 as described earlier in regard to FIGS. 8, 9, 10, 11, 24, 25, 27, and 28. The corresponding heater in FIG. 9 is identified as 1201. In the preferred embodiment heater 3355 is double polyamide film insulated 0.004 inch diameter Pelcoloy (Molecu-Wire Co.) wire, and is placed on barrel 3353 as further described in conjunction with FIG. 9 and FIG. 10.

Inlet port 3357 is connected to the analyte outlet of a supercritical extractor and feeds analyte plus supercritical fluid down into the narrow clearance space between the needle 3308 and the inside of barrel 3353, to the needle tip 3352. Upward fluid flow is prevented by seal 3379. In the preferred embodiment, the main diameter of the needle 3308 is 0.068 inch and the main inside diameter of the barrel is 0.075 inch. The main outside diameter of the barrel is 0.120 inch. The needle is made of cold drawn 17-7RH stainless steel hardened according to CH900; producing a tensile strength of 290,000 psi. The barrel 3353 in the region of the seat 3314 is made of 15-7 Mo stainless steel hardened according to RH950; producing a tensile strength of 200,000 psi. With regard to the seat and the needle, they are preferably not of the same hardness; the needle should be harder than the seat.

The narrow clearance between the needle 3308 and the bore of tubular barrel 3353 is preferred because the needle is a buckled column constrained by the bore of the barrel. The needle assumes the shape of a bow, with the point of maximum excursion rubbing against the inside of the barrel. The circumferential portion of the bow within the barrel is affected by two opposing forces: 1) the tendency of the bow to orbit at the same rate and direction as the rotation of the needle about its own axis, and 2) the effect of traction of the needle against the inside wall of the barrel tending to cause the needle to orbit in the opposite direction. The side thrust and therefore the friction thrust of the bow in the high length-to-diameter ratio needle against the inside of tubular barrel is approximately proportional to the clearance. The clearance is preferably 0.007 inch, earlier was 0.013 inch in a previous embodiment, and should not be greater than 0.030 inch. In a previous embodiment the needle and barrel walls were rough, producing a large and erratic coefficient of friction.

In the preferred embodiment, effort has been made to reduce needle-to-barrel wall friction coefficient to improve flow stability. Effort also has been put into making the coefficient uniform. The barrel has a smooth inside finish, better than 16 microinches rms and preferably 8 micorinches. The needle is polished to at least 16 microinches rms surface finish, and preferably 8 microinches, and then is plated overall, sides and tip, with 0.0005 inch thickness of hard gold to provide low friction.

Fine finishes and gold plating on the side of the needle as well as on the needle tip improves performance, as side thrust forces of the bowed needle against the inside of the barrel are calculated to be low, on the order of 0.7 pound in the previous embodiment with 0.013 inch clearance between needle and barrel. Friction was also low, but was found to produce the erratic behavior in the adjustability of the valve. The improvement in adjustability because of closer clearance, finer finishes and gold plate may be due to lessening of stick-slip friction effect which irregularly causes frictional tractive forces on the stem as it bows and orbits against the barrel, followed by sudden loss of traction and change in orbital position of the bowed stem within the barrel, as a continuous and smooth change in adjustment is made. Another possibility is that the point of maximum bow in the needle scuffs irregularly in the axial direction along the inside wall as the needle is adjusted axially. The preferred low and uniform friction coefficient and decreased thrust will greatly decrease this problem, too.

Figure 28:
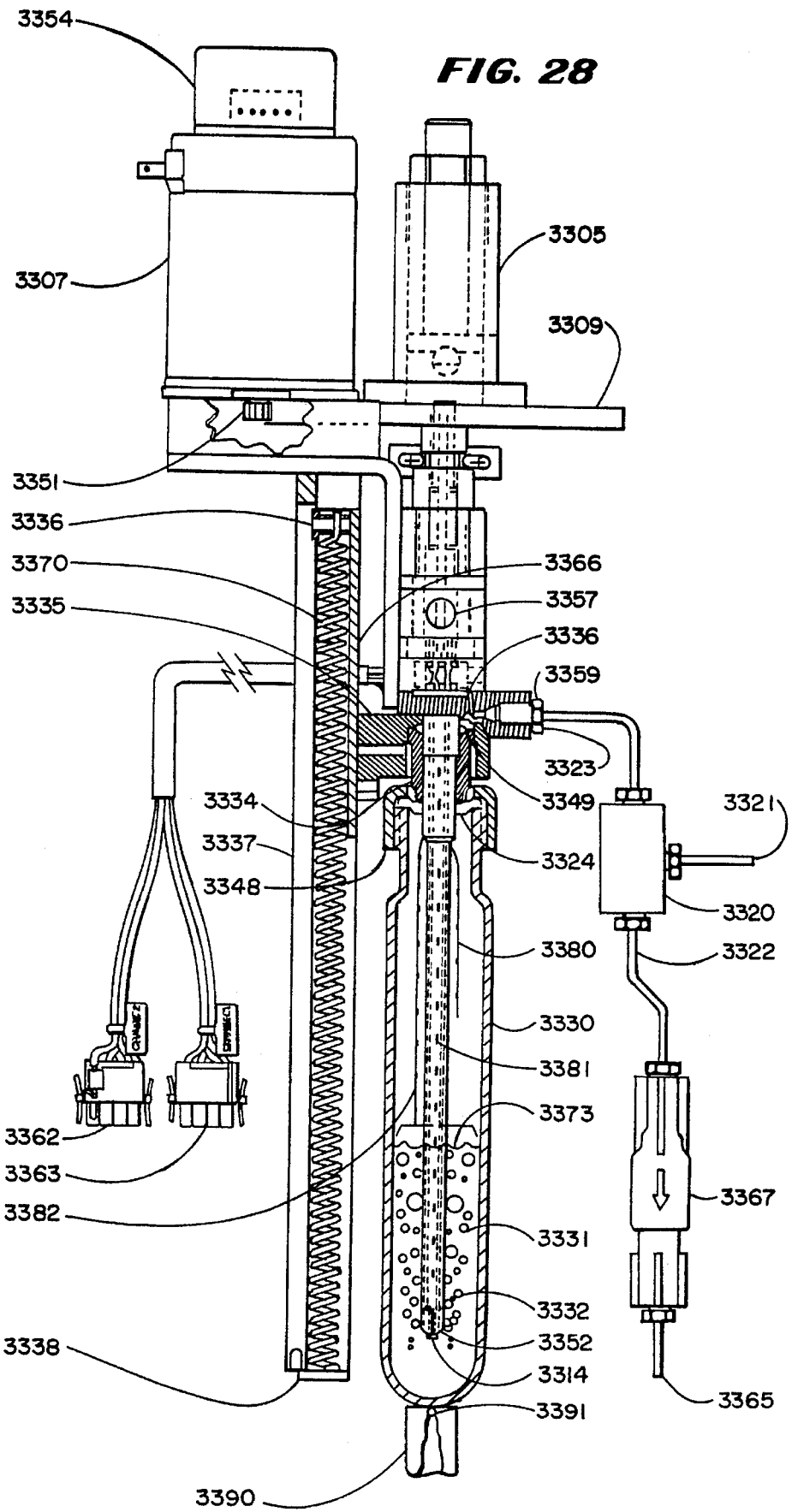
FIG. 28 is a partially sectioned, partially broken away side view of the restrictor of FIG. 25 with a solvent-trap collecting tube in place to illustrate action of the restrictor and a collection means.

FIG. 27 is a top view of FIG. 25 and shows the relative positions of the motor 3307 and 192 tooth gear 3309. In FIG. 28, there is shown a schematic side view illustrating the operation of the restrictor. Before operation starts, the lift guide 3335 is at the bottom of vertical lift track 3337. In operation, elevator 3390 carrying thermocouple 3391 lifts a collection vial 3330 with a cruciform-pierced or slitted rubber septum 3324 held by plastic cap 3348 upward from under the orifice 3314 of the barrel so that the orifice, then the barrel, and then makeup trapping solvent supply tube 3361 thread through the pre-pierced septum. Septum 3324 is made of rubber with a thin, bonded PTFE film on the side toward the solvent 3331. For good reclosure properties, the rubber must contribute much more stiffness to the septum than does the PTFE film. Tube 3361 is coaxially disposed outside barrel shield 3313 and there is an annular makeup fluid flow space between them.

As the vial 3330 is lifted it raises the lift guide 3335 to the raised position shown in FIG. 28. The vial is filled to the desired level of trapping solvent 3331. With the collection vial completely lifted, the septum 3324 is pressed against the nose piece 3334 by spring 3370, creating a sufficient seal for over 40 psi. At a pressure above the sealing pressure, the spring stretches further causing nose piece 3340 to lift and act as a safety valve. The cruciform-pierced slits (not shown) cut in the septum allow the gas to escape upward along the outer surface of tube 3361, through an annular flow space between tubes 3360 and 3361, and out through port 3359, as shown by path 3382. Pressure is regulated to about 30 psi gauge with an external pressure regulator 3367. The minimum advantageous pressure is 15 psi gauge. Leakage of gas around the outside of vent tube 3360 is prevented with an O-ring 3349.

The coaxial vent tube 3360 does not press through the septum, because its diameter is large enough to significantly deform the septum, so that it will not re-close. The trapping solvent is cooled by directing liquid $CO_2$ through cooling expansion lines 1614 and 1648 (FIG. 20) onto the lower part of vial. The temperature of solvent 3331 is cooled under control by a $CO_2$ valve and temperature controller (not shown) connected to thermocouple 3391 (FIG. 28).

In operation, the distal (variable orifice) end 3371 (FIG. 26) of the elongated probe 3372 (FIG. 25) extends below the surface 3373 (FIG. 28) of trapping solvent 3331.

The orifice 3371 is substantially surrounded by the trapping solvent 3331. Surrounding of the orifice with the trapping medium provides improved collection efficiency whether the trapping medium is a solvent, absorbent particles or inert cryotrapping particles. Cooling and pressurizing the trapping medium in collecting vial 3330 further proves the collection efficiency. The trapping medium should be coolable to +5 degrees Celsius and preferably to −20 degrees Celsius. Such temperature control is particularly important because the heated orifice 3371 is immersed in the trapping medium. In the case of a solvent trap, the solvent does not actually contact the flow metering passage of the orifice because of the gas flow leaving the passage, but heat conduction still takes place. Temperature control and pressurization of a collection vessel to a pressure equal to the extraction chamber pressure is disclosed in Nam, et. al, *Chemosphere*, 19, No. 1–6 pp 33–38 (1989). Nam does not disclose gassifying a supercritical fluid through a restrictor, nor regulated control of collecting vessel pressure nor the heating of a restrictor. Neither is there disclosure of an insulated, variable nor automatic restrictor. Nam's system is for static extractions and is not suitable for dynamic or flowing extractions.

Vent port 3359 (FIG. 25) is connected to the annular flow space inside tube 3360 and make up Solvent make-up port 3358 is connected to the annular flow space inside tube 3358. In a following step of operation, analyte and supercritical fluid pass into port 3357 and out the space between needle tip 3352 and seat 3314. Refer to FIG. 28. The supercritical fluid gassified at the orifice 3371, passes through trapping solvent 3331 as gas bubbles 3332 which pressurize the collecting tube 3330. Analyte entrained in the gas dissolves in the trapping fluid as the bubbles pass upward. The gas rises above the solvent 3331, passes through the slits in the septum 3324, into the annular space under tube 3360 and is discharged through port 3359. Pressurization of the collection vial by back pressure regulator 3367 prevents misting of solvent which would carry off analyte in the droplets of mist.

If the collecting vial is used as a solvent trap as shown, some of the solvent may evaporate and also be carried out vent port 3359. To keep the solvent level in the vial constant, a conventionally programmed supply of make-up solvent (not shown) is fed into make up solvent port 3358 and discharged into the collecting tube through the annular orifice inside tube 3361. Extraction and collection conditions may readily be controlled well enough to insure the run-to-run reproducibility necessary to keep solvent level constant with preprogrammed, open loop solvent addition control. An absorbent or cryogenic trap may be used in place of solvent 3331 in vial 3330.

In any case, during trapping of analyte, variable orifice 3321 at the end of barrel 3353 is in the midst of the trapping medium whether such medium is solvent, absorbent or inert cryotrapping material. The variable orifice is in the midst of the medium as opposed to not being buried well within the medium. Specifically "midst of the medium" means that the distal end of elongated probe carrying the variable orifice enters and protrudes into the trapping medium, and penetrates to a depth greater than one-half of the distance from the point of entrance to the center of the medium. This improves collection efficiency. Such orifice location also applies to the embodiments of FIGS. 7, 8, 9, 10, 12, 13, 15 and 16.

During extraction the motor operates the valve under servo control to maintain a preset flow rate regardless of pressure variations, or to maintain a predetermined pressure for the supercritical extraction regardless of flow rate changes. At the end of extraction vent valve 3320 connects atmospheric vent 3321 to vent port 3359, discharging the pressure in vial 3330. After a short wait for equilibrium, the vial 3330 containing collected analyte is lowered and removed. The cruciform slits in the septum 3324 re-close when vial 3330 is withdrawn from probe 3372, resealing the vial 3330.

In general, particulate-filled absorbence traps and cryotraps do not perform well when the supercritical fluid extractant contains a liquid modifier or co-solvent. This is because the modifier liquid fills the interstices between absorbent or cryotrapping particles, decreasing their surface area and the collection efficiency. The problem is worse with absorbent traps as the modifier inactivates the absorbent, further decreasing the collection efficiency. Solvent traps do not have this disadvantage as the modifier dissolves in the trapping solvent without degrading its trapping properties.

Heretofore, solvent traps have been considered less desirable than absorbent traps because of: (1) the conflicting nature of ways to ameliorate plugging and to improve collection efficiency as described herein, and (2) the difficulty of automation of trapping with a solvent.

The invention is particularly advantageous when practiced with a solvent trap. A variable restrictor with a tubular probe separating its inlet and control means from its restrictor valve orifice allows the orifice to be dipped directly into the solvent to provide high collection efficiency without connecting tubing that would be subject to plugging. Controlled scouring means in the valve prevents it from plugging internally, and without damage to itself. A heater heats the orifice to overcome cooling due to phase change or Joule-Thomson expansion of the extracting fluid to a gas and thereby to decrease and soften incipient deposits. Cooling of the collection solvent overcomes the solvent-heating effect of the orifice heater and further cools the solvent to improve the trapping of volatile analytes. Pressurization of the collection vessel improves collection efficiency by further decreasing loss from vaporization of analyte and preventing the misting of trapping solvent which would carry off dissolved analyte. A detailed description is given of means for automating the entire process of supercritical extraction including an improved restrictor and solvent trap.

As can be understood from the above description, the supercritical extraction technique has several advantages, such as for example: (1) it automates the sample injection and fraction collection part of the extraction process as well as automating the extraction itself; (2) provides a superior solvent trap that performs better than previous solvent, absorbent or cryotraps; (3) it provides improved trapping efficiency; (4) it provides low extract/solvent losses; (5) it eliminates analyte deposition, freezing and plugging of the restrictor; (6) it provides constant and reproducible flow of the extractant for reproducible extractions; (7) it permits the conditions of the extraction, such as temperature and pressure, to be changed so as to remove certain substances from the sample matrix and deposit each substance in a separate vial; (8) it is also useful for investigating extraction kinetics by changing the vial during the extraction for examination; (9) it permits the use of different size vials because the stroke of a lift is no longer tied to the extraction cartridge elevator; and (10) it permits the use of multiple wash stations to clean the outside of the restrictor.

Although a preferred embodiment of the invention has been described in some detail, many modifications and variations of the preferred embodiment can be made without deviating from the invention. Therefore, it is to be understood that within the scope of the appended claims the invention may be practiced other than as specifically described.

What is claimed is:

1. Apparatus comprising:

a plurality of sample containers;

at least some of said plurality of sample containers being adapted to hold a different one of a corresponding plurality of samples;

a first transport means;

said first transport means being adapted to carry said plurality of sample containers;

a second transport means;

programming means for causing said first transport means to move a selected sample container and sample to the location of said second transport means;

a supercritical extractor;

said programming means including means for causing said second transport means to move said selected container and sample from the said first transport means to a supercritical extraction means;

means for sealing the selected container at the place of extraction to resist the said extraction pressure;

means for heating sample container at the place of extraction; and means for passing fluid at said supercritical condition through the said selected sample container and sample, thereby extracting an analyte from the sample.

2. The apparatus of claim 1 further including programming means for causing the second transport means to move the selected container out of the extraction means and back to the first transport means after the extracting of analyte.

3. The apparatus of claim 2 wherein the direction of motion of the said second transport means is vertical.

4. The apparatus of claim 3 wherein the direction of motion of the said first transport means is horizontal.

5. The apparatus of claim 2 wherein the direction of motion of the said first transport means is horizontal.

6. The apparatus of claim 2 in which another sample container and sample is selected from the said first transport after a previous sample has been extracted.

7. Apparatus according to claim 2 further including a fraction collector; said fraction collector including means for receiving analyte from a sample and depositing the analyte in a corresponding one of a plurality of analyte receptacles.

8. Apparatus according to claim 7 including means for causing the analyte extracted from each of said plurality of samples to be collected in a corresponding one of said plurality of analyte receptacles.

9. The apparatus of claim 1 wherein the direction of motion of the said second transport means is vertical.

10. The apparatus of claim 9 wherein the direction of motion of the said first transport means is horizontal.

11. Apparatus according to claim 9 further including:
a fraction collector;
said fraction collector including means for receiving analyte from a sample and depositing the analyte in a corresponding one of a plurality of analyte receptacles.

12. Apparatus according to claim 11 including means for causing the analyte extracted from each of said plurality of samples to be collected in a corresponding one of said plurality of analyte receptacles.

13. The apparatus of claim 1 wherein the direction of motion of the said first transport means is horizontal.

14. The apparatus of claim 1 in which another sample container and sample is selected from the said first transport after a previous sample has been extracted.

15. Apparatus according to claim 1 further including a fraction collector; said fraction collector including means for receiving analyte extracted from a sample and depositing the analyte in a corresponding one of a plurality of analyte receptacles.

16. Apparatus according to claim 15 including means for causing the analyte extracted from each of said plurality of samples to be collected in a corresponding one of said plurality of analyte receptacles.

17. Apparatus according to claim 15 further including a variable-orifice fluid restrictor and means for automatically adjusting the variable-orifice fluid restrictor to maintain pressure in the supercritical extractor during collection of the analyte.

18. Apparatus according to claim 17 wherein the variable-orifice fluid restrictor further includes motor control means for adjusting said outlet orifice means.

19. Apparatus according to claim 18 wherein the variable-orifice fluid restrictor further includes a biasing means, said motor control means being arranged to move said outlet orifice means in a first direction against pressure from said biasing means, wherein said biasing means moves the outlet orifice means in the opposite direction.

20. Apparatus according to claim 18 wherein the variable-orifice fluid restrictor further includes heating means for heating of said variable-orifice restrictor.

21. The apparatus of claim 1 further including:
locking means for retaining the selected sample container in the said place of extraction; and,
said locking means disposed to resist the force produced by the said extraction pressure.

22. The apparatus of claim 21 wherein said locking means and said second transport means each are constructed to separately aid in retaining the selected sample container in said place of extraction.

23. Apparatus for automatic high-temperature high-pressure extraction processing of a sample with an extraction fluid comprising:
more than two samples each in individual sealable sample containers located in a first transport means;
said sample containers insertable and removable from the said first transport means;
said sample containers having a first flow port and a second flow port, and the said sample disposed between the said flow ports;
programming means for causing first transport means to move a selected one of the said more than two sample containers with its contained sample to a location corresponding to a place of extraction;
means for heating the said selected sample container and extraction fluid to a set temperature;
means for pressurizing said process of extraction within a pressure vessel means;
said selected sample container at the said place of extraction being sealed to the pressure of said pressurizing;
extraction fluid flow means producing an extraction fluid flow;
a first connecting means disposed to conduct fluid from the said extraction fluid flow means to the first flow port of the selected sample container;
said extraction fluid flow means forcing extraction fluid through said first fluid flow connecting means and through the first flow port of said selected sample container containing said sample wherein said extraction fluid contacting said sample at said heated and pressurized conditions produce an extract from the sample;
a plurality of collection containers located in a second transport means;
said programming means causing the selection of a collection container in the said second transport means in correspondence with the said selection of a sample container in the said first transport means;
said second fluid flow connecting means being disposed to conduct said extract from the said second flow port of the said selected sample container containing sample to the said selected collection container to receive said extract, wherein means are provided for forcing flow of extraction fluid with extract from the said selected sample container to the said selected collection container;
said selected collection container receiving extract from only one selected sample container; and
said second transport means moving the said selected sample container after the said container has received extract.

24. The apparatus of claim 23 wherein the means for heating includes means for setting set temperature to a temperature at least as high as 150 degrees Celsius.

25. The apparatus of claim 24 further including a third transport means for bringing the selected sample container and the heating means into proximity to cause the sample container to be heated to the said set temperature.

26. The apparatus of claim 23 further including:

an automatically controlled valve connected in line with the said second connecting means;

said programming means causing said valve to open at a first time permitting said flow of extract from the said selected sample container to the said selected collection vessel; and, said programming means causing the said valve to close at other times.

27. The apparatus of claim 26 further including a third transport means for bringing the selected sample container and the heating means into proximity to cause the sample container to be heated to the said set temperature.

28. The apparatus of claim 23 in which the said first and second transport means are rotary carousels each carrying sets of adjacent containers; and said carousels moving in step by step coordination with each other so that each collection container corresponds to a single particular sample container.

29. The apparatus of claim 28 in which each sample container corresponds to a single particular collection container.

30. The apparatus of claim 28 further including a third transport means for bringing the selected sample container and the heating means into proximity to cause the sample container to be heated to the said set temperature.

31. The apparatus of claim 23 further including a third transport means for bringing the selected sample container and the heating means into proximity to cause the sample container to be heated to the said set temperature.

* * * * *